United States Patent [19]
Irie et al.

[11] Patent Number: 5,485,241
[45] Date of Patent: Jan. 16, 1996

[54] OPTICAL EQUIPMENT WITH DEVICE FOR DETECTING DIRECTION OF VISUAL AXIS

[75] Inventors: Yoshiaki Irie; Akira Yamada, both of Yokohama; Akihiko Nagano, Ichihara, all of Japan

[73] Assignee: Canon Kabushiki Kaisha, Tokyo, Japan

[21] Appl. No.: 386,200

[22] Filed: Feb. 9, 1995

Related U.S. Application Data

[63] Continuation of Ser. No. 115,018, Sep. 2, 1993, abandoned.

[30] Foreign Application Priority Data

Sep. 7, 1992 [JP] Japan ................................ 4-264290
Oct. 29, 1992 [JP] Japan ................................ 4-291505

[51] Int. Cl.$^6$ .................................................... G03B 13/02
[52] U.S. Cl. ............................................ 354/410; 354/219
[58] Field of Search .............................. 354/410, 62, 219

[56] References Cited

U.S. PATENT DOCUMENTS

| | | | |
|---|---|---|---|
| 3,864,030 | 2/1975 | Cornsweet | 351/7 |
| 5,182,443 | 1/1993 | Suda et al. | 354/219 |
| 5,245,371 | 9/1993 | Nagano et al. | 354/62 |
| 5,260,734 | 11/1993 | Shindo | 354/219 |
| 5,280,312 | 1/1994 | Yamada et al. | 351/211 |

FOREIGN PATENT DOCUMENTS

| | | |
|---|---|---|
| 1-274736 | 11/1989 | Japan . |
| 3-107909 | 5/1991 | Japan . |
| 4-138432 | 5/1992 | Japan . |
| 1380355 | 1/1975 | United Kingdom . |
| 2117594 | 10/1983 | United Kingdom . |
| 2177276 | 1/1987 | United Kingdom . |

*Primary Examiner*—W. B. Perkey
*Attorney, Agent, or Firm*—Fitzpatrick, Cella, Harper & Scinto

[57] ABSTRACT

An optical apparatus with a visual axis detecting device for converting the light reflected from the eyeball into an electrical signal and calculating the direction of visual axis from the electrical signal.

Plural pairs of illuminating light sources are provided around the view finder, and one of the pairs is turned on to illuminate the eyeball, according to the output of a position detector detecting whether the optical apparatus is in a vertical or horizontal position, or of a distance detecting circuit for detecting the distance between the view finder and the eyeball, or of a judging circuit for judging whether the photographer wears spectacles or not, thereby enabling precise detection of the direction of visual axis.

43 Claims, 39 Drawing Sheets

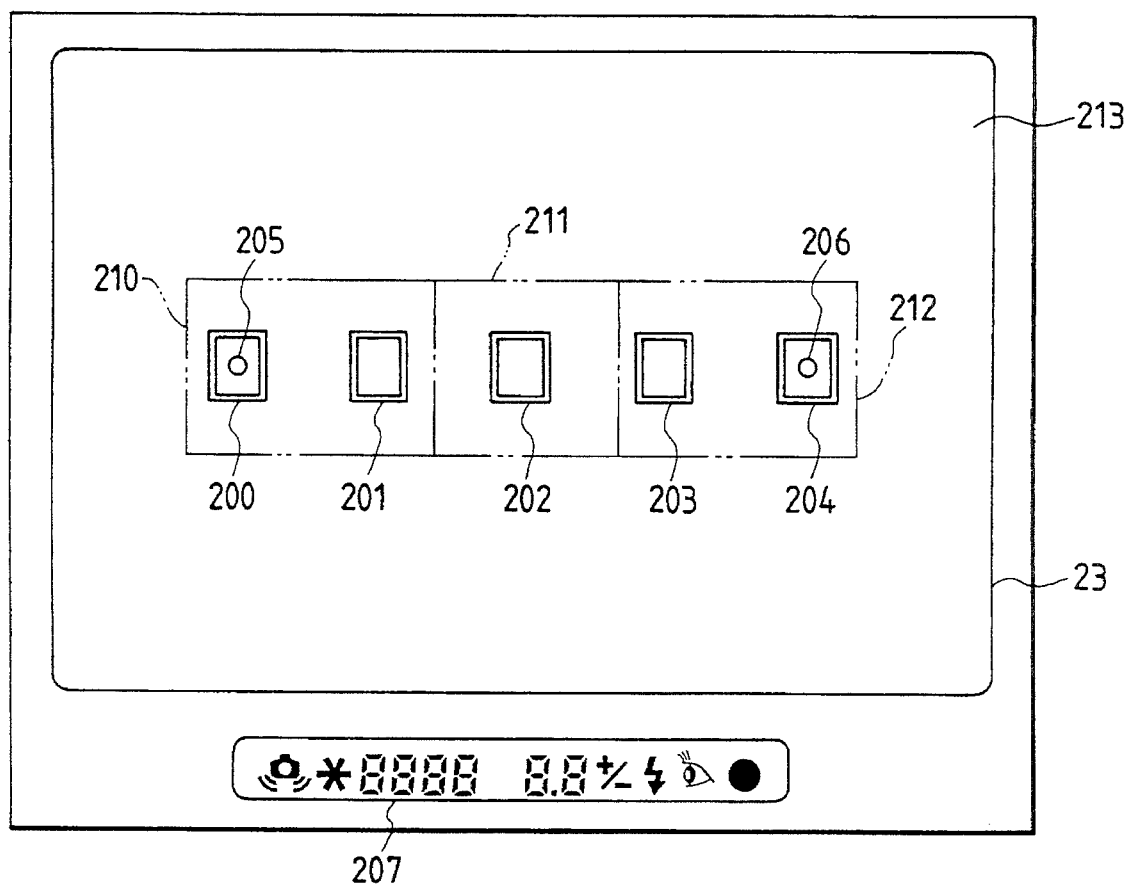

FIG. 5A
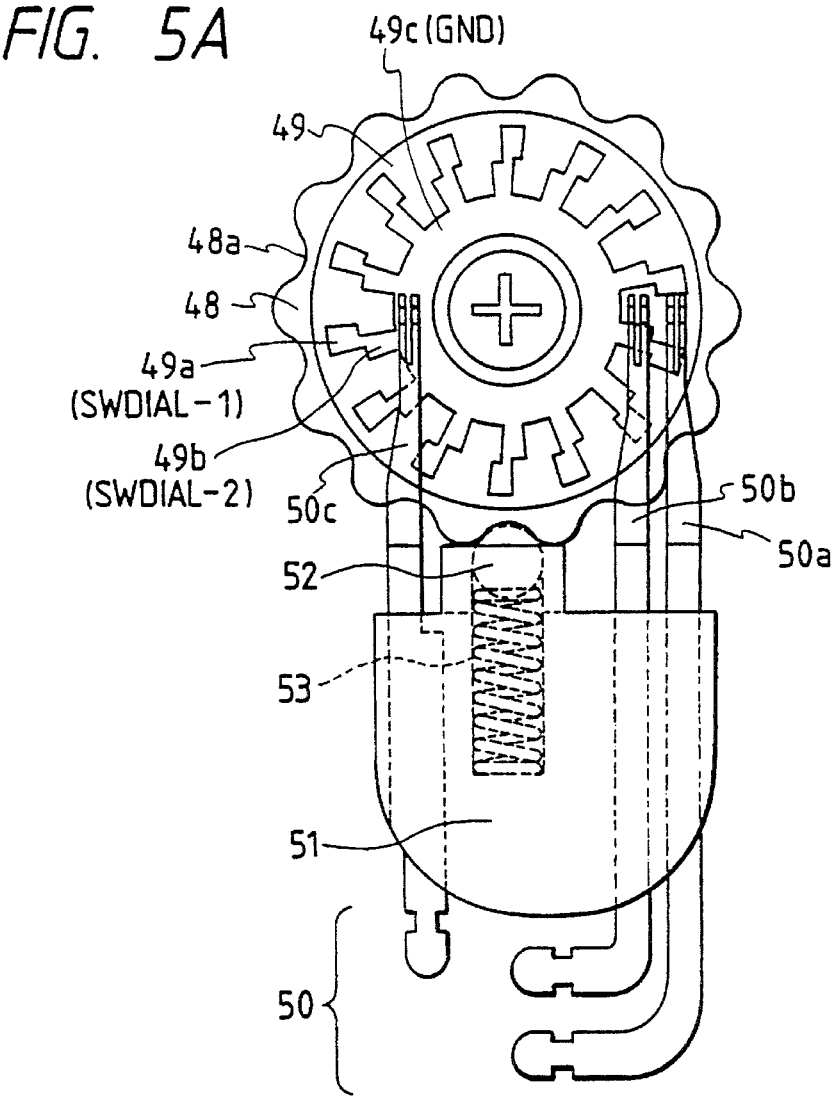
FIG.5B₁ SWDIAL 1 
FIG.5B₂ SWDIAL 2 
FIG.5B₃ SWDIAL 1 
FIG.5B₄ SWDIAL 2 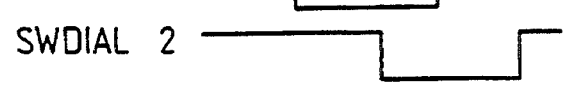

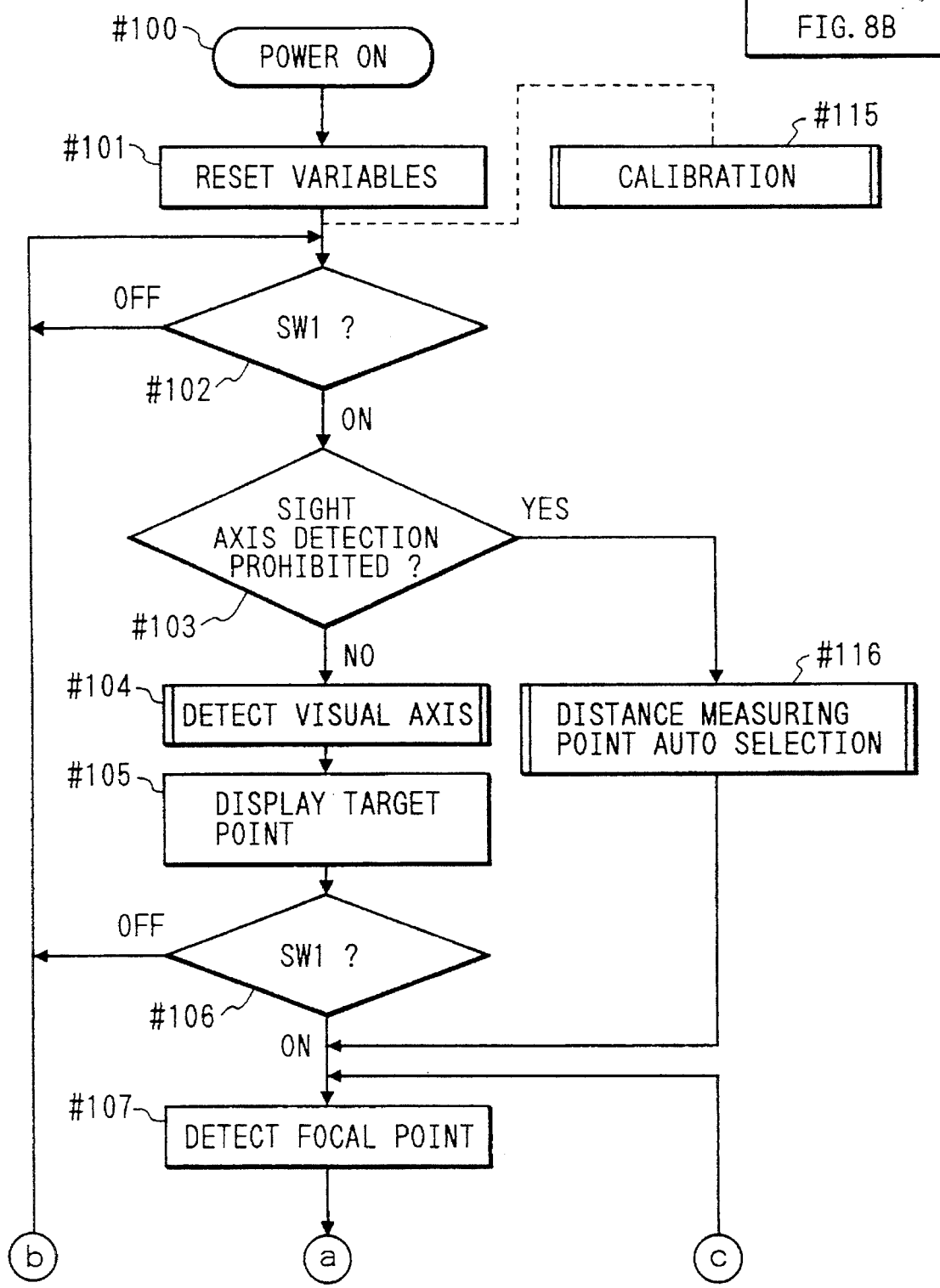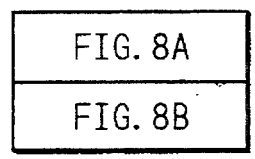

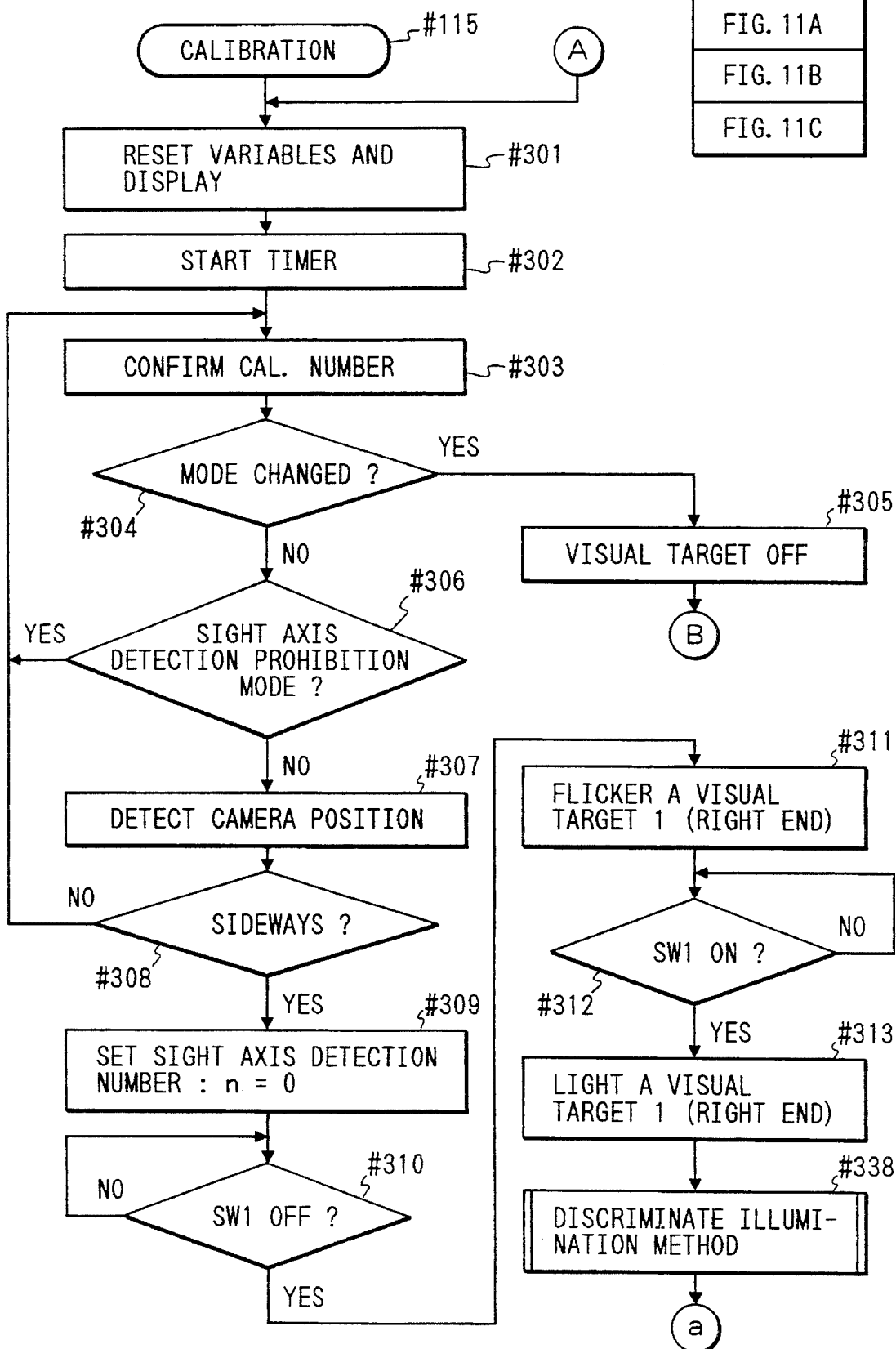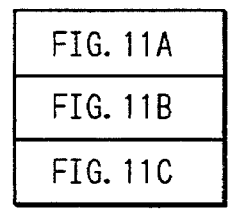

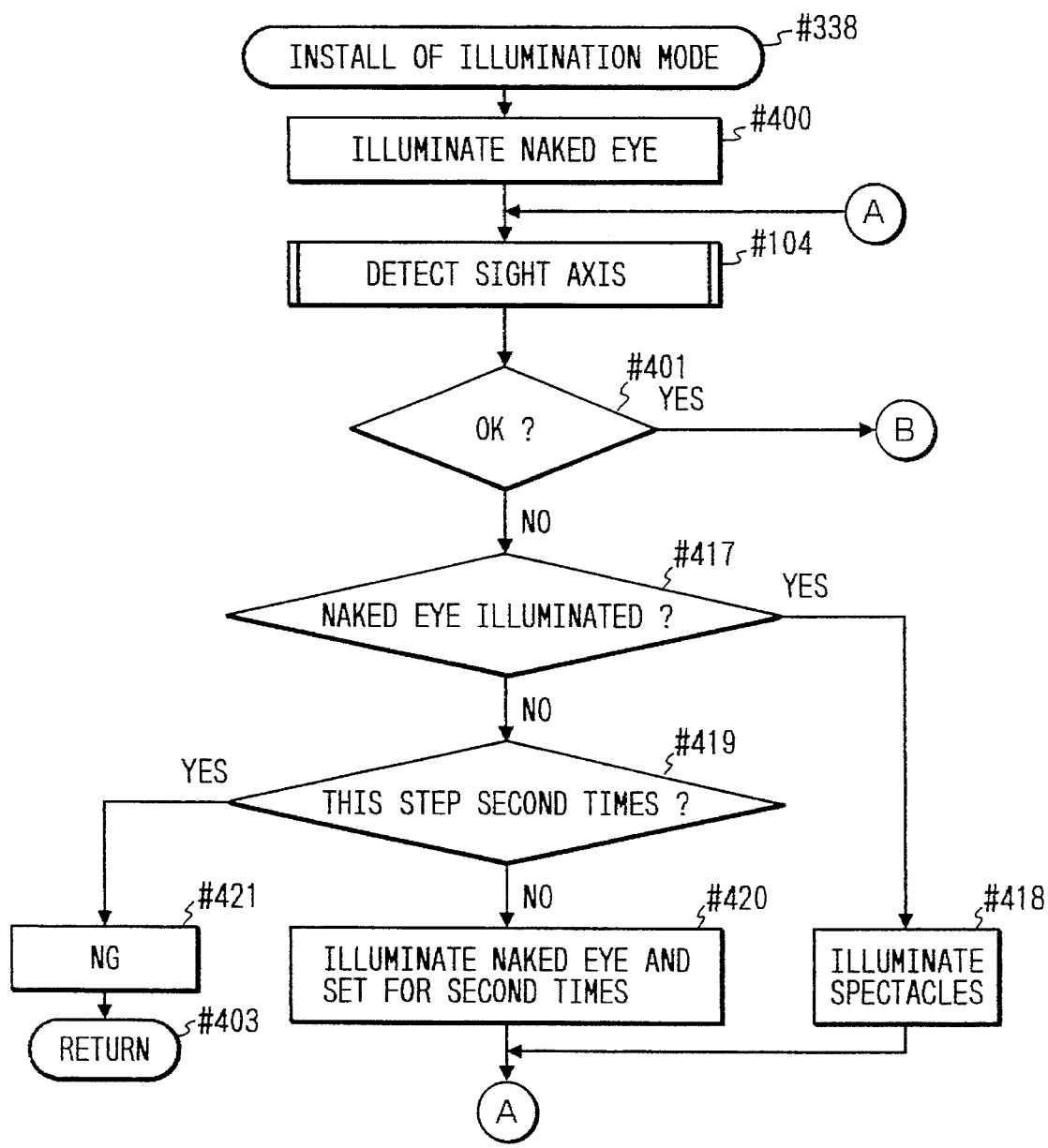

OPTICAL EQUIPMENT WITH DEVICE FOR DETECTING DIRECTION OF VISUAL AXIS

This application is a continuation of prior application Ser. No. 08/115,018 filed on Sep. 2, 1993, now abandoned.

BACKGROUND OF THE INVENTION

1. Field of the Invention

The present invention relates to an optical equipment, such as camera, equipped with a device for detecting the visual axis of the observer, observing an object through a view finder system of said equipment, utilizing a reflected image of the eyeball of said observer, obtained by illuminating said eyeball.

2. Related Background Art

There are already proposed various devices, such as eyeball camera, for detecting so-called visual axis of the observer, or detecting the position of observation of the observer within a plane to be observed. The method for detecting said visual axis, disclosed for example in the Japanese Patent Application Laid-open No. 1-274736 consists of projecting a light beam from a light source onto a front portion of the eyeball of the observer, and determining the visual axis by a reflected corneal image formed by the light reflected from the cornea and the focal position of the pupil.

FIG. 46 shows the basic principle of detecting the visual axis, wherein light source 13a, 13b, such as light-emitting diodes, emitting infrared light not visible to the observer, are positioned substantially symmetrically in the X-direction with respect to the optical axis of a light-receiving lens 12 and illuminate the eyeball of the observer with diverging light beams. A part of the illuminating light reflected by the eyeball is concentrated by the lens 12 onto an image sensor 14. FIG. 47A is a schematic view of the image of the eyeball projected on said image sensor 14, and FIG. 47B is a chart of the output intensity of said image sensor 14. The method of detection of visual axis will be explained in the following, with reference to these drawings.

The infrared light emitted from the light source 13b illuminates the cornea 16 of the eyeball 15 of the observer, and a reflected corneal image P1 (false image) formed by a part of the infrared light reflected on the surface of the cornea 16 is concentrated by the light-receiving lens 12 and is focused at a position Xp1 on the image sensor 14. Similarly the infrared light emitted from the light source 13a illuminates the cornea 16, and a reflected corneal image P2 formed by a part of the reflected infrared light is focused by the lens 12 onto a position Xp2 of the image sensor 14.

Also the light beams from end portions a, b of the iris 17 are guided through said lens 12 to form the images of said end portions a, b at positions Xa, Xb on the image sensor 14. If the rotation angle θ of the optical axis of the eyeball 15 is small with respect to the optical axis of the light-receiving lens 12, the coordinate Xc of the center c of the pupil 19 is represented as:

$$Xic = (Xa+Xb)/2.$$

Also since the coordinate x of the middle point of the corneal reflected images P1 and P2 substantially coincides with the x-coordinate $x_o$ of the center O of curvature of the cornea 16, the rotation angle $\theta_x$ of the optical axis of the eyeball 15 in the Z-X plane substantially satisfies a relation:

$$\beta*OC*SIN\theta X = (Xp1+Xp2)/2 - Xic \quad (1)$$

wherein OC is a standard distance between the center O of curvature of the cornea 16 and the center C of the pupil 19. β is a magnification determined by the position of the eyeball with respect to the lens 12 and is practically determined as a function of the distance |Xp1−Xp2| of the corneal reflected images, and * indicates multiplication.

These drawings illustrate the calculation of the rotation angle θx in case the eyeball of the observer rotates in the Z-X plane (for example horizontal plane), but the rotation angle θy in case of rotation in the Y-Z plane (for example vertical plane) can be calculated in a similar manner.

With such calculations of the rotation angles θx, θy of the optical axis of the eyeball of the observer, the position (X, Y) observed by the observer for example on a focal screen in a single lens reflex camera can be represented as:

$$X = m** (Ax*\theta x + BX) \quad (2)$$

$$Y = m*(Ay*\theta y + By) \quad (3)$$

wherein m is a constant, determined by the view finder system of the camera and used for converting the rotation angle into the coordinate on the focal screen. Also Ax, Ay, Bx, By are visual axis correcting coefficients for correcting the individual difference in the visual axis of the observer, and can be determined from the rotation angles of the eyeball obtained at observing two different targets.

Also the method of detecting the visual axis when the camera is in a vertically oblong position is already proposed, for example, in the Japanese Laid-Open Patent Application No. 3-107909. FIG. 48 is a partial schematic view (in the vicinity of the eyepiece lens of the view finder system) of an optical equipment provided with a visual axis detecting device proposed in said patent application.

As shown in this drawing, the light sources 13a, 13b are turned on in the normal camera position, and the light sources 13b, 13c are turned on in the vertically oblong position of the camera, with illumination through prisms, whereby the detection of visual axis is rendered possible in either position of the camera.

It is now assumed, as shown in FIG. 27, that two light-emitting elements (IRED) 201i, 201j for illuminating the eyeball of the observer are positioned symmetrically, in the horizontal position, with respect to a vertical plane containing the optical axis of the view finder system, when the camera 220 is in the normal position.

In such normal position of the camera 220, the corneal reflected images Pi, Pj formed by the illumination of the eyeball 15 of the observer by the IRED's 201i, 201j are focused on an image sensor provided in the camera 220, so that said two corneal reflected images can both be easily detected.

FIG. 28 is a schematic view showing the relationship between the two corneal reflected images Pi, Pj and the eyeball, wherein shown also are an eyelid 222 and eyelashes 223.

However, let us consider a situation shown in FIG. 29, in which the camera is held in a vertically oblong position, with the shutter releasing button 241 at the top. In such situation, as shown in FIG. 30, the two corneal reflected images Pi, Pj are aligned perpendicularly to the eyelid 222, so that a reflected image Pj is often eclipsed by the eyelid 222 and eyelashes 223 of the observer. Particularly under outdoor daylight, the eyelid is somewhat closed because of the high illumination intensity, so that the probability of eclipse of one of the corneal reflected images becomes extremely high. On the other hand, if the camera is in the vertically oblong position, with the shutter releasing button 241 closer to the ground, the other reflected image Pi tends to be eclipsed.

Therefore, in the above-explained conventional device in consideration of the vertical camera position, the position of illumination is so switched that two corneal reflected images are formed parallel to the eyelid, in the vertical or horizontal camera position.

When the observer supports the camera in standing position, satisfactory reflected images Pn, Pk can be obtained as shown in FIG. 33 when the shutter releasing button 241 is positioned closer to the ground. On the other hand, in the normal camera position or in the vertical camera position with the shutter releasing button close to the top, the illumination is made from the side of the upper eyelid of the observer, so that the two corneal reflected images are often eclipsed by the eyelid 222 or the eyelashes 223 as shown in FIGS. 31 or 32, whereby the detection of visual axis becomes difficult.

Also the present applicant already disclosed, in the Japanese Patent Application Laid-open No. 4-138432, an optical equipment with visual axis detecting means provided with means for discriminating whether the observer looking into the view finder wears spectacles, from the ghost of the eyeball illuminating light, reflected by the spectacles.

However, if an observer not wearing the spectacles is positioned close to the view finder, there will result strong reflected light from the eyelid or the eyelashes, and such reflected light may be recognized as ghost and the observer may be misidentified as wearing the spectacles. As a result, an observer without spectacles may be given illumination designed for the observer with spectacles, so that the precise visual axis detection may become impossible.

Also if an observer wearing the spectacles is positioned close to the view finder, the light reflected by the spectacles does not enter the visual axis detecting optical system, so that the ghost is not generated and the observer may be misidentified as not wearing the spectacles. As a result, the observer with the spectacles is given the illumination designed for the observer without the spectacles, whereby the visual axis detection may become impossible.

SUMMARY OF THE INVENTION

A principal object of the present invention is, in an optical equipment in which an eyeball of the photographer is illuminated artificially, then the direction of visual axis (or watched point) of the photographer is detected from the reflected light from the eyeball and the detected information is used for functional control, to achieve illumination of the eyeball in satisfactory state regardless of the state of use such as the mode of use of the optical equipment (such as vertical or horizontal position), or whether the photographer wears the spectacles or not.

A second object of the present invention is to provide an optical image taking apparatus provided with a visual axis detecting device, in which plural light-emitting elements for illuminating the eyeball of the observer are so appropriately positioned that at least two corneal reflected images of said light-emitting elements are always satisfactorily formed on photosensor means regardless whether the image taking apparatus is held by the observer in a normal position, or in a vertical position in which an image taking button is positioned on the top or close to the ground.

On the other hand, in the conventional visual axis detecting device, there are detected the positions of two corneal reflected images generated by paired two light-emitting elements, in order to determine the distance of the device and the eyeball (in fact the optical distance to the imaging lens) and the center O of curvature of the cornea.

However, in case the eyeball of the observer looking at an object is positioned distant from the device, for example because the observer wears the spectacles, said two corneal reflected images become positioned mutually close, so that the positions thereof cannot be precisely detected by the aberration of the optical system or by the resolving power of the image sensor, whereby the precision of visual axis detection may be detrimentally affected.

For avoiding such drawback, there can be conceived to increase the mutual distance of the light-emitting elements, but, in such case, if the eyeball is positioned close to the device, the corneal reflected images are formed in the aspherical area around the cornea, so that the precision of visual axis detection is again undesirably affected.

Also if the observer wears the spectacles, the light illuminating the eyeball is strongly reflected by the spectacles, thus significantly affecting the information of the eyeball required for the visual axis detection, whereby the detection of visual axis is hindered with a high probability.

A third object of the present invention is to provide a visual axis detecting device capable of detecting the visual axis of the observer with high precision, regardless of the variable distance of the eyeball of the observer to the device and whether the observer wears the spectacles or not, by suitable positioning and adjustment of light-emitting state of the plural light-emitting elements constituting the illuminating means for illuminating the eyeball of the observer, and an optical equipment provided with such device.

A fourth object of the present invention is, in an optical apparatus provided with a visual axis detecting device comprising illumination means for illuminating the eyeball of the observer, light reception means for receiving the light reflected from the frontal portion of the eyeball of the observer, and calculation means for calculating the visual axis of the observer from the image of eyeball obtained by said light-receiving means, to detect the presence of ghost by said calculation means in the eyeball image received by said light-receiving means and to discriminate whether the observer wears the spectacles by the presence or absence of ghost and the distance of the eyeball of the observer to said visual axis detecting device, thereby improving the precision of discrimination whether the observer wears the spectacles and achieving high precise detection of the visual axis.

BRIEF DESCRIPTION OF THE DRAWINGS

FIG. 3 is a view of the viewing field of a view finder;

FIGS. 5A and 5B are views showing details of an electronic dial;

FIG. 7A is a view of monitoring LCD's when all the segments are turned on;

FIG. 7B is a view of LCD's in the view finder when all the segments are turned on;

DETAILED DESCRIPTION OF THE PREFERRED EMBODIMENTS

Figure 1:
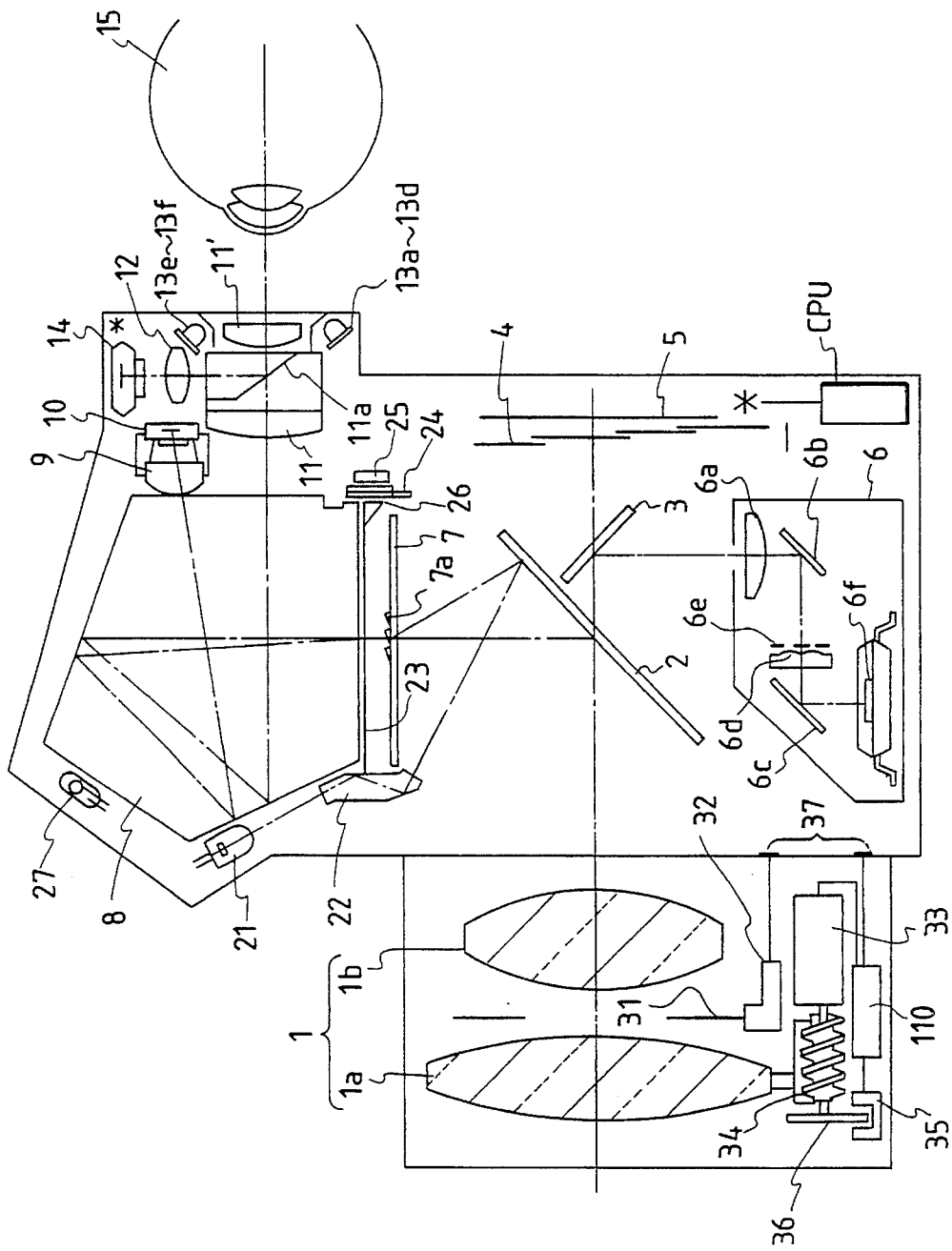
FIG. 1 is a schematic view of a single lens reflex camera.
Figure 2A:
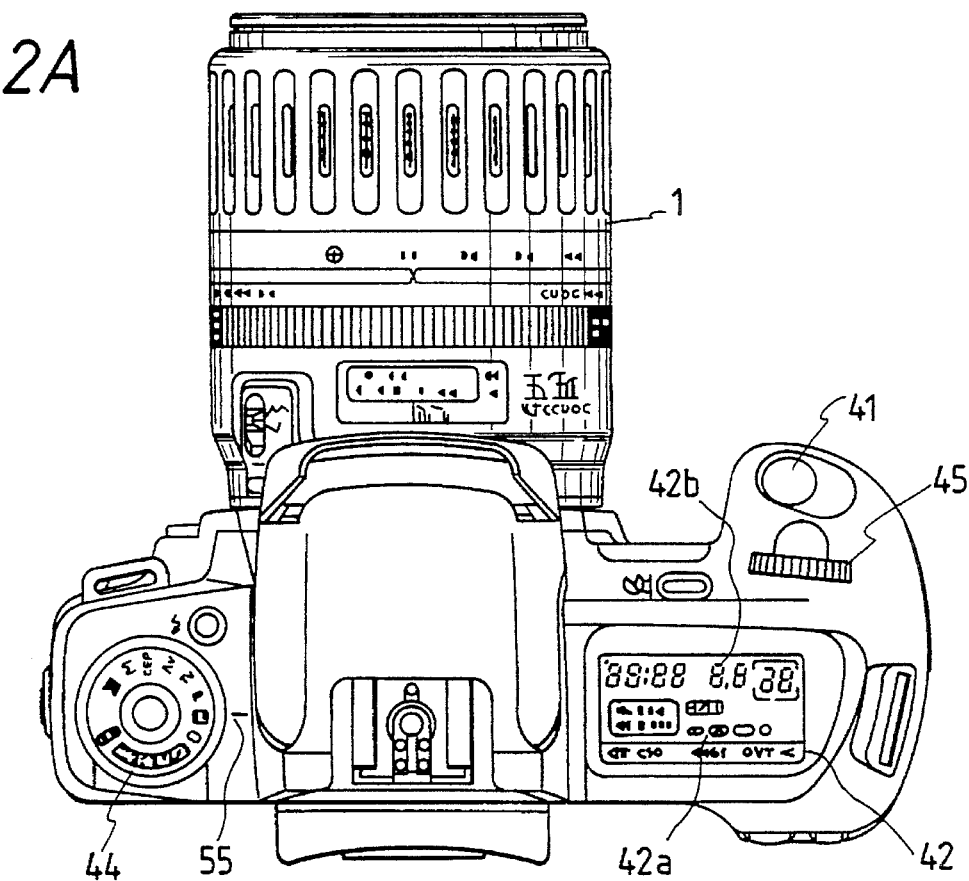
FIG. 2A is an upper view of a single lens reflex camera.
Figure 2B:
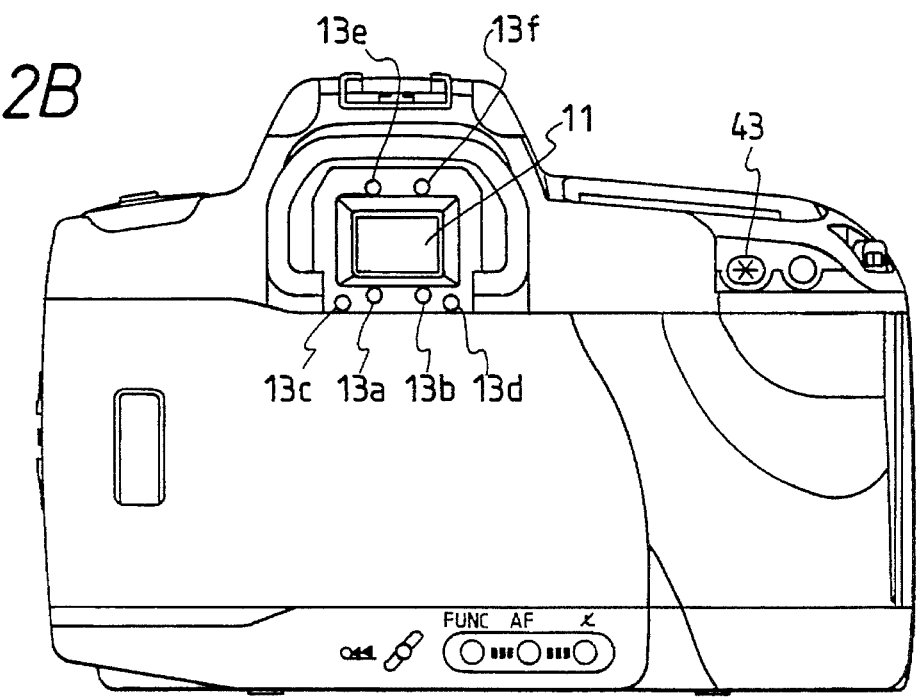
FIG. 2B is a rear external view thereof.

FIGS. 1 to 19 illustrate embodiments of the present invention, wherein FIG. 1 is a schematic view of a single lens reflex camera embodying the present invention, FIG. 2A is an external plan view of said camera, FIG. 2B is a rear view thereof, and FIG. 3 is a view of the viewing field of the view finder thereof. In the following there will be given an explanation on the basic configuration, and then on the features of the embodiments with reference to FIG. 19 and ensuing drawings.

(Description of basic configuration)

In the following drawings there are shown a phototaking lens 1, which is illustrated with two lenses for the ease of understanding but in practice is composed of a larger number of lenses as already known; a main mirror 2 which is diagonally positioned in the phototaking optical path or retracted therefrom respectively in the observing state or in the phototaking state; a sub mirror 3 for reflecting the light beam, transmitted by the main mirror 2, downward toward a lower part of the camera body; a shutter 4; a photosensitive member 5 which is a silver halide-based film or a solid-state image pickup device such as a CCD or a MOS image pickup device, or a image pickup tube such as a vidicon; a focus state detecting device 6 of the known phase difference system, composed of a field lens 6a positioned close to the focal plane, mirrors 6b, 6c, a secondary imaging lens 6d, a diaphragm 6e, a line sensor 6f consisting of plural CCD's etc., for detecting the focus state in plural areas (five areas) in the viewing field as shown in FIG. 3; a focal screen 7 positioned at the anticipated focal plane of the phototaking lens 1; a pentagonal roof-shaped prism 8 for varying the optical path of the view finder; and an imaging lens 9 and a divided photosensor 10 for measuring the luminance of the object in the viewing field, wherein the focal screen 7 and said photosensor are mutually conjugate with respect to said imaging lens 9, through the reflected optical path in the pentagonal prism 8.

Behind the pentagonal roof-shaped prism 8 there are provided a beam splitter 11 with a light splitting plane 11a and an eyepiece lens 11' for observation of the focal screen 7 by the eyeball 15 of the photographer. The beam splitting plane 11a is, for example, a dichroic mirror transmitting the visible light and reflecting the infrared light. An image sensor 14, consisting of a two-dimensional array of photosensor elements such as CCD, is so positioned as to be substantially conjugate with the pupil of the eyeball 15 of the photographer, positioned in a predetermined manner with respect to the light-receiving lens 12. Infrared light-emitting diodes 13a–13f, constituting light sources, are positioned around the eyepiece lens 11, as shown in FIG. 2B.

A high-intensity LED 21 recognizable even among objects of high luminance, emits light which is reflected by a light projecting prism 22 and the main mirror 2, is further deflected perpendicularly by a small prism array 7a provided in a display area of the focus screen 7, and reaches the eyeball of the photographer through the pentagonal prism 8 and the eyepiece lens 11. Corresponding to the focus state detecting areas of the focal screen 7, there are formed said small prism arrays 7a in a frame shape, and said areas are respectively illuminated by five superimposing LED's 21 (LED-L1, LED-L2, LED-C, LED-R1 and LED-R2). As shown in FIG. 3, the marks 200, 201, 202, 203, 204 for the distance measuring points are lighted to indicate the area of focus state detection (hereinafter called superimposed display). Inside the distance measuring marks 200, 204 at the left and right ends, there are formed dot marks 205, 206 which constitute, as will be explained later, viewing marks for obtaining visual axis correcting coefficients for correcting the detection error in the visual axis, resulting from individual difference in the eyeball (said correcting operation being hereinafter called calibration). There are further provided a viewing field mask 23, defining the viewing field of the view finder; an in-finder LCD 24 for displaying phototaking information in an area outside the viewing field, illuminated by an illuminating LED 25 (F-LED) whereby the transmitted light is guided by a triangular prism 26 into the view finder and displayed outside the viewing field as indicated by 207 in FIG. 3; and a known mercury switch 27 for detecting the camera position.

There are further provided a diaphragm 31 provided in the phototaking lens 1; a diaphragm driving device 32 including a diaphragm driving circuit 111 to be explained later; a lens driving motor 33; a lens driving member 34 consisting of driving gears etc.; a photocoupler 35 for detecting the rotation of a pulse disk 36 linked with the lens driving member 34 and transmitting the detected information to a focusing circuit 110, which drives the lens driving motor based on said information and the information on the lens driving amount from the camera, thereby moving the phototaking lens 1 to the focused position; and a known mount contact 37 constituting an interface between the camera and the lens.

Figure 4A:
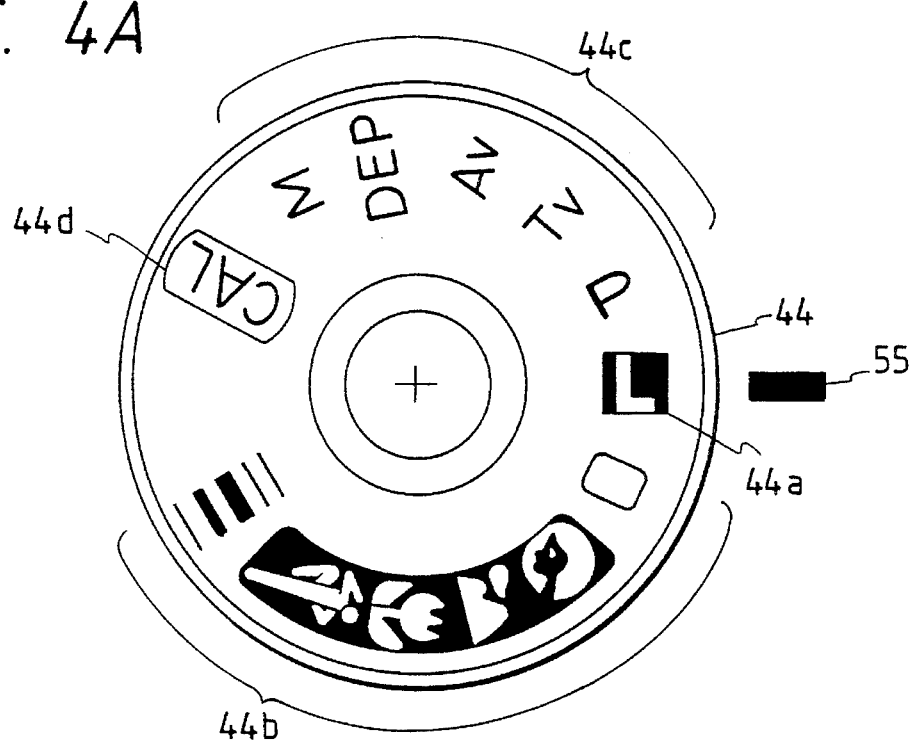
FIGS. 4A and 4B are views showing details of a mode dial.
Figure 4B:
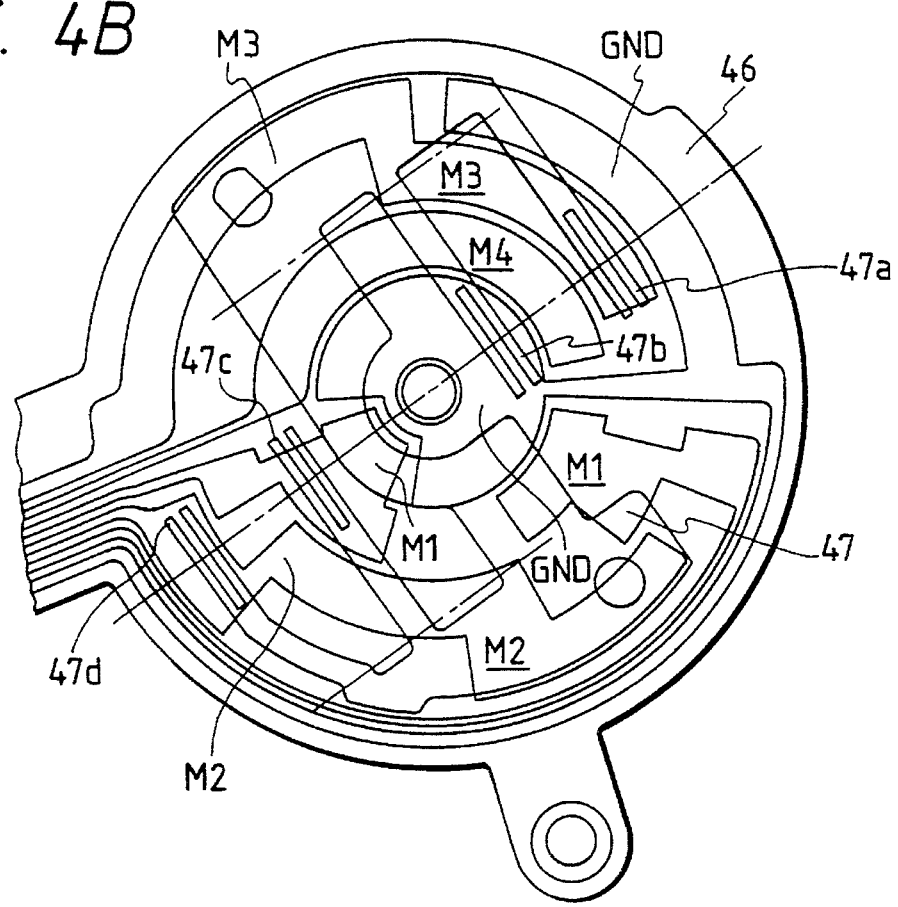

Referring to FIG. 2, there are shown a shutter release button 41; a monitor LCD 42 constituting an external monitor display and consisting of a fixed segment display unit 42a for displaying predetermined patterns and a 7-segment display unit 42b for displaying variable numbers; an AE lock button 43 for retaining the measured light value; and a mode dial 44 for selecting the phototaking modes. Other components will not be explained since they are unnecessary for the understanding of the present invention. FIGS. 4A and 4B show the details of said mode dial 44, wherein the phototaking mode is selected by matching a corresponding mark with an index 55 formed on the camera body. There are shown a lock position 44a for deactivating the camera; a position 44b for the automatic phototaking mode in which the camera is controlled according to a predetermined phototaking program; manual phototaking mode positions 44c, including the modes of program AE, shutter preferential AE, diaphragm preferential AE, depth-of-focus preferential AE and manual exposure, in which the photographer can set the phototaking data; and a CAL position 44d for selecting a calibration mode for calibrating the visual axis, as will be explained later. FIG. 4B shows the internal structure of said mode dial, wherein a flexible printed circuit board 46 bears switch patterns M1, M2, M3, M4 and a ground pattern GND as illustrated and is in sliding contact with four contacts 47a, 47b, 47c, 47d of a contact member 47 linked with the mode dial whereby 13 positions indicated on the mode dial 44 can be selected in four bits.

An electronic dial 45, capable of generating clock pulses upon rotation, is used for selecting a set value within the mode selected by the mode dial. For example, if the shutter preferential mode is selected by the mode dial 44, the currently selected shutter speed is displayed on the in-finder LCD 24 and on the monitoring LCD 42, and, in response to the rotation of the electronic dial 45 by the photographer, the shutter speed varies in succession from the currently selected value, according to the direction of rotation. FIGS. 5A and 5B illustrate the details of said electronic dial, wherein a click plate 48 rotating together with the dial 45 bears a printed circuit board 49. Said board 49 bears switch patterns 49a (SWDIAL-1), 49b (SWDIAL-2) and a ground pattern GND 49c, while a contact member 50 having three sliding contacts 50a, 50b, 50c is fixed on a fixed member 51. A click ball 52 engaging with one of the recesses 48a formed on the external periphery of the click plate 48 is biased by a coil spring 43 supported by the fixed member 51. In an ordinary position, in which the click ball 52 engages with one of the recesses 48a, the sliding contacts 50a, 50b do not touch either of the switch patterns 49a, 49b. If the photographer turns such electronic dial clockwise in FIGS. 5A and 5B, at first the sliding contact 50a touches the switch pattern 49b and then the switch pattern 49a, thereby counting up the set value. In case of an anticlockwise rotation, the relation between the sliding contacts and the switch patterns is inversed, whereby the set value is counted down in similar timings. FIG. 5B is a timing chart showing the pulse signals generated by the switch patterns 49a, 49b when the dial is rotated. The upper and lower halves respectively indicate the signals generated by clockwise or anticlockwise rotation of the dial by a click, and the timing of up/down counting and the rotating direction are detected in this manner.

Figure 6:
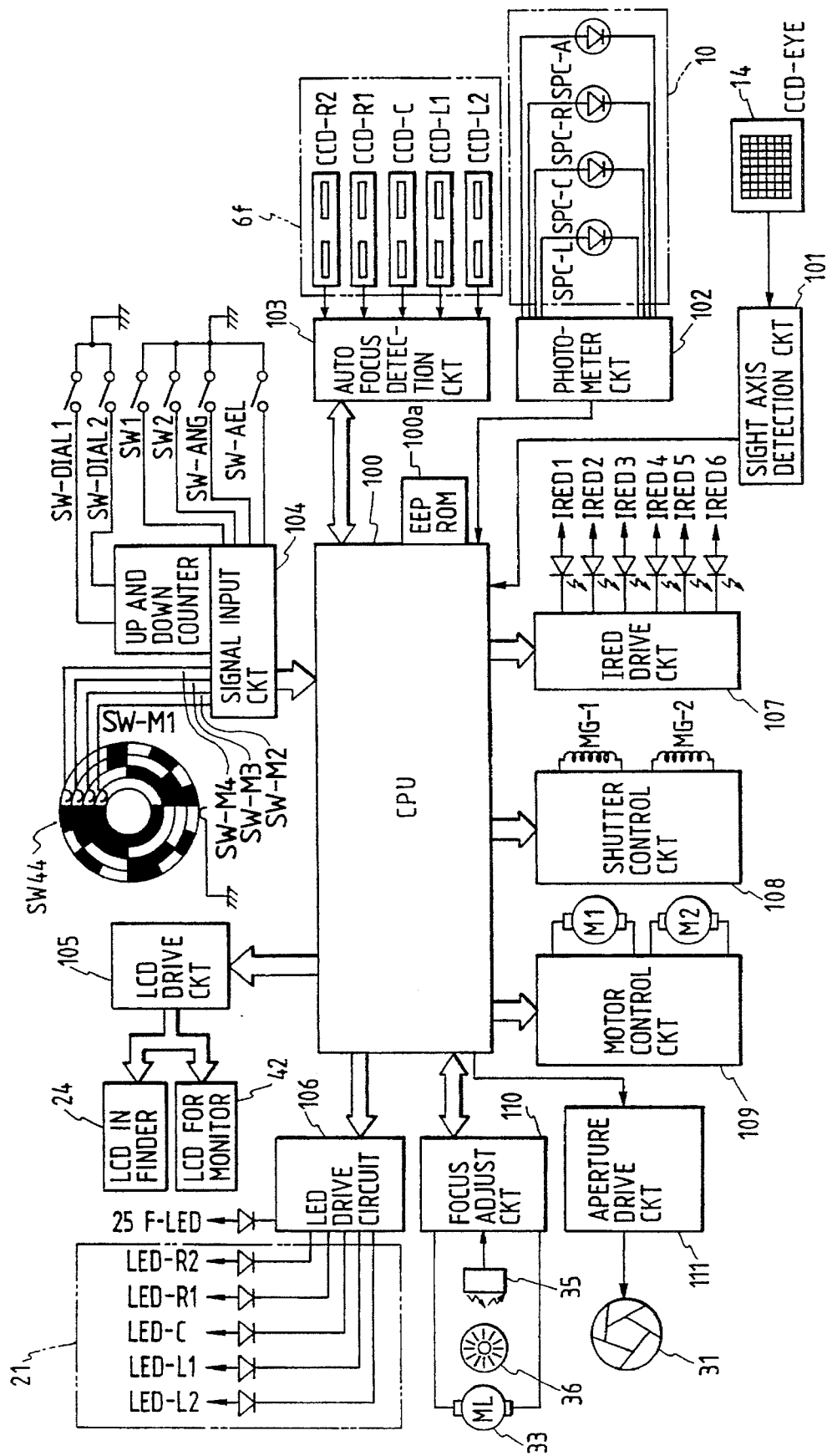
FIG. 6 is a block diagram of the electrical circuits of a camera.

FIG. 6 is a block diagram of the electrical circuits incorporated in the camera, wherein same components as those in FIG. 1 are represented by same numbers. A central processing unit (CPU) 100 composed of a microcomputer incorporated in the camera body is connected to a visual axis detecting circuit 101, a light metering circuit 102, an auto focus detecting circuit 103, a signal input circuit 104, an LCD driving circuit 105, an LED driving circuit 106, an IRED driving circuit 107, a shutter control circuit 108, and a motor control circuit 109. Signal transmission to a focusing circuit 110 and a diaphragm driving circuit 111, both provided in the phototaking lens, is achieved through the mount contacts 37 shown in FIG. 3.

An EEPROM 100a, attached to the CPU 100, serves to store correction data, for calibrating the individual difference in the visual axis. By matching the CAL position of the mode dial 44 with the index mark, there can be selected the calibration mode for obtaining the visual axis correcting coefficients (hereinafter called calibration data) for calibrating the individual difference of the visual axis, and the electronic dial 45 may be used for selecting calibration number corresponding to the calibration data, turning off the calibration, or setting a mode for inhibiting the detection of visual axis. There can be set plural calibration data, which can be used for different persons utilizing the same camera, or different states of observation of a same person, such as observations with and without spectacles or observations with and without the viewing power correcting lens. The selected calibration number or the set mode for inhibiting the visual axis detection is memorized by a calibration data number (1, 2, . . . or 0) in the EEPROM 100a, as will be explained later.

The visual axis detecting circuit 101 effects A/D conversion on the eyeball image obtained from the image sensor 14 (CCD-EYE), and sends the obtained image information to the CPU 100, which extracts feature points of the eyeball image, required for detecting the visual axis, according to a predetermined algorithm as will be explained later, and calculates the visual axis of the photographer from the positions of the feature points.

The light metering circuit 102 effects amplification, logarithmic compression and A/D conversion on the output of a light metering sensor 10, and sends the obtained luminance information of the sensors to the CPU 100. The light metering sensor 10 is composed of four photodiodes, namely SPC-L for measuring a left area 210 including the left-hand distance measuring points 200, 201 in the view finder frame shown in FIG. 3; SPC-C for measuring a central area 211 including the central distance measuring point 202; SPC-R for measuring a right area 212 including the right-hand distance measuring points 203, 204; and SPC-A for measuring a peripheral area 213. The line sensor 6f is a known CCD line sensor, consisting of 5 line sensors CCD-L2, CCD-L1, CCD-C, CCD-R1 and CCD-R2 corresponding, as explained before, to the five distance measuring points 200–204 in the view finder frame. The auto focus detecting circuit 103 effects A/D conversion on the voltages from said line sensor 6f, for supply to the CPU. There are also provided a light metering switch SW-1 to be turned on by a first stroke of the shutter release button 41 to initiate the light metering, auto focusing and visual axis detection; a shutter release switch SW-2 to be turned on by a second stroke of the shutter release button; a position detecting switch SW-ANG consisting of the mercury switch 27; an AE lock switch SW-AEL to be turned on by the depression of the AE lock button 43; dial switches SW-DIAL1, SW-DIAL2 provided in the aforementioned electronic dial and connected to an up/down counter in the signal input circuit 104 for counting the clicks of the electronic dial 45; and dial switches SW-M1–M4 provided in the mode dial. The signals of these switches are supplied to the signal input circuit 104 and are transmitted to the CPU 100 through a data bus. The LCD driving circuit 105 is a known circuit for driving the liquid crystal display LCD, and is capable of displaying the diaphragm aperture, shutter speed, selected phototaking mode etc. on the monitoring LCD 42 and the in-finder LCD 24, according to the signals from the CPU 100. The LED driving circuit 106 effects on/off control on the illuminating LED (F-LED) 22 and the superimposing LED 21. The IRED driving circuit 107 selectively turns on the infrared light-emitting diodes 13a–13f (IRED1–6). The shutter control circuit 108 controls magnets MG-1, MG-2 for respectively releasing the leading and trailing shutter curtains when energized, thereby providing the photosensitive member with a predetermined exposure. The motor control circuit 109 controls a motor M1 for advancing and rewinding the film and a motor M2 for charging the main mirror 2 and the shutter 4. The shutter releasing sequence of the camera is executed by said shutter control circuit 108 and motor control circuit 109.

Figure 7A:
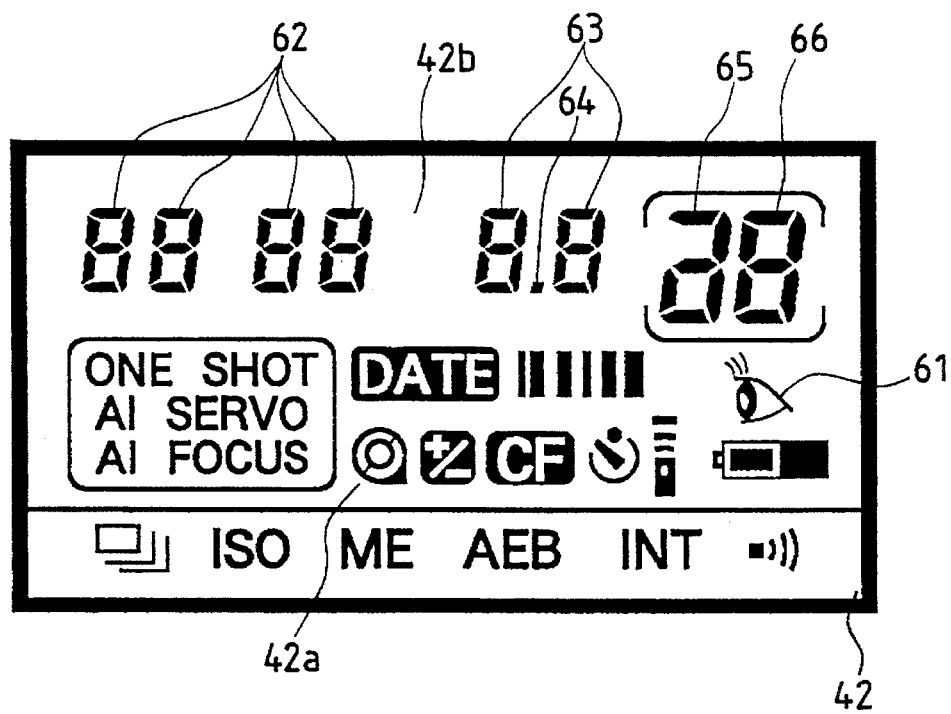
Figure 7B:
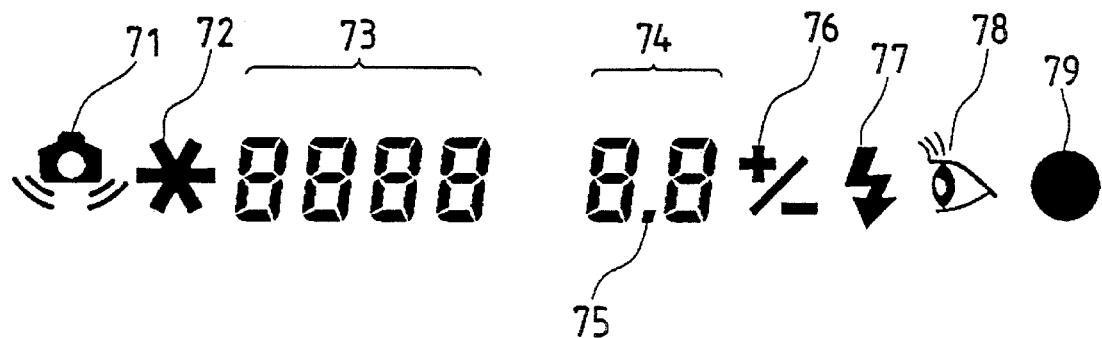

FIGS. 7A and 7B illustrate all the display segments of the monitoring LCD 42 and the in-finder LCD 24. Referring to FIG. 7A, in a fixed display segment area 42a, there is provided, in addition to the already known displays for phototaking modes, a visual axis input mode display 61 indicating that the visual axis detection is executed and the phototaking operation of the camera such as the auto focusing operation or the selection of phototaking mode is controlled by the visual axis information. A 7-segment display area 42b for displaying variable numbers is composed of 4-digit display 62 for indicating the shutter speed, a 2-digit display 63 and a decimal point 64 for displaying the diaphragm aperture, and limited number displaying segments 65 and a 1-digit 7-segment display 66 for displaying the film frame number. In FIG. 7B there are shown a hand vibration warning mark 71, an AE lock mark 72, 7-segment displays 73, 74, 75 for displaying the shutter speed and the diaphragm aperture as explained above, an exposure correction mark 76, a flash charging completion mark 77, a visual axis input mark 78 indicating the visual axis input state, and an in-focus mark 79 indicating the in-focus state of the phototaking lens 1.

In the following there will be explained the function of the camera provided with the visual axis detecting device, with reference to a flow chart shown in FIG. 8 and also to FIGS. 12A to 12E illustrating the display states in the view finder.

When the camera is shifted from the deactivated state to a certain phototaking mode (in the present embodiment there will be explained the case of shutter preferential AE mode) by the rotation of the mode dial 44, the power supply of the camera is turned on (#100), and the variables used for visual axis detection, other than the calibration data, stored in the EEPROM of the CPU 100 are reset (#101). Then the camera waits until the switch SW1 is turned on by the depression of the shutter release button 41 (#102). When the signal input circuit 104 detects that the switch SW1 is turned on by the depression of said button 41, the CPU 100 confirms, from the visual axis detecting circuit 101, the calibration data to be used in the visual axis detection (#103). If the calibration data corresponding to thus confirmed calibration number have not been varied from the initial values, or if the visual axis detection inhibiting mode has been selected, a distance measuring point is selected by an automatic distance measuring point selecting subroutine (#116) without executing the visual axis detection, namely without employing the visual axis information. The auto focus detecting circuit 103 executes the focus state detection on said distance measuring point (#107). There can be conceived certain algorithms for such automatic distance measuring point selection, but effective is a near point preferential algorithm with weighting at the central distance measuring point, which is exemplified in FIG. 9 and will be explained later.

Figure 12A:
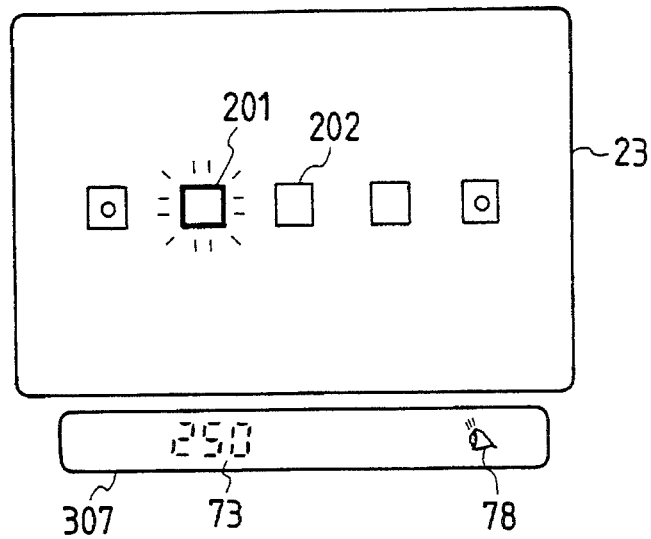
FIGS. 12A to 12E are views showing displays in the view finder during the function of the camera.

On the other hand, if it is recognized that the calibration data for the visual axis corresponding to the aforementioned calibration data number has been set at a certain value entered by the photographer, the visual axis detecting circuit 101 executes the visual axis detection according to said calibration data (#104). In this state the LED driving circuit 106 turns on the illuminating LED (F-LED) 24, while the LCD driving circuit 105 turns on the visual axis input mark 78 of the in-finder LCD 24, whereby the photographer can confirm, by the display 207 outside the view finder frame, that the camera is executing the visual axis detection (FIG. 12A). Also the 7-segment display 73 displays a set shutter speed (in this embodiment there is shown a case of shutter preferential AE mode with a shutter speed of 1/250 sec.).

Figure 12B:
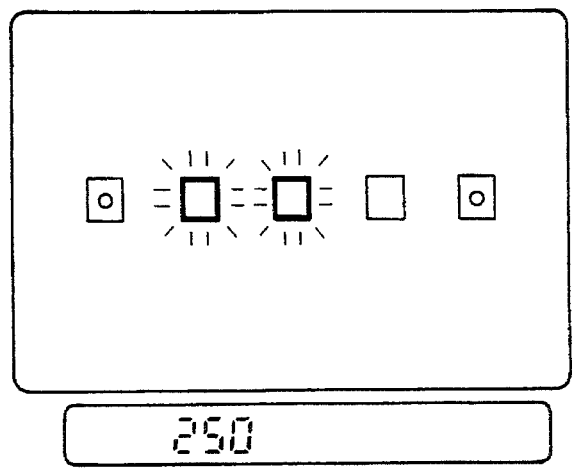
Figure 12C:
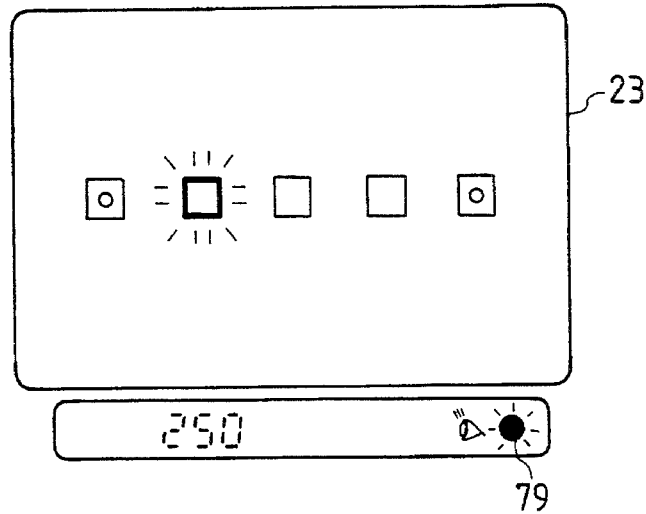

The visual axis detected by the visual axis detecting circuit 101 is converted into the coordinate of watched point on the focus screen 7. The CPU 100 selects a distance measuring point close to said watched point, and sends a signal to the display circuit 106 for flashing the mark of said distance measuring point by the superimposing LED 21 (#105). FIGS. 12A and 12C illustrate, as an example, a state in which the mark 201 is selected. If the reliability of the coordinate of the watched point detected by the circuit 101 is low, the CPU 100 sends the signal so as to vary the number of selected distance measuring points according to the level of said reliability. FIG. 12B shows a state in which the reliability is lower than that in FIG. 12B whereby the distance measuring points 201, 202 are selected. The photographer observes the distance measuring point selected according to the visual axis of the photographer, and, if he decides that said point is improper and turns off the switch SW1 by lifting his finger from the shutter release button 41 (#106), the camera waits until the switch SW1 is turned on (#102).

Figure 12D:
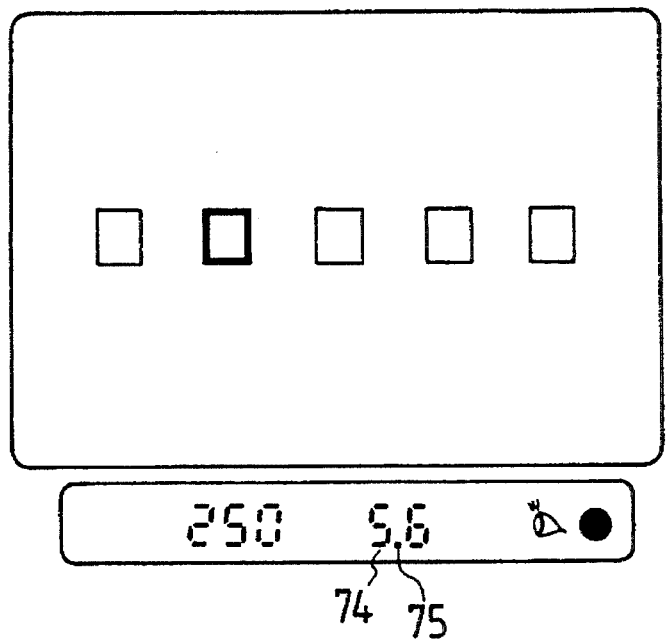

If, after observing the distance measuring point selected according to the visual axis, the photographer continues to turn on the switch SW1 (#106), the auto focus detecting circuit 103 executes focus state detection on at least one distance measuring point, utilizing the detected visual axis information (#107). Then there is discriminated whether the distance measurement is possible with the selected distance measuring point (#108), and, if impossible, the CPU 100 sends a signal to the LCD driving circuit 105 to intermittently turn on the in-focus mark 79 in the in-finder LCD 24, thereby informing the photographer of the improper distance measurement (#118) (FIG. 12C) until the switch SW1 is turned off (#119). On the other hand, if the distance measurement is possible and if the focusing state of the distance measuring point selected by the predetermined algorithm is not in focus (#109), the CPU 100 sends a signal to the focusing circuit 110 to drive the phototaking lens 1 by a predetermined amount (#117). After said lens driving, the auto focus detecting circuit 103 detects the focus state again (#107) to discriminate whether the phototaking lens 1 is in focus (#109). If the phototaking lens 1 is in focus at the selected distance measuring point, the CPU 100 sends a signal to the LCD driving circuit 105 to turn on the in-focus mark 79 in the in-finder LCD 24 and also a signal to the LED driving circuit 106 to provide an in-focus display on the in-focus distance measuring point 201 (#110) (FIG. 12D). In this state, the flashing display of the aforementioned distance measuring point, selected by the visual axis, is turned off, but, since the distance measuring point with in-focus display often coincides with the point selected by the visual axis, the in-focus distance measuring point is continuously turned on in order to inform the photographer of the in-focus state. The photographer observes the focused distance measuring point displayed in the view finder, and, if he decides that said distance measuring point is improper and turns off the switch SW1 by lifting his finger from the shutter release button 41 (#111), the camera waits until the switch SW1 is turned on (#102). If, after observing the distance measuring point with in-focus display, the photographer continues to turn on the switch SW1 (#111), the CPU 100 sends a signal to the light metering circuit 102 to execute the light metering (#112). In this state the exposure value is calculated with weighting on the light metering areas 210–213, including the focused distance measuring point. In the present embodiment, there is executed a known calculation with weighting on the light metering area 210 including the distance measuring point 201, and, as a result, a diaphragm aperture (F5.6) is displayed with the 7-segment display 74 and the decimal point 75 (FIG. 12D). Then there is discriminated whether the switch SW2 is turned on by the depression of the shutter release button 41 (#113), and, if not, the state of the switch SW1 is confirmed again (#111). If the switch SW2 is turned on, the CPU 100 sends signals to the shutter control circuit 108, motor control circuit 109 and diaphragm driving circuit 111. At first the motor M2 is energized to lift the mirror 2, then the diaphragm 31 is closed down, and the magnet MG1 is energized to release the leading curtain of the shutter 4. The aperture of the diaphragm 31 and the speed of the shutter 4 are determined from the exposure value detected by said light metering circuit 102 and the sensitivity of the film 5. After a predetermined shutter time (1/250 sec.), the magnet MG2 is energized to release the trailing curtain of the shutter 4. After the completion of exposure to the film 5, the motor M2 is energized again to lower the mirror, and to charge the shutter. At the same time the motor M1 is also energized to advance the film by a frame, whereby the shutter releasing sequence is terminated (#114). Thereafter the camera waits again until the switch SW1 is turned on (#102).

Figure 8B:
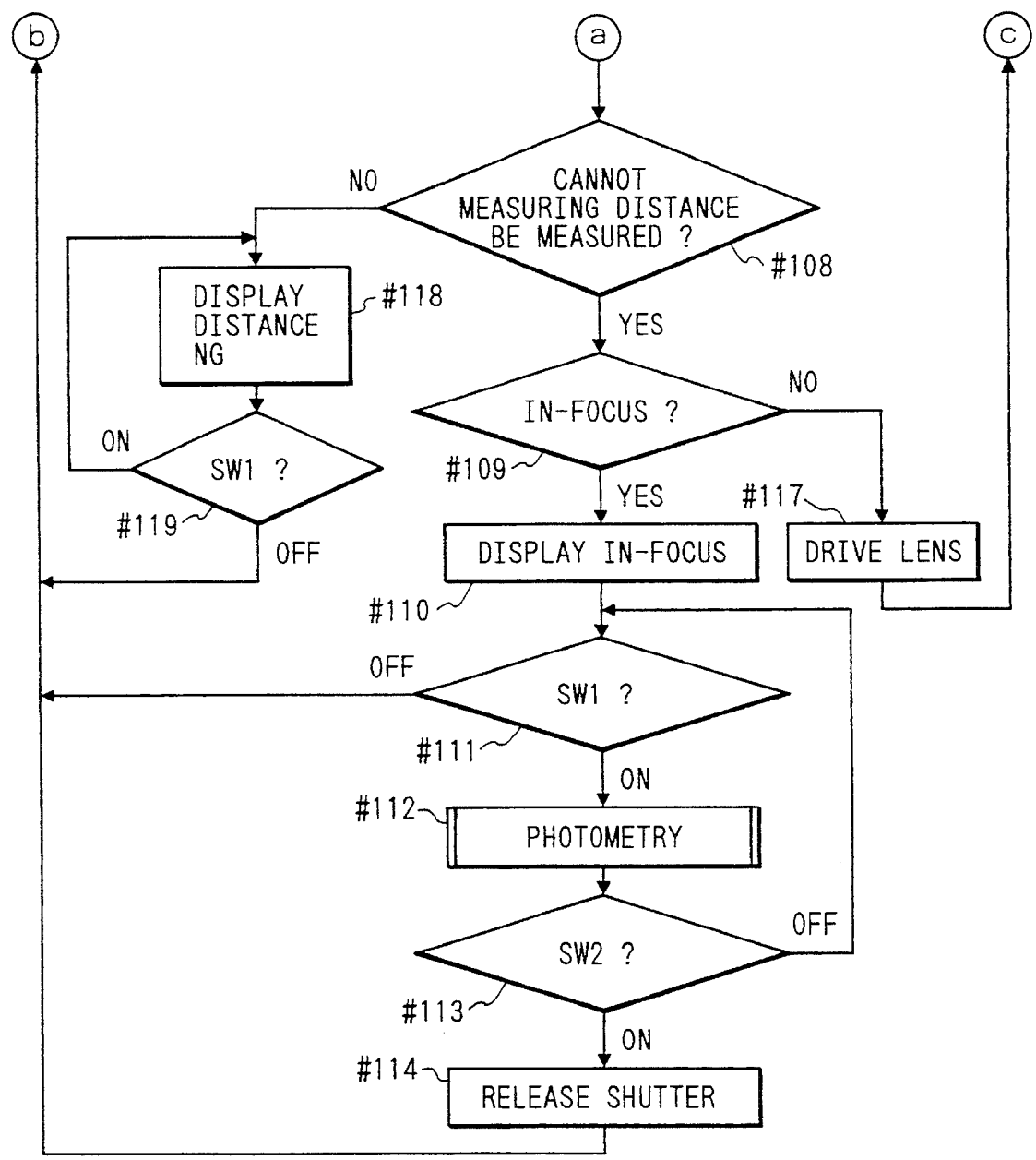
FIG. 8, comprised of FIGS. 8A and 8B, is a flow chart showing the operation sequence of a camera.

If the signal input circuit 104 detects that the mode is varied to the visual axis calibration mode by the mode dial 44 in the course of a serial operation, other than the shutter releasing operation (#114) shown in FIG. 8, the CPU 100 interrupts the camera operation and sends a signal to the visual axis detecting circuit 101 thereby setting a state enabling the visual axis calibration (#115). The method of visual axis calibration will be explained later.

Figure 9:
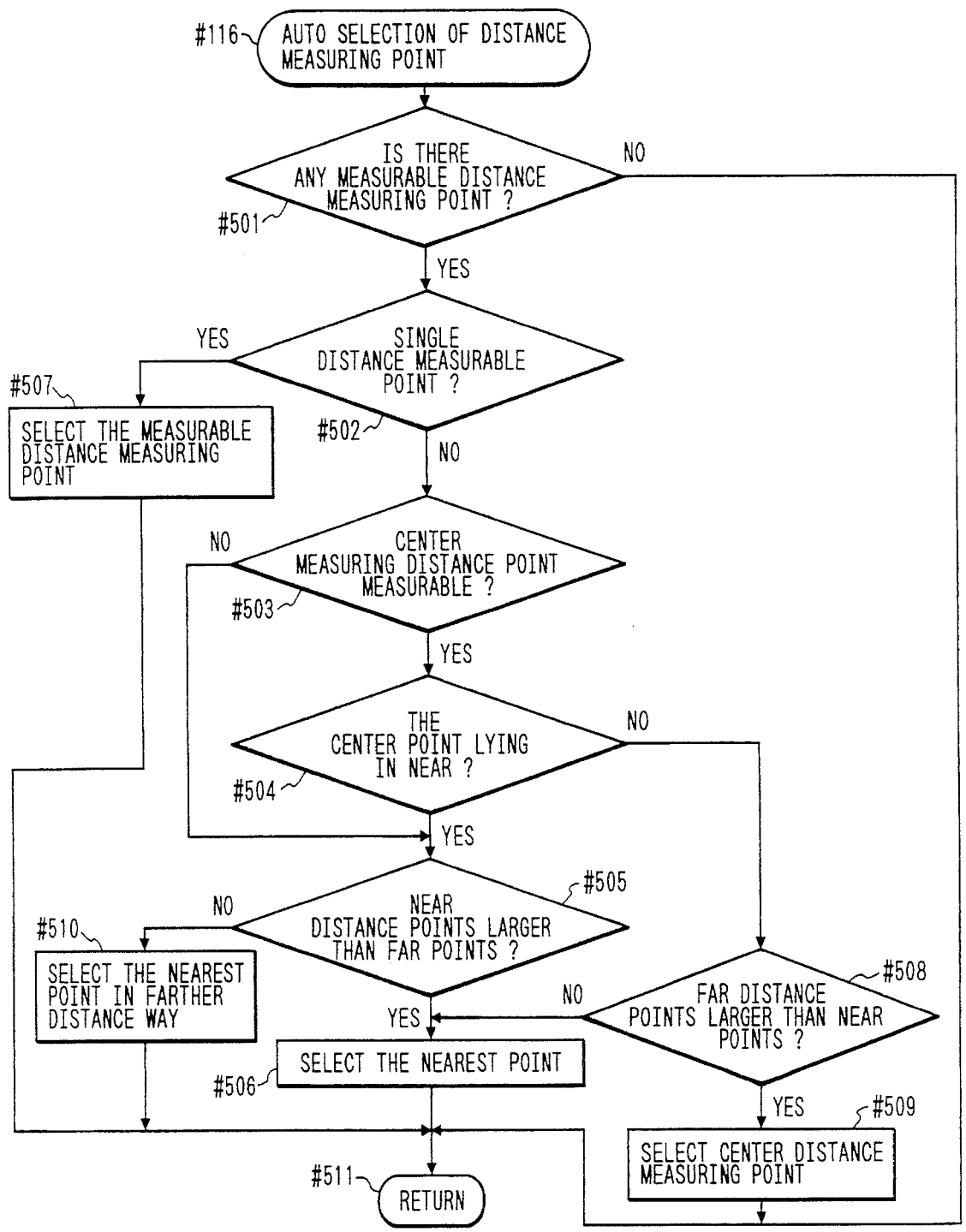
FIG. 9 is a flow chart showing an algorithm for automatically selecting the distance measuring point.
Figure 12E:
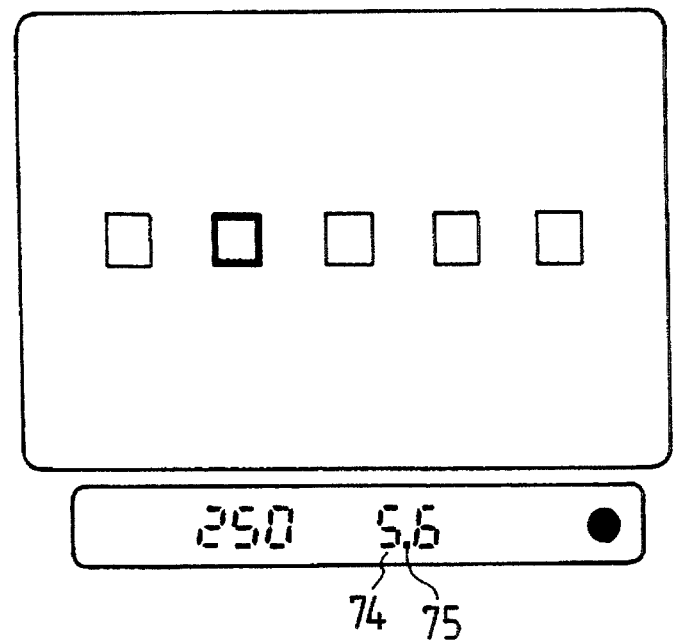

In the following there will be explained the automatic distance measuring point selecting subroutine (#116) with reference to FIG. 9. Said subroutine is executed in case of the visual axis detection inhibiting mode, namely in case the visual axis input mode is not selected, and is to determine the distance measuring point from the defocus amounts and the absolute distance information of the distance measuring points. At first, there is discriminated whether the distance measurement is possible in any of five distance measuring points (#501), and, if the distance measurement is impossible in any point, the sequence returns to the main routine (#511). If the distance measurement is possible only in one point (#502), said point is selected as the distance measuring point (#507). If the distance measurement is possible at two or more points, there are discriminated whether said points include the central distance measuring point (#503), and whether the central distance measuring point is a short distance (for example not more than 20 times of the focal length) (#504). If the central distance measuring point allows the distance measurement and is a short distance, or if said point does not allow distance measurement, the sequence proceeds to a step #505 in which, if the number of near-side distance measuring points is larger than that of far-side distance measuring points, the main object is identified to be considerably close to the photographer and the nearest distance measuring point is selected (#506). On the other hand, if the number of near-side distance measuring points is less, the main object is identified to be at the far side, and, in consideration of the depth of focus, the nearest point among the far-side distance measuring points is selected (#510). If the step #504 identifies that the central distance measuring point is far, the sequence proceeds to a step #508, in which, if the number of far-side distance measuring points is larger than that of near-side distance measuring points, the main object is identified to be at the far side including the central distance measuring point, and the central distance measuring point is selected (#509). On the other hand, if the number of the far-side distance measuring points is less, the nearest point is selected as explained above (#506). As explained in the foregoing, if distance measuring point or points enabling distance measurement are present, a point is automatically selected, then the sequence returns to the main routine (#511) and the focus state detection is executed again at said distance measuring point (#107). As in the in-focus display shown in FIG. 12D in case of selection of the distance measuring point utilizing the visual axis information, the in-focus display in this case is made by the point 201 and the in-focus mark 79 as shown in FIG. 12E, but the visual axis input mark 78 remains naturally turned off.

Figure 10A:
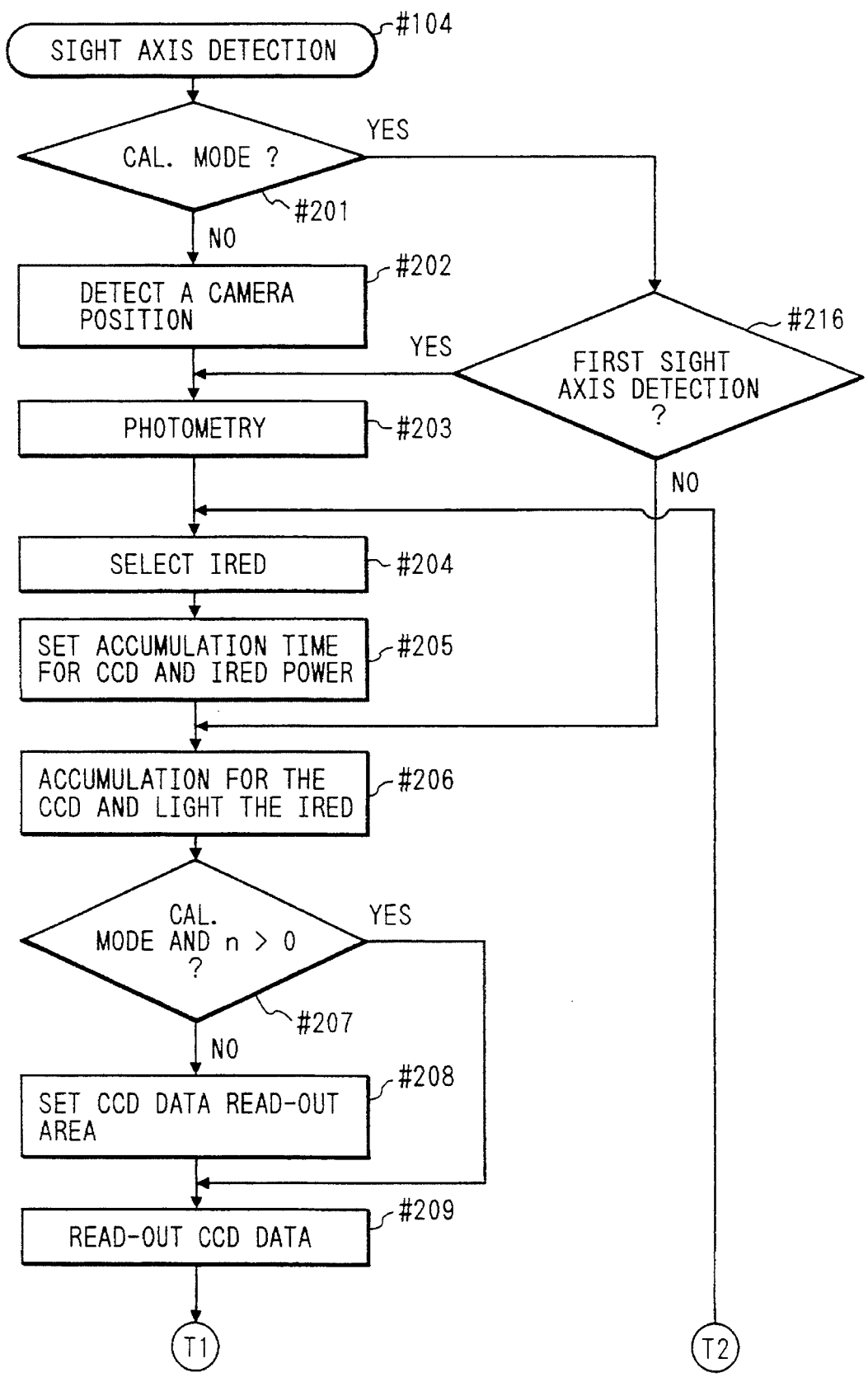
FIGS. 10A and 10B are flow charts for detecting the visual axis.
Figure 10B:
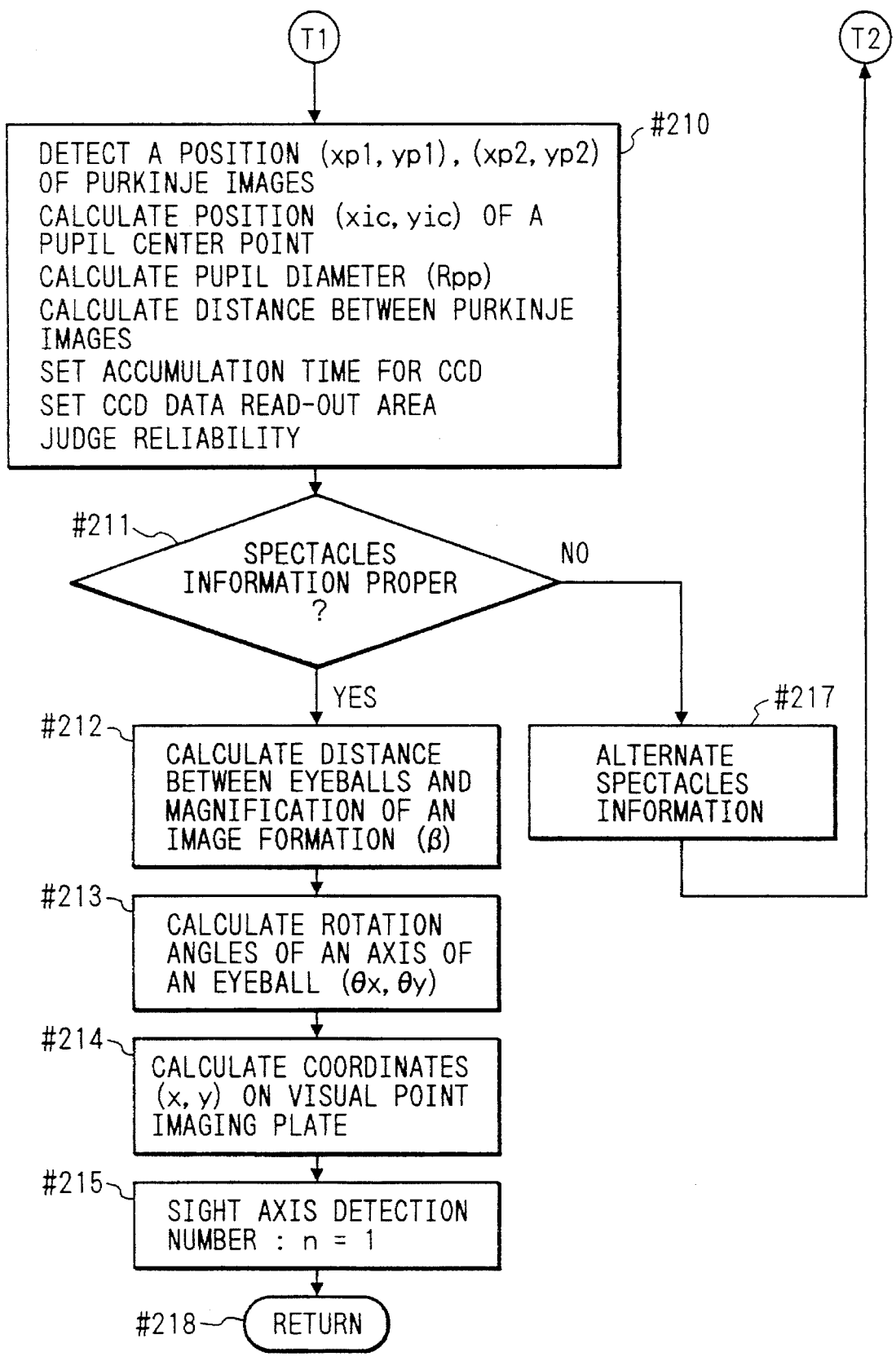

FIGS. 10A and 10B are flow charts of visual axis detection. As explained in the foregoing, upon receiving a signal from the CPU 100, the visual axis detecting circuit 101 executes the detection of visual axis (#104). Then the circuit 101 discriminates whether the visual axis detection is executed in a phototaking mode or in the visual axis calibration mode (#201), and confirms the calibration number to be explained later, at which the camera is set.

In case of visual axis detection in a phototaking mode, the visual axis detecting circuit 101 at first detects the position of the camera, through the signal input circuit 104 (#202).

By processing the output signal of the mercury switch 27 (SW-ANG), the signal input circuit 104 discriminates whether the camera is in the horizontal or vertical position, and, in case of the vertical position, whether the shutter release button 41 is at the top or near the ground. Then the luminance information of the object area is obtained from the light metering circuit 102, through the CPU 100 (#203). Then, the infrared light-emitting diodes (IRED) 13a–13f are selected according to the previously detected information on the camera position and the spectacles information of the photographer contained in the calibration data (#204). If the camera is in the horizontal position and the photographer does not wear the spectacles, the IRED's 13a, 13b close to the optical axis of the view finder, as shown in FIG. 2A, are selected. If the camera is in the horizontal position but the photographer wears the spectacles, there are selected IRED's 13c, 13d distant from said optical axis. In this situation, the illuminating light reflected by the spectacles of the photographer does not reach the predetermined area of the image sensor 14 on which the eye image is projected, so that the analysis of said image is not hindered. If the camera is held in the vertical position, there are selected IRED's 13a, 13c or 13b, 13f so as to illuminate the eyeball of the photographer from below as will be explained further afterwards.

Then the charge accumulation time of the image sensor 14 (CCD-EYE) and the illuminating power of the IRED are selected according to the light metering information and the spectacles information of the photographer (#205). These parameters may also be set for example according to the contrast of the eye image obtained in the preceding detection of the visual axis.

After the setting of these parameters, the VPU 100 turns on the IRED with the predetermined power through the IRED driving circuit 107, and causes the visual axis detecting circuit 101 to start the charge accumulation of the CCD-EYE (#206). The CCD-EYE completes the charge accumulation according to the previously selected accumulation time, whereupon the IRED's are turned off. Except in the visual axis calibration mode (#207), the read-out area of the CCD-EYE is selected (#208). Said read-out area is selected based on that in the preceding detection of the visual axis, except in the first detection after the start of power supply of the camera body, but the CCD-EYE is read over the entire area in case of a change in the camera position or in the presence/ absence of the spectacles. After the read-out area setting, there is executed the read-out operation of the CCD-EYE (#209). In this read-out operation, the area outside the read-out area is skipped by an idle reading. The output of the CCD-EYE is A/D converted in the visual axis detecting circuit 101, then stored in the CPU 100 and used therein for the extraction of the feature points of the eyeball image (#210). More specifically, in the CPU 100, there are detected the positions (Xp1, Yp1), (Xp2, Yp2) of the Purkinje's images which are false images of the paired IRED's used for illuminating the eyeball. Since said Purkinje's images appear as strongly bright points, they can be detected as images exceeding a certain threshold value of light intensity. Also the center (Xic, Yic) of the pupil can be determined by detecting plural boundary points between the pupil 19 and the iris 17, and effecting a minimum square approximation for a circle, based on said boundary points. Also the diameter Rpp of the pupil can be obtained at the same time. Further, the distance can be determined from the distance of the two Pulkinye's images.

In addition the eye image analysis, the CPU CPU 100 detects the contrast of said image, thereby re-setting the charge accumulation time of the CCD-EYE. It also sets the read-out area of the CCD-EYE, based on the positions of the Purkinje's images and of the pupils. Said read-out area is so selected as to include the pupil and to enable detection of the entire pupil even with a certain change in the position thereof. It is however naturally smaller than the size of the iris. Said read-out area is selected as a rectangle, and the coordinates of the two diagonal points are memorized in the visual axis detecting circuit 101. Also the reliability of calculated positions of the Purkinje's images and of the center of the pupil is judged from the contrast of the eye image and the size of the pupil.

After the analysis of the eye image, the visual axis detecting circuit 101, serving also as the confirmation means for the calibration data, judges whether the spectacles information in the calibration data is correct, based on the calculated distance of the Purkinje's .images and the IRED's turned on (#211). This is to deal with the photographer who wears the spectacles only occasionally. More specifically, if the spectacles information for the photographer in the calibration data indicates that the spectacles are worn so that the IRED's 13c, 13d are turned on, and if the distance of the Purkinje's images is larger than predetermined value, the photographer is identified to be wearing the spectacles so that the spectacles information is regarded correct. On the other hand, if the distance of said images is smaller than said predetermined value, the photographer is identified as not wearing the spectacles or wearing contact lenses, so that the spectacles information is incorrect. In such case (#211), the visual axis detecting circuit 101 varies the spectacles information (#217) and selects the IRED's again (#204) to execute the visual axis detection. In said variation of the spectacles information, however, the spectacles information stored in the EEPROM of the CPU 100 is not varied.

On the other hand, if the spectacles information is identified correct (#212), the distance between the eyepiece lens of the camera and the eyeball 15 of the photographer is calculated from the distance of the Purkinje's images, and the imaging magnification β of the eye image projected on the CCD-EYE is calculated from said calculated distance (#212). From these calculations, the rotation angles θx, θy of the optical axis of the eyeball 15 satisfy following equations (#213), based on the equation (1):

$$\beta * OC * SIN\theta x = (Xp0+\delta x) - Xic \qquad (4)$$

$$\beta * OC * SIN\theta y = (Yp0+\delta y) - Yic \qquad (5)$$

wherein $$xp0 = (Xp1+Xp2)/2$$

$$Yp0 = (Xp1+Xp2)/2$$

and δx, δy are correction factors for correcting the center positions of the two Purkinje's images.

With said rotation angles θx, θy, the position (X, Y) of the line of sight on the focusing screen is given as follows (#214):

$$X = m * \frac{\theta x - (Cx * Rpp + Dx)}{Ax * Rpp + Bx} \qquad (6)$$

$$Y = m * \frac{\theta y - (Cy * Rpp + Dy)}{Ay * Rpp + By} \qquad (7)$$

wherein Rpp is the diameter of the pupil, and Ax, Bx, Cx, Dx and Ay, By, Cy, Dy are calibration data, respectively in the horizontal (x) direction and in the vertical direction, for calibrating the individual difference in the visual axis. The method for determining said calibration data will be explained later.

After the determination of the coordinates of the visual axis on the focusing screen, there is set a flag indicating that the visual axis detection has been conducted once (#215), and the sequence returns to the main routine (#218).

The flow chart of the visual axis detection shown in FIGS. 10A and 10B is effective also in the visual axis calibration mode. If the step #201 identifies the visual axis detection in the calibration mode, there is discriminated whether the visual axis detection this time is the first one in the calibration mode (#216). If it is identified as the first one in the calibration mode, the ambience luminance is measured (#203) for setting the charge accumulation time of the CCD-EYE and the illuminating power of the IRED. The operations thereafter are same as explained above.

On the other hand, if the visual axis detection this time is identified as the second or subsequent one in the calibration mode (#216), the charge accumulation time of the CCD-EYE and the illuminating power of the IRED are selected as in the preceding cycle and the activation of the IRED and the charge accumulation of the CCD-EYE are immediately started (#206). Also in the second or subsequent visual axis detection in the visual axis calibration mode (#207), the read-out area of the CCD-EYE is selected same as in the preceding cycle, so that the read-out of the CCD-EYE is executed immediately after the completion of charge accumulation (#209). The operations thereafter are same as explained above.

In the visual axis detecting flow chart shown in FIGS. 10A and 10B, the variables at the returning to the main routine are the coordinates (x, y) of the visual axis on the focusing screen in case of the ordinary visual axis detection, but, in case of the visual axis detection in the calibration mode, said variables are rotation angles (θx, θy) of the optical axis of the eyeball of the photographer. Other variables, which are the reliability of results of detection, the charge accumulation time of the CCD-EYE, the read-out area thereof etc. are common in both cases.

In the present embodiment, the light metering information obtained in the sensor 10 of the camera is utilized for setting the charge accumulation time of the CCD-EYE and the illuminating power of the IRED, but there may be provided means, in the vicinity of the eyepiece lens 11, for detecting the luminance of the frontal part of the eyeball of the photographer, for this purpose.

Figure 11B:
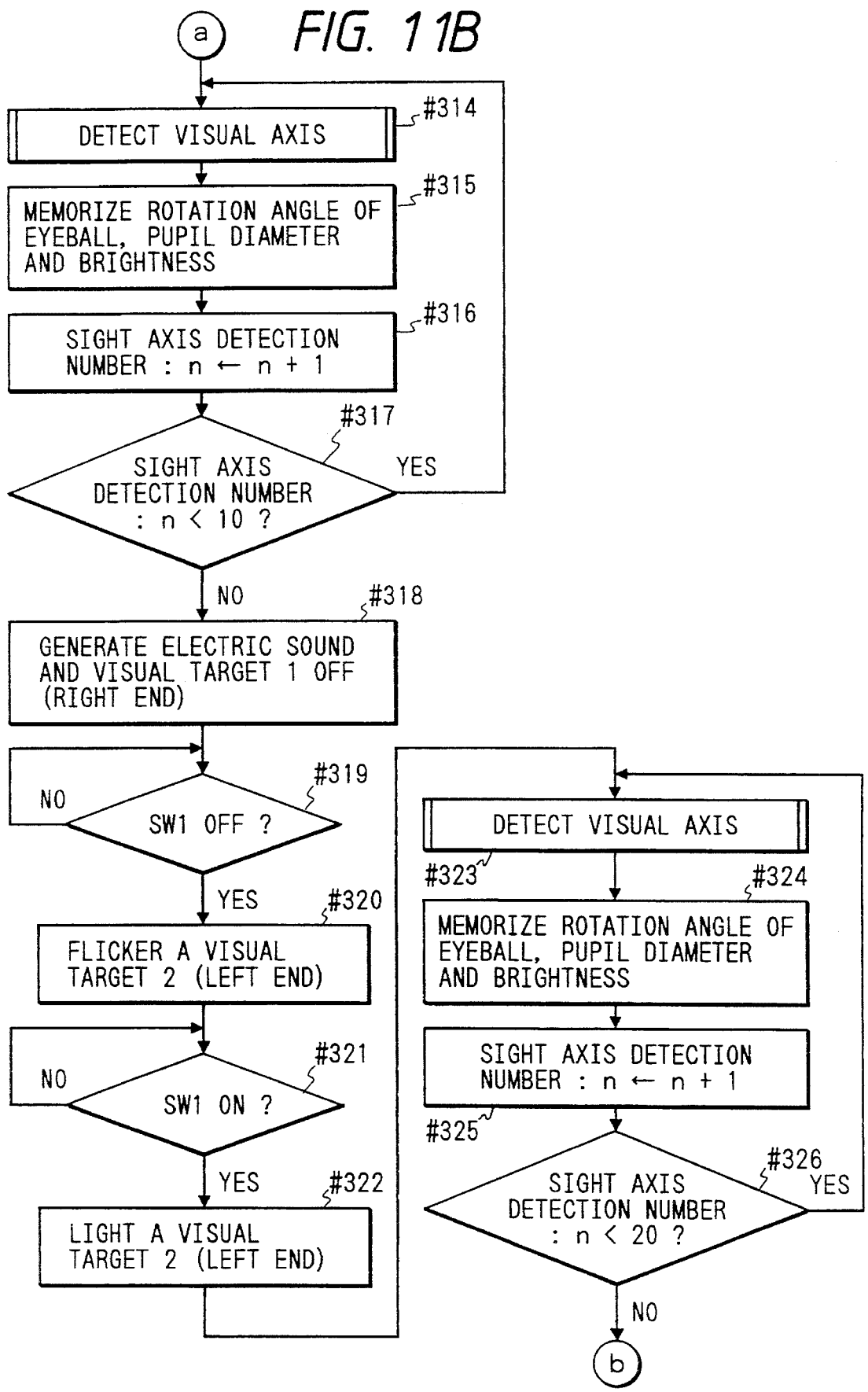
FIG. 11 is comprised of FIGS. 11A to 11C showing a flow chart for calibrating the visual axis.
Figure 11C:
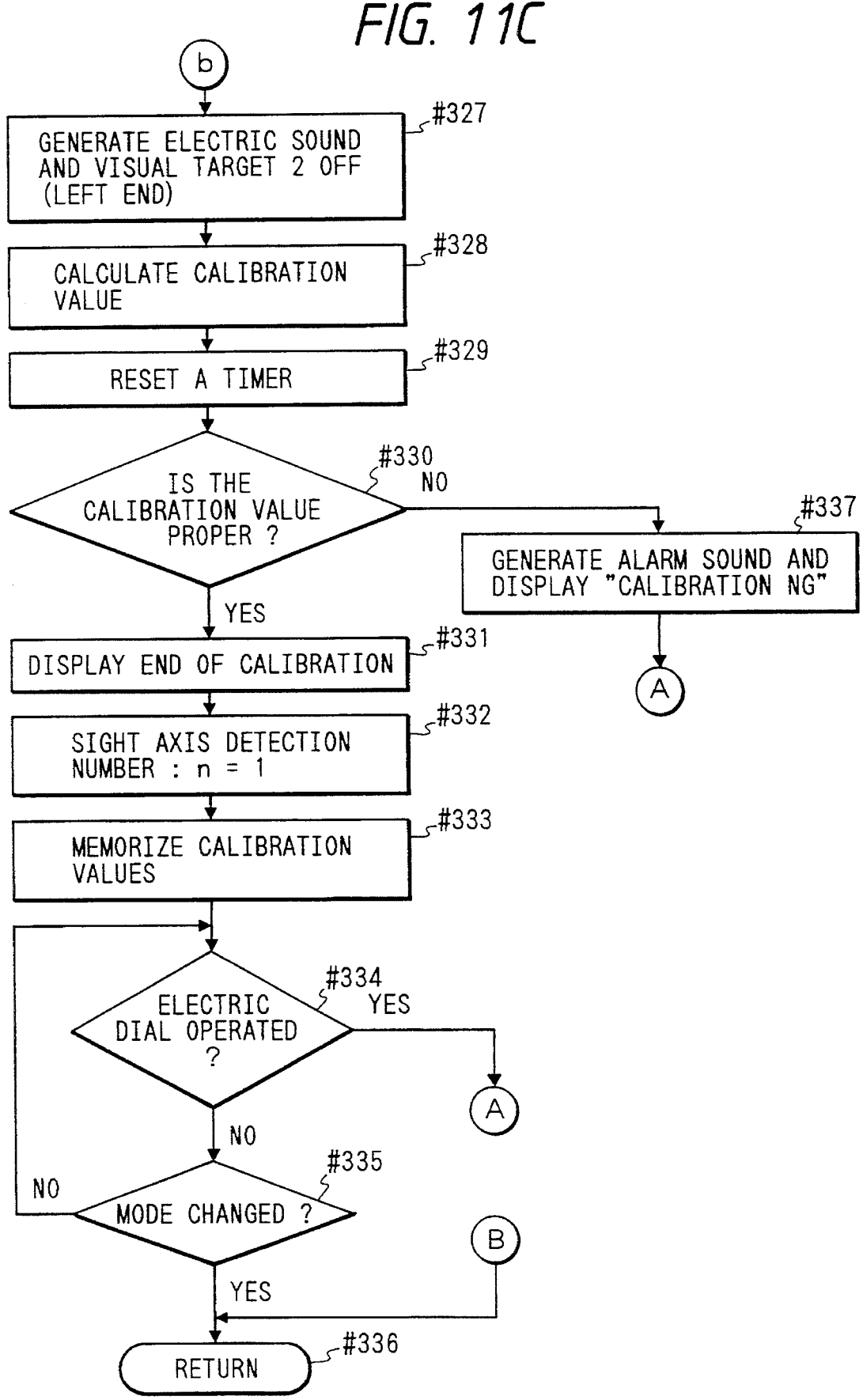

FIGS. 11A to 11C are flow charts of the visual axis calibration, and FIGS. 13A to 18D show the display states of the in-finder LCD 24 and the monitoring LCD 42 in the visual axis calibration.

When the photographer rotates the mode dial 44 to match the CAL position 44d with the index mark, there is set the visual axis calibration mode, and the signal input circuit 104 sends a signal to the LCD driving circuit 105 through the CPU 100, whereby the monitoring LCD 42 provides a display indicating that one of the calibration modes to be explained later is selected. Also the CPU 100 resets the variable stored in the EEPROM, except for the calibration data (#301).

Figure 13A:
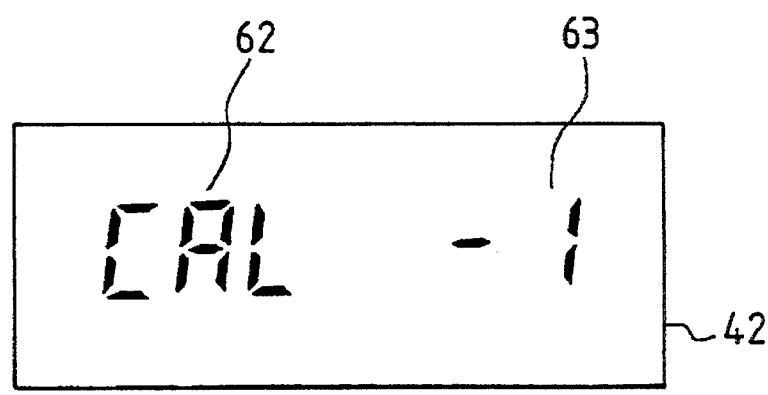
FIGS. 13A to 13C and 14 are views showing displays of the monitoring LCD's in a calibration mode.
Figure 13B:
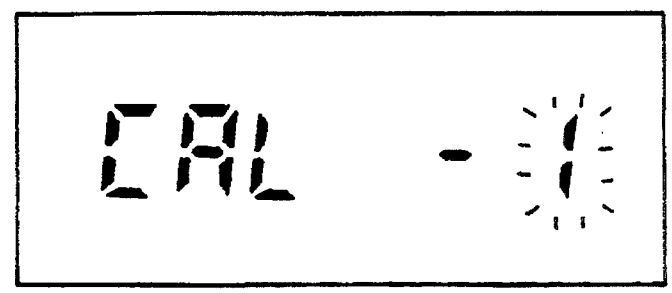
Figure 13C:
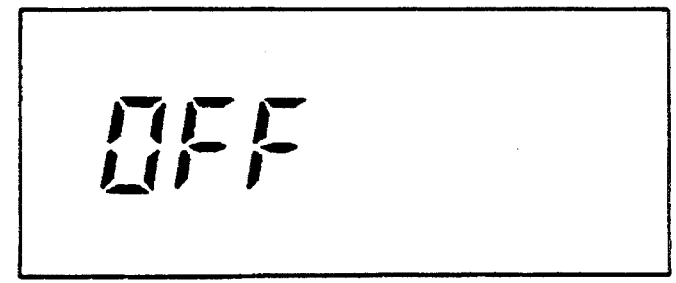

The monitor LCD 42 displays the currently set calibration mode, as shown in FIG. 13A. The calibration modes include an ON mode for effecting the calibrating operation, and an OFF mode for not effecting said operation. In the ON mode, there are provided calibration numbers CAL1–CAL5 corresponding to the calibration data numbers 1–5. Said calibration number is displayed by the 7-segment display 62 for displaying the shutter speed and the 7-segment display 63 for displaying the diaphragm aperture, and the fixed segment display area 42a is all turned off (FIG. 13A shows the state of the calibration number 1, and the 7-segment displays alone are shown in magnified manner). If the calibration data corresponding to the set calibration number are initial values, the calibration number flashes on the monitor LCD 42 (FIG. 13B). On the other hand, if a calibration, to be explained later, is already executed at the set calibration number and calibration data different from the initial values are stored in the EEPROM at an address corresponding to said calibration number, said number is continuously displayed on the monitor LCD 42 (FIG. 13A). Consequently the photographer can recognize whether the calibration data have already been entered at the currently set calibration number. The initial value of the calibration data number is selected as "0", so that the information input by the visual axis is not executed unless the visual axis calibration is executed.

In the OFF mode, the 7-segment display 63 displays "OFF" (FIG. 13C), whereby the calibration data number "0" is always selected, and the visual axis inhibiting mode is set. Such mode, for phototaking without the information input by the visual axis, is effective for preventing erroneous operation resulting from mistaken visual axis detection, for example in case of asking another person to operate the camera. Then, a timer in the CPU 100 is started to initiate the calibration of the visual axis (#302). If the camera is not manipulated for a predetermined period after the start of the timer, the visual axis detecting circuit 101 resets the current calibration data number to "0", thereby selecting the visual axis inhibiting (OFF) mode. Also any flashing mark for visual axis calibration, in the view finder, is turned off.

Figure 14:
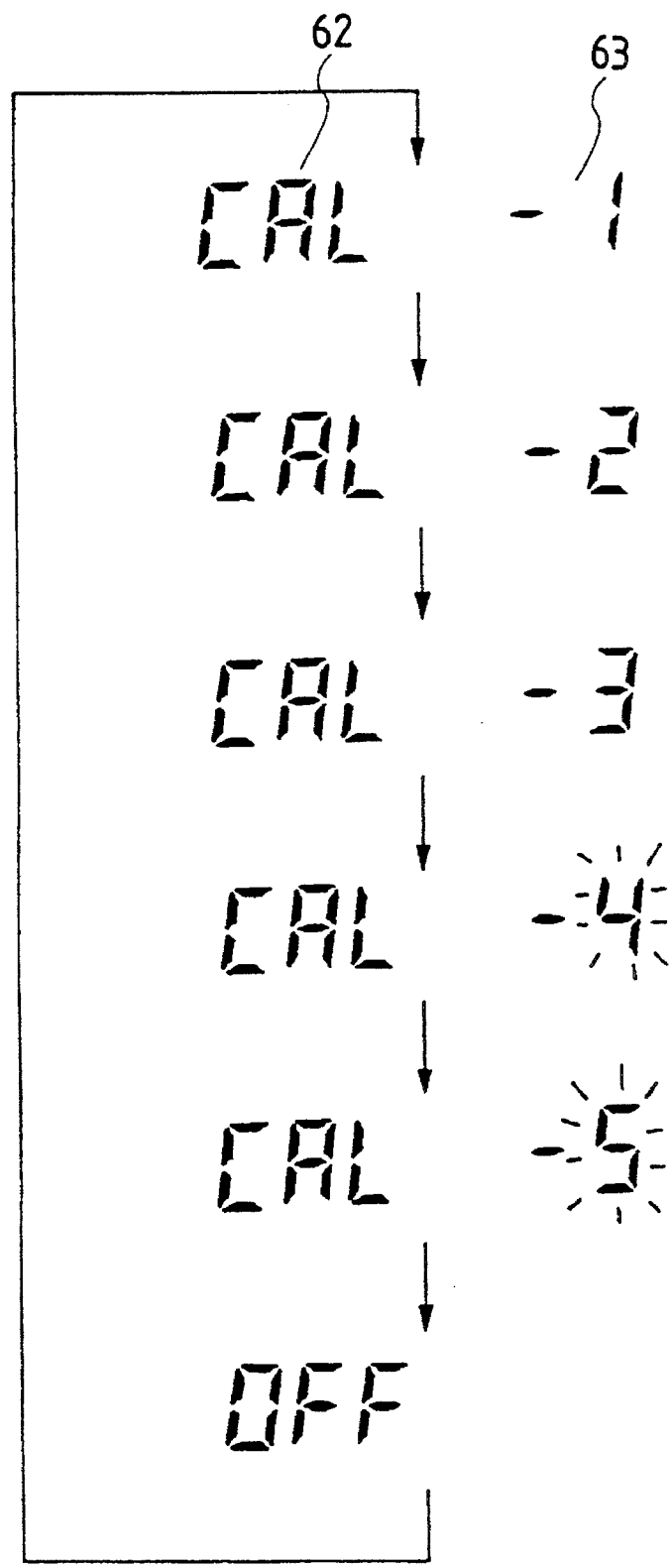

In response to a rotation of the electronic dial 45 by the photographer, the signal input circuit 104 sends a corresponding signal to the LCD driving circuit 105 through the CPU 100. As a result, in synchronization with the rotation of the electronic dial 45, the calibration number displayed on the monitor LCD 42 varies, as shown in FIG. 14. With the clockwise rotation of the electronic dial 45, the display varies in the order of CAL1, CAL2, CAL3, CAL4, CAL5, so that the photographer can store the calibration data in any of five calibration numbers, in the calibrating operation to be explained later. The displays shown in FIG. 14 indicate that the calibration data are already entered at CAL-1, 2 and 3, while CAL-4 and 5 still remain as the initial values. Then, in response to a further clockwise rotation by a click provides a display OFF, at which the calibrating operation is not conducted and the visual axis inhibiting mode is selected. A further rotation by a click shifts the display to CAL-1. In this manner, the calibration data numbers are displayed cyclically. Also in response to an anticlockwise rotation, the displays are given in the inverse order. When the photographer selects a desired calibration number by looking at the calibration numbers displayed on the monitoring LCD 42, the visual axis detecting circuit 101 confirms the selected calibration data number through the signal input circuit 104 (#303). The confirmed calibration data number is memorized in a predetermined address in the EEPROM of the CPU 100. However, if the confirmed calibration data number has not been changed, the storage thereof in the EEPROM is not executed.

Figure 15:
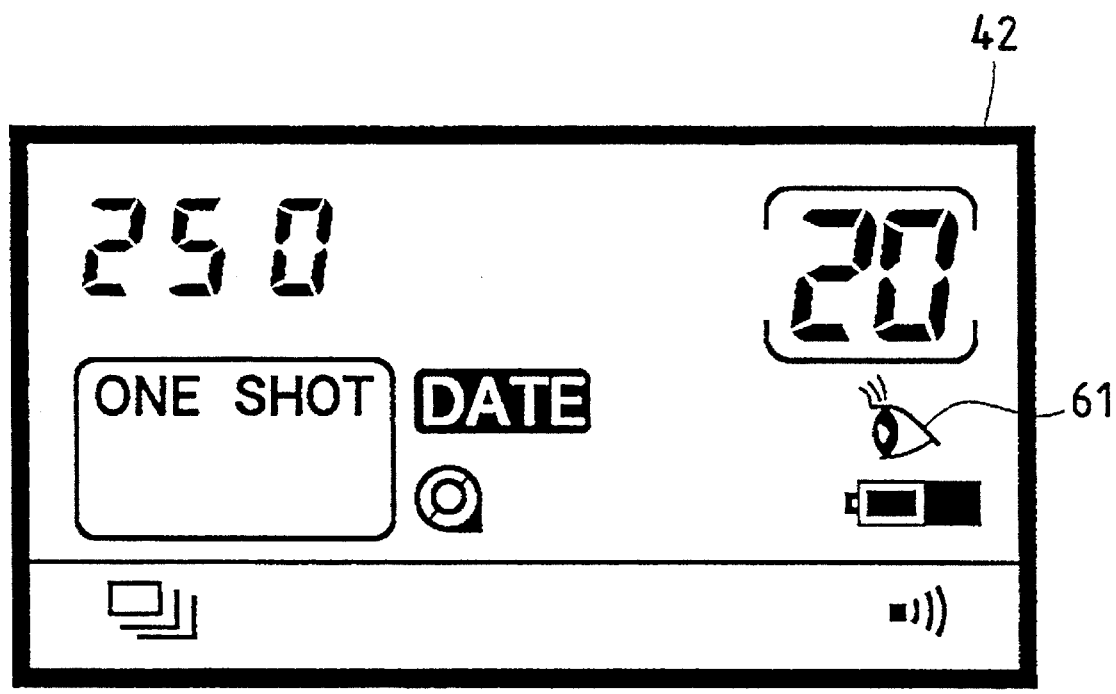
FIG. 15 is a view showing display state of the monitoring LCD's in a visual axis input mode.

In succession, the visual axis detecting circuit 101 confirms the phototaking mode through the signal input circuit 104 (#306). If it is confirmed that the photographer has switched to another phototaking mode than the visual axis calibration mode by rotating the mode dial 44 (#304), the flashing mark for the visual axis calibration in the view finder is turned off (#305) and the sequence returns to the main routine for phototaking in the camera (#336). When the mode dial 44 is switched to another phototaking mode (for example shutter preferential AE) while one of the calibration numbers CAL1–5 is displayed, the visual axis detection is executed with the data of said calibration number, and the phototaking operation is conducted with thus obtained visual axis information. FIG. 15 shows the display of the monitoring LCD 42 in this state, wherein the visual axis input mode display 61 is turned on in addition to the ordinary display of the phototaking mode, thereby advising the photographer of the visual axis input in which the phototaking operation is conducted by the visual axis information.

On the other hand, if it is confirmed that the visual axis calibration mode is still selected (#304), there is again confirmed the calibration data number set by the electronic dial 45 (#306). If the calibration data number is set at "0" for selecting the visual axis inhibiting mode, the calibration number is again memorized in the EEPROM of the CPU 100 (#303). When the visual axis inhibiting mode is selected in the calibration mode, the camera waits until another phototaking mode is selected by the mode dial 44. Thus, if the mode dial 44 is switched while "OFF" is displayed, there will be executed the phototaking operation without the visual axis detection, and the visual axis input mode display 61 is turned off in the monitoring LCD 42.

Figure 17A:
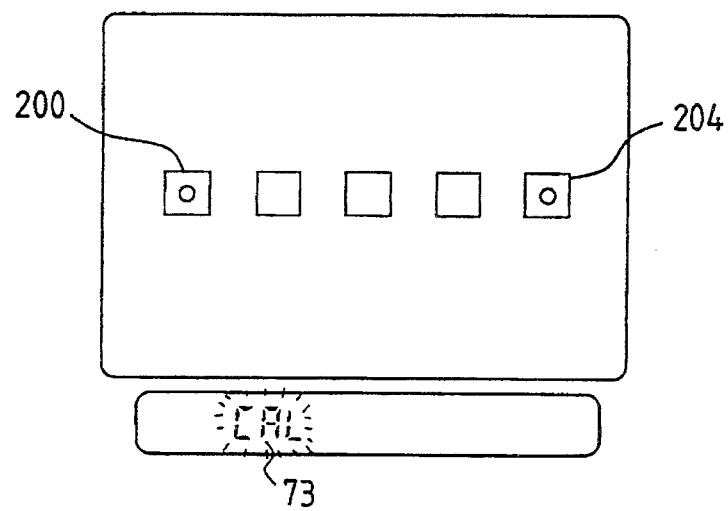

If the calibration data number is selected at a non-zero value (#306), the CPU 100 continues to detect the camera position by the signal input circuit 104 (#307), which discriminates whether the camera is in the horizontal position or in the vertical position, and, in the latter case, whether the shutter release button 41 is on the top or close to the ground, by processing the output signal of the mercury switch 27. Since the camera is usually used in the horizontal position, the hardware structure for the visual axis calibration is so designed that the calibration is possible when the camera is held in the horizontal position. Consequently, the visual axis detecting circuit 101 does not execute the visual axis calibration when informed by the CPU 100 that the camera position is not horizontal (#308). Also in order to inform the photographer that the visual axis calibration is not possible because of the non-horizontal camera position, the visual axis detecting circuit 101 provides a flashing display "CAL" on the LCD 24 in the view finder, as shown in FIG. 17A. At the same time there may be given an alarm sound by an unrepresented alarm sound generator.

Figure 16A:
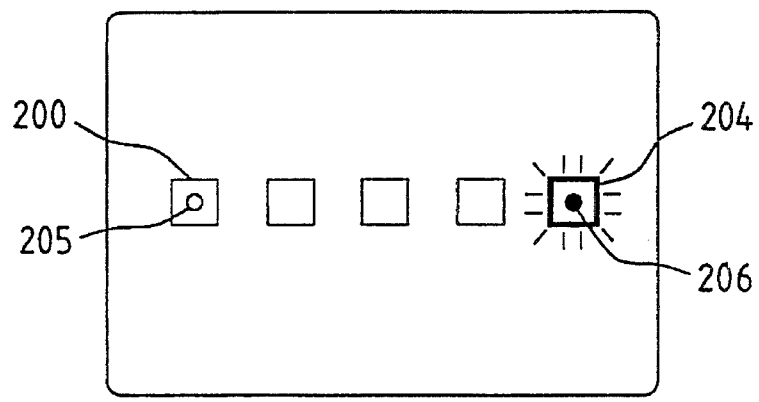
FIGS. 16A to 16D, and 17A and 17B are views showing displays in the view finder in a calibration mode.
Figure 16B:
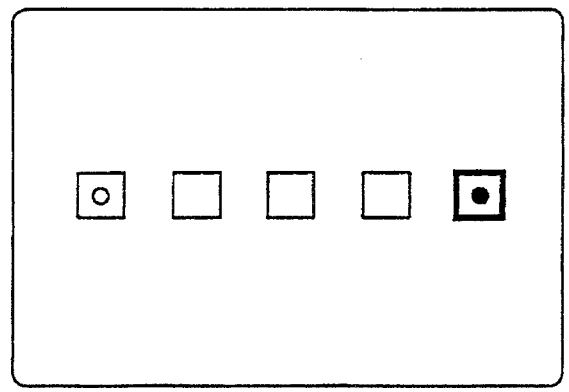

On the other hand, if the camera position is detected as horizontal (#308), the visual axis detecting circuit 101 sets the number of visual axis detection as "0" (#309). The calibration of the visual axis is initiated by turning on the switch SW1. In order to prevent the start of the calibration in the camera before the photographer becomes prepared, the visual axis detecting circuit 101 confirms the state of the switch SW1, and, if it is on by the depression of the shutter release button 41, the sequence waits until the switch SW1 is turned off (#310). When the visual axis detecting circuit 101 confirms, through the signal input circuit 104, that the switch SW1 is off (#310), a signal is sent to the LED driving circuit 106 to flash the marks for the visual axis calibration (#311). Said marks for the visual axis calibration are used commonly with the distance measuring point marks, in order that the photographer can smoothly execute the calibrating operation by the guidance of the superimposed display, and, the distance measuring point mark 204 at the right end and the dot mark 206 flash at first (FIG. 16A).

The camera waits if the "ON" signal from the switch SW1, which is the trigger signal for starting the visual axis calibration, is not entered (#312). When the photographer watches the flashing mark and turns on the switch SW1 by depressing the shutter release button 41 (#312), the visual axis detecting circuit 101 sends a signal through the CPU 100 to the LED driving circuit 106, thereby turning on the mark for the visual axis calibration (#313) (FIG. 16B), whereby the photographer can visually recognize that the visual axis detection is started. Prior to the visual axis detection for obtaining the calibration data, there is discriminated whether the photographer is looking at the view finder with or without the spectacles, and there is selected the illumination for the photographer without spectacles or that for the photographer with spectacles, according to the result of said discrimination (#338). The method of said discrimination will be explained later. After the selection of the illuminating method, there is in succession executed the visual axis detection for obtaining the calibration data (#314). The visual axis detecting operation is conducted as explained in the flow chart shown in FIG. 10.

The distance measuring point marks 204, 200 at the right and left ends are provided with dot marks 205, 206 which indicate that the calibration is to be conducted at the positions of said marks and which can be continuously or intermittently illuminated by the superimposing LED's. The distance measuring point marks indicate the focus state detecting areas and are therefore required to display the corresponding areas. On the other hand, for achieving precise calibration, it is required that the photographer watches a fixed point. For this reason said dot marks 205, 206 are formed smaller than the distance measuring point marks, in order to facilitate the watching of a point. The sight line detecting circuit 101 memorizes the rotation angles $\theta x$, $\theta y$ of the eye, the pupil diameter Rpp and the reliability of these data, which are given as variables of the visual axis detecting subroutine (#315), and counts up the number n of visual axis detections (#316). Since the visual axis of the photographer fluctuates by a certain amount, it is effective to conduct plural visual axis detections for a mark, in order to obtain precise calibration data for the visual axis. The method of processing of the calibration data will be explained later. In the present embodiment, there are executed 10 visual axis detections for a mark. If the number visual axis detections has not reached 10 (#317), the visual axis detecting operation is continued (#314). If said number has reached 10, the visual axis detection for the mark 1 (distance measuring point mark 204 and dot mark 206) is terminated (#317). In order to inform the photographer that the visual axis detection for the mark i has been completed, the visual axis detecting circuit 101 causes, through the CPU 100, an unrepresented sounding device to generate electronic sound several times. At the same time, the visual axis detecting circuit 101 causes the LED driving circuit 106 to turn off the mark 1 (#318).

Figure 16C:
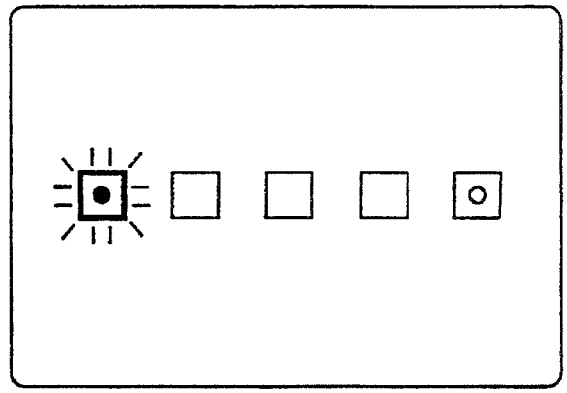
Figure 16D:
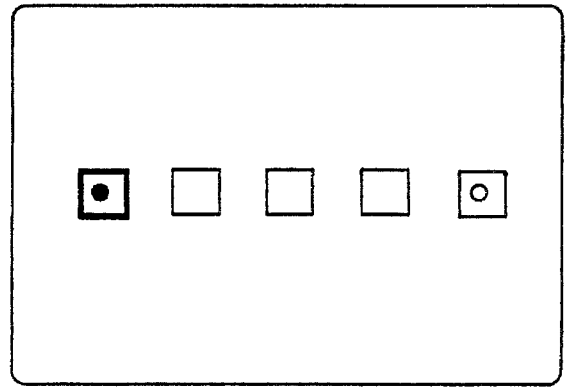

In succession, the visual axis detecting circuit 101 discriminates, through the signal input circuit 104, whether the switch SW1 is turned off (#319), and, if it is ON, the sequence waits until it is turned off, but, if it is OFF, the mark 2 at the left end (distance measuring mark 200 and dot mark 205) starts to flash (#320) (FIG. 16C). Then the visual axis detecting circuit 101 again discriminates, through the signal input circuit 104, whether the switch SW1 is turned on (#321), and, if it is off, the sequence waits until it is turned on, but, if it is on, the visual axis detecting circuit 101 sends a signal, through the CPU 100, to the LED driving circuit 106 to turn on the mark for the visual axis calibration (#322) (FIG. 16D). Then the visual axis detection is executed (#323). The visual axis detecting circuit 101 memorizes the rotation angles θx, θy of the eye ball, the pupil diameter Rpp and the reliability of these data, which are the variables obtained from the visual axis detecting subroutine (#324), and counts up the number n of the visual axis detections (#325). If the number n does not reach 20 (#326), the visual axis detection is continued (#323), but, if said number reaches 20, the visual axis detection for the mark 2 is terminated (#326).

In order to inform the photographer that the visual axis detection for the mark 2 has been completed, the visual axis detecting circuit 101 causes, through the CPU 100, an unrepresented sound generating device to generate electronic sound several times. At the same time, the visual axis detecting circuit 101 turns off the mark 2 through the LED driving circuit (#327).

When the detection of the visual axis data for calculating the calibration data is completed, the calibration data is calculated from the eye ball rotation angles θx, θy and the pupil diameter Rpp memorized in the visual axis detecting circuit 101 (#328), in the following manner.

The coordinates of the marks 1, 2 on the focusing screen 7 are taken as (X1, 0), (X2, 0). Also the averages of ten rotation angles (θx, θy) of the eye ball stored in the visual axis detecting circuit 101 are represented by (θx1, θy1) when the photographer watches the mark 1, and (θx2, θy2) when the photographer watches the mark 2. Also the standard deviations of the eye ball rotation angles when watching the marks are taken as σx1, σy1, σx2, σy2. Furthermore, threshold values θth for eliminating data significantly distant from the average values of the eye ball rotation angles are selected as:

θthx1=σx1

θthx1=1.5*σy1

θthx2=σx2

θy2=1.5*σy2

Said threshold values have different factors of multiplication on the standard deviations of the eye ball rotation angles, depending on the x (horizontal) direction and on the y (vertical) direction, because the required precision of visual axis detection is different, according to the direcrent.

After the elimination of the rotation angles, for which the difference |θ—θ| between said rotation angle and the average exceeds the threshold value θth, the rotation angles are averages as θx1, θy1, θx2 and θy2. Also after said elimination of the rotation angles based on the threshold values, the pupil diameters are averaged as Rpp1, Rpp2. In the following there will at first be given an explanation on the processing in the horizontal (X) direction.

Since the detected rotation angle θx depends on the pupil diameter Rpp, there can be assumed a relation:

$$\theta x = Kx*RPP+Lx \quad (8)$$

wherein the coefficients Kx, Lx are assumed as first-order functions of the visual axis coordinates and can be represented as:

$$Kx=Ax*X/m+Cx \quad (9)$$

$$Lx=Bx*X/m+Dx \quad (10)$$

When the mark 1 (horizontal coordinate X1) is watched under a certain luminocity, the rotation angle θx1 and the pupil diameter Rpp1 after the above-explained process are represented as:

$$\theta x1=Kx1*Rpp1+Lx1 \quad (11)$$

$$Kx1=Ax*X1/m+Cx \quad (12)$$

$$Lx1=Bx*X1/m+Dx \quad (13)$$

Similarly, for the mark 2 (horizontal coordinate X2) there stand:

$$\theta x2=Kx2*Rpp2+Lx2 \quad (14)$$

$$Kx2=Ax*X2/m+Cx \quad (15)$$

$$Lx2=Bx*X2/m+Dx \quad (16)$$

When Kx1, Lx1 in the equation (11) and Kx2, Lx2 in the equation (14) are determined as explained later, there can be obtained from the equations (12) and (15):

$$Ax = \frac{m*(Kx1-Kx2)}{X1-X2} \quad (17)$$

$$Cx = \frac{Kx1+KX2}{2} \quad (18)$$

Also from the equations (13) and (16) there can be obtained:

$$Bx = \frac{m*(Lx1-Lx2)}{X1-X2} \quad (19)$$

$$Dx = \frac{Lx1+LX2}{2} \quad (20)$$

The visual axis coordinate in the vertical direction can be determined from the equation (7), wherein the calibration data Ay–Dy for the vertical direction can be calculated in the following manner.

Since the detected rotation angle θY depends on the pupil diameter Rpp, there is assumed a relation:

$$\theta y=Ky*Rpp+Ly \quad (21)$$

wherein the coefficients Ky, Ly are assumed as first-order functions of the visual axis coordinate and can be represented as:

$$Ky=Ay*Y/m+Cy \quad (22)$$

$$Ly=By*Y/m+Dy \quad (23)$$

The two marks for visual axis calibration are distant in the horizontal direction, but have a same coordinate in the vertical direction. Consequently, the calibration data Ax–Dx for the horizontal direction can be determined as explained above, but those Ay–Dy for the vertical direction cannot be determined in a similar manner. For this reason, following assumption is adopted for the denominator of the equation (7):

Ay*Rpp+By=Ax*Rpp+Bx=constant

Thus:

$$Ay=0 \quad (24)$$

$$By=Ax*Rpp+Bx=constant \quad (25)$$

wherein Rpp is the average of the pupil diameter detected plural times. Also from the equations (22), (23):

$$Cy=Ky \quad (26)$$

Dy=Ly–By*Y/m

Since the coordinate Y of the mark in the vertical direction is 0:

$$Dy = Ly \quad (27).$$

In the following there will be explained the method of determining Kx1, Lx1, Kx2, Lx2, Ky and Ly.

In case of a camera, the visual axis calibration is accepted any number of times. Thus, plural values of θx, θy, Rpp obtained after the above-explained data processing in plural visual axis calibrating operations are memorized, and Kx1–Ly satisfying the equations (8) and (21) as far as possible are determined from these memorized data. For this purpose there are employed simple averaging method and minimum square method. If the variation in the memorized plural pupil diameters Rpp is limited, Kx1, Lx1 or Kx2, Lx2 or Ky, Ly are determined by simple averaging. If said variation is large, Kx1–Ly are determined by minimum square method. The simple averaging is used if the number of input data is limited due to the limited number of calibrating operations. The actual calculations are conducted in the following manner.

In a visual axis calibrating operation, the data obtained by watching the right-end mark 1, after the above-explained data process, are assumed as (θx1, θy1, Rpp1), while those obtained by watching the left-end mark 2, after said data processing are assumed as (θx1, θy2, Rpp2). Then, there are obtained:

$$\theta y = \frac{\theta y1 + \theta y2}{2}$$

$$Rpy = \frac{Rpx1 + Rpx2}{2}$$

It is assumed that n is the number of accumulated data, and ns (for example 2) is a threshold value for determining the method for calculating the coefficients Kx1–Ly.

$$Kx1 = 0 \quad (28)$$

A. If the data number n<ns, or if the variation (or deviation) of the pupil diameter Rpp is small, the simple averaging method is used for calculating Kx1–Ly according to the following equations:

$$Lx1 = \frac{\Sigma \theta x1}{n} \quad (29)$$

$$Kx2 = 0 \quad (30)$$

$$Lx2 = \frac{\Sigma \theta x2}{n} \quad (31)$$

$$Ky = 0 \quad (32)$$

$$Ly = \frac{\Sigma \theta y}{n} \quad (33)$$

B. If the data number n≧ns and if the variation of the pupil diameter Rpp is large, the minimum square method is used for calculating Kx1–Ly according to the following equations:

$$Kx1 = \frac{n * \Sigma Rpx1 * \theta x1 - \Sigma Rpx1 * \Sigma \theta x1}{n * \Sigma Rpx1\text{-}2 - (\Sigma Rpx1)\text{-}2} \quad (34)$$

$$Lx1 = \frac{\Sigma Rpx1\text{-}2 * \Sigma \theta x1 - \Sigma Rpx1 * \Sigma Rpx1 * \theta x1}{n * \Sigma Rpx1\text{-}2 - (\Sigma Rpx1)\text{-}2} \quad (35)$$

-continued $$Kx2 = \frac{n * \Sigma Rpx2 * \theta x2 - \Sigma Rpx2 * \Sigma \theta x2}{n * \Sigma Rpx2\text{-}2 - (\Sigma Rpx2)\text{-}2} \quad (36)$$

$$Lx2 = \frac{\Sigma Rpx2\text{-}2 * \Sigma \theta x2 - \Sigma Rpx2 * \Sigma Rpx2 * \theta x2}{n * \Sigma Rpx2\text{-}2 - (\Sigma Rpx2)\text{-}2} \quad (37)$$

$$Ky = \frac{n * \Sigma Rpy * \theta y - \Sigma Rpy * \Sigma \theta y}{n * \Sigma Rpy\text{-}2 - (\Sigma Rpy)\text{-}2} \quad (38)$$

$$Ly = \frac{\Sigma Rpy\text{-}2 * \Sigma \theta y - \Sigma Rpy * \Sigma Rpy * \theta y}{n * \Sigma Rpy\text{-}2 - (\Sigma Rpy)\text{-}2} \quad (39)$$

After the calculation of the visual axis calibration data as explained in the foregoing, or after the completion of the visual axis detection, a timer is set (#329).

The visual axis detecting circuit 101, serving also as the judging means for the reliability of the calibration data, judges whether the calculated visual axis calibration data are appropriate (#330).

Said judgment is executed by the reliability of the eye ball rotation angles and the pupil diameters, which are the variables from the visual axis detecting subroutine, and the calculated visual axis calibration data themselves.

More specifically, if the eye ball rotation angles and the pupil diameter detected in the visual axis detecting subroutine lack reliability, the calculated visual axis calibration data are also regarded as unreliable. On the other hand, if the eye ball rotation angles and the pupil diameter detected in said subroutine are reliable, the calculated visual axis calibration data are considered appropriate if said data are within a range of general individual fluctuation, but are considered inappropriate if said data are significantly outside said range. The visual axis detecting circuit 101 not only judges whether the calculated visual axis calibration data are appropriate or not, but also judges the level of reliability of the calculated visual axis calibration data. Said level of reliability naturally depends on the reliability of the eye ball rotation angles and the pupil diameter detected in said visual axis detecting subroutine. Said reliability of the visual axis calibration data is represented by a 2-bit number and is stored in the EEPROM of the CPU 100.

Figure 18A:
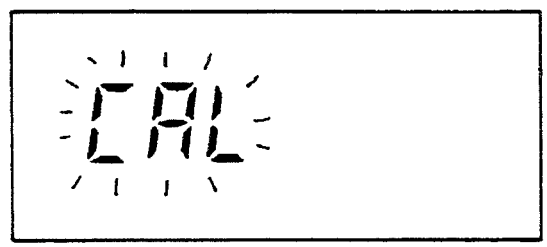
FIGS. 18A and 18B are views showing displays of the monitoring LCD's in a calibration mode.

If the calculated visual axis calibration data are judged as inappropriate (#330), the visual axis detecting circuit 101 causes, through the CPU 100, an unrepresented sounding device to generate an electronic sound for a predetermined time, indicating that the visual axis calibration data have failed. At the same time a signal is sent to the LCD driving circuit 105, thereby providing a flashing CAL display in the in-finder LCD 24 and the monitoring LCD 42 as a warning (#337) (FIGS. 17A and 18A). After said alarm sound and the alarming display on the LCD's 24, 42 for a predetermined period, the sequence returns to the initial step #301 of the calibration routine, for executing the visual axis calibration again.

Figure 17B:
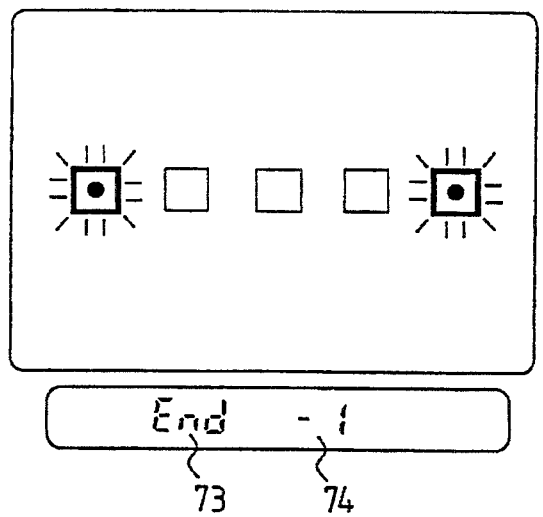
Figure 18B:
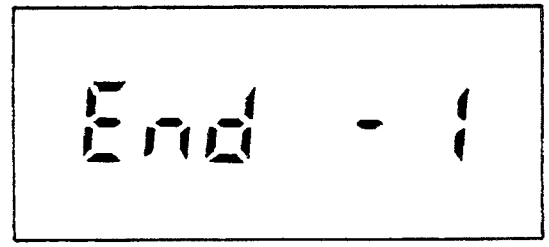

On the other hand, if the calculated visual axis calibration data are appropriate (#330), the visual axis detecting circuit 101 causes the LCD driving circuit 105 and the LED driving circuit 106 to provide a display indicating the end of the visual axis calibration (#331). The LED driving circuit 106 energizes the superimposing LED 21 to cause the marks 1, 2 to flash several times, and the LCD driving circuit 105 sends a signal to the LCD's 24, 42 to display a message "End calibration No." for a predetermined time (FIGS. 17B, 18B). The visual axis detecting circuit 101 sets the number n of visual axis detections at "1" (#332), and stores the calculated visual axis calibration data, the spectacles information of the photographer and the reliability of said calculated visual axis calibration data on an address of the EEPROM, corresponding to the currently selected calibration data number (#333). If the visual axis calibration data are already stored at said address, said calibration data are renewed.

After a serial operation for the visual axis calibration, the camera waits until the electronic dial 45 or the mode dial 44 is manipulated by the photographer. If the photographer selects another calibration number by rotating the electronic dial 45, the visual axis detecting circuit 101 detects the change in the calibration number through the signal input circuit 104 (#334), and the sequence moves to the first step #301 of the visual axis calibration routine. Also if the photographer selects another phototaking mode by rotating the mode dial 44, the visual axis detecting circuit 101 detects said change of the phototaking mode through the signal input circuit 104 (#335), and the sequence returns to the main routine (#336). At said returning to the main routine, if the calibration data have not been entered and remain as the initial values in the calibration number selected by the electronic dial 45, the visual axis detecting circuit 101 sets the calibration data number at "0" again, thereby forcedly setting the visual axis inhibiting mode. In practice, the calibration data number memorized in the EEPROM of the CPU 100 is reset to "0" (visual axis inhibiting mode).

In this embodiment the calibration of the visual axis is executed with 10 detections of the visual axis for each mark, but there may be employed visual axis detections more than or less than 10 times.

Description of features of the first embodiment

Figure 19:
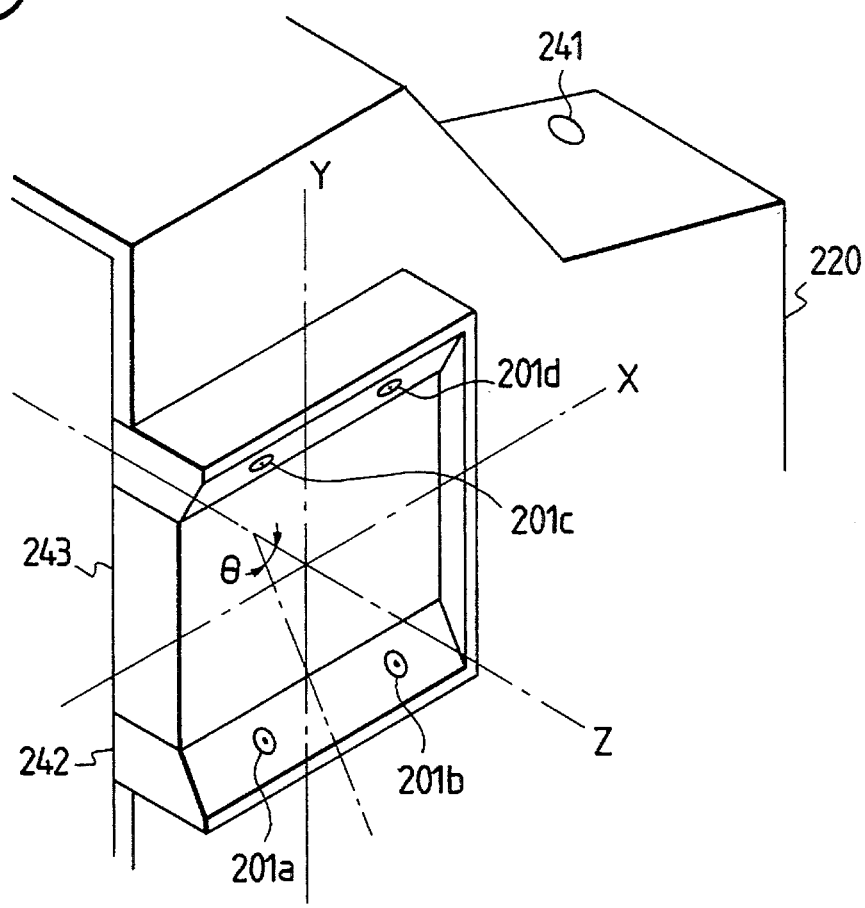
FIGS. 19 and 20 are partial views of the camera shown in FIG. 1.
Figure 20:
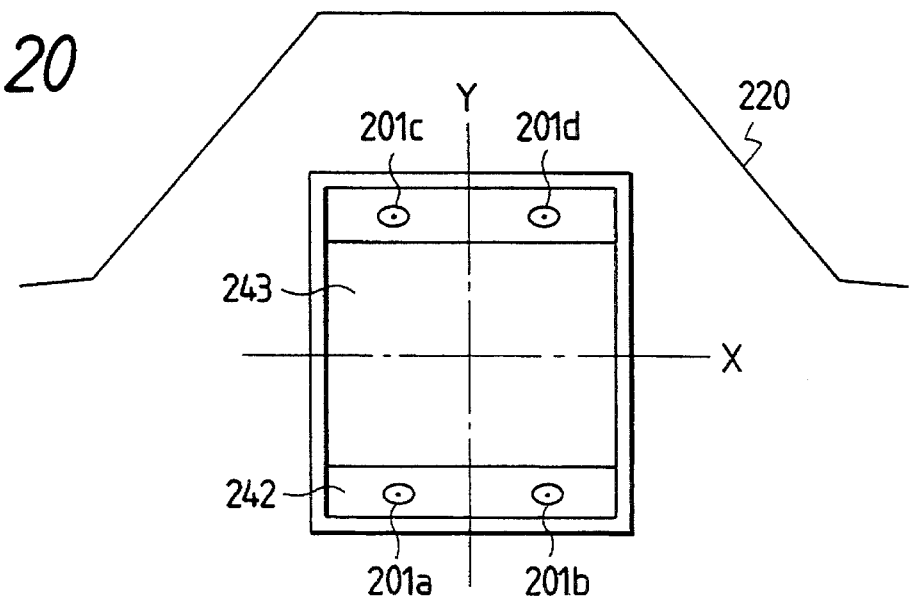

In this embodiment, when the camera is in the normal position as shown in FIGS. 19 and 20, the original point is taken at the crossing point of the optical axis Fa of the view finder and the exit plane of the eyepiece lens 243, and the optical axis Fa of the view finder is defined as the Z-axis, while a vertical axis is defined as the Y-axis, and the X-axis is taken perpendicularly to said Y- and Z-axis.

Among plural light-emitting elements 201a–201d, arbitrary two may be regarded to constitute paired elements. Paired light-emitting elements (IRED's) 201a and 201b are provided on a plane which is inclined by an angle θ to the X–Z plane (a horizontal plane containing the finder optical axis Fa) and is parallel to the X–Z plane, and are mutually symmetrical with respect to the Y–Z plane (vertical plane containing the finder optical axis Fa).

Other paired light-emitting elements 201c, 201d are respectively symmetrical with paired light-emitting elements (IRED's) 201a, 201b with respect to the Z-X plane. These IRED's 201a–201d are used in pairs, in order to detect the distance between the eyepiece of the camera and the eye 15.

Figure 21:
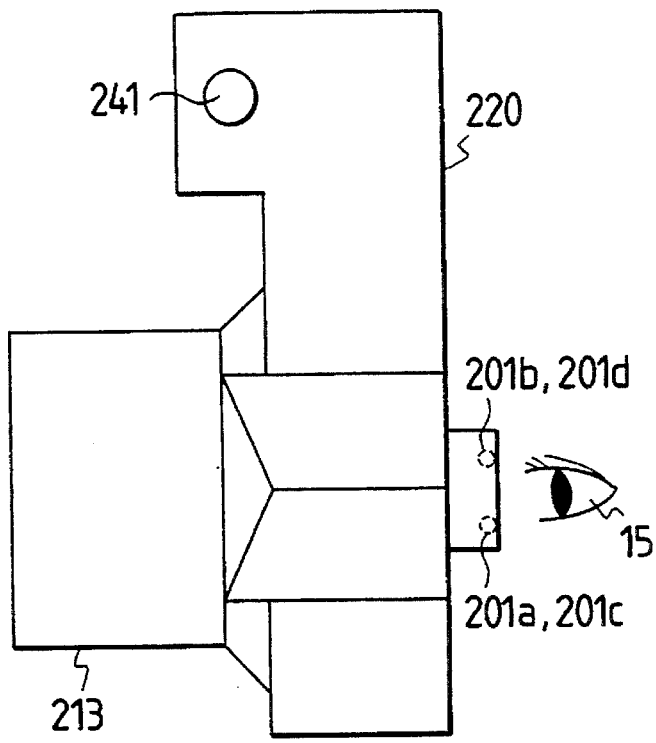
FIG. 21 is a schematic view of the camera shown in FIG. 1 when it is held in a vertical position.

More specifically, based on the position information from the position detecting device 27 (FIG. 1), two IRED's are selected as a set, so as to always illuminate the eye ball 15 of the photographer from the lower side of the eyeball. Thus, when the photographer holds the camera 220 in the normal position, there are selected the elements 201a and 201b. Also when the camera is held in the vertical position with the shutter release button 41 at the top, as shown in FIG. 21, there are selected the light-emitting elements 201a and 201c.

Figure 22:
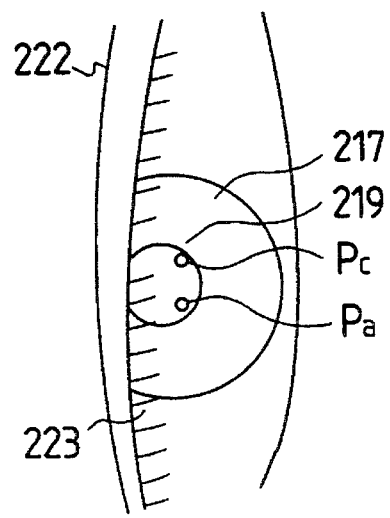
FIG. 22 is a schematic view of the image of the eyeball in the state shown in FIG. 21.
Figure 23:
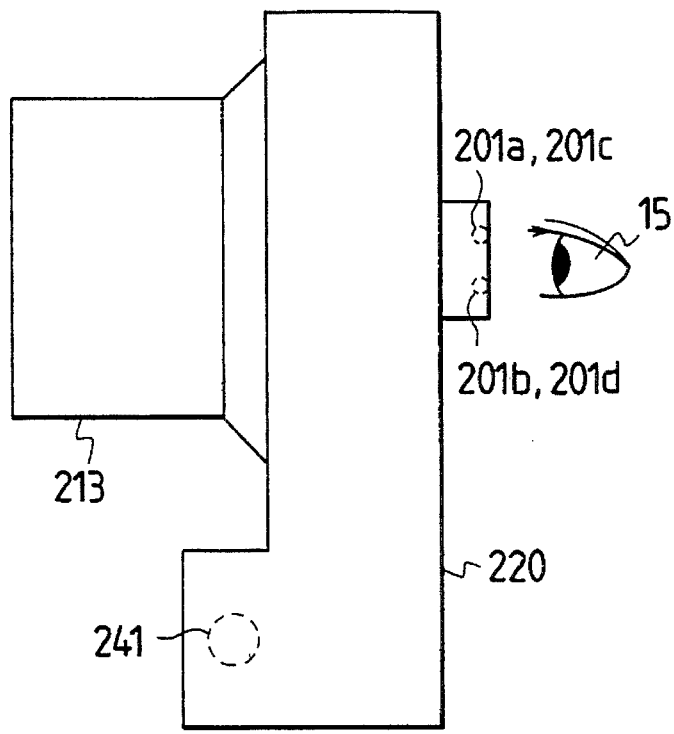
FIG. 23 is a schematic view of the camera shown in FIG. 1 when it is held in a vertical position.
Figure 24:
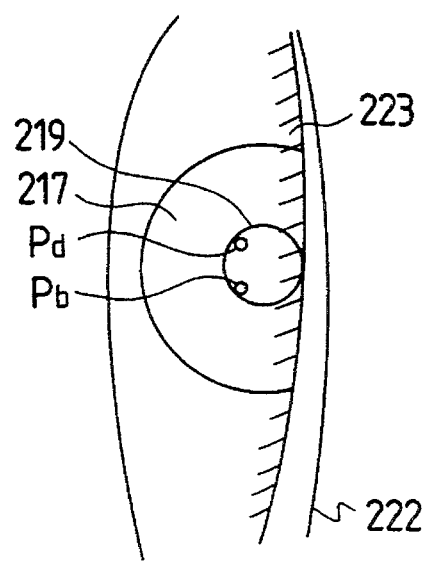
FIG. 24 is a schematic view of the image of the eyeball in a state shown in FIG. 23.

FIG. 22 shows two corneal reflected images Pa, Pc formed on the eye ball 15 in this state. Also, in case of the vertical position of the camera with the shutter release button positioned close to the ground, as shown in FIG. 23, there are selected the light-emitting elements 201b and 201d. FIG. 24 shows two corneal reflected images (Pulkinye I images) formed on the eyeball 15 in this state.

In the present embodiment, two corneal reflected images are always formed on the eyeball of the photographer, and the visual axis of the photographer is detected from the positions of said images, in the manner as explained above.

The visual axis detecting device of the present embodiment is composed of a Visual axis detecting optical system, constituted by members 1, 11, 12 and 14 in FIG. 1, and a visual axis calculating device 44 for calculating the visual axis of the photographer. The infrared light emitted from the paired light-emitting elements, selected according to the signal from the position detecting means 27, illuminates the eyeball 15 of the photographer, positioned close to the eyeball point of the view finder system.

The infrared light reflected by the eyeball 15 is reflected by the dichroic mirror 11a, and is converged by the imaging lens 12 to form images on the image sensor 14. The obtained data of the eye image is processed by said visual axis calculating device (a part of the CPU), whereby the visual axis of the photographer is determined.

Based on the signal from said visual axis calculating device, there are conducted displays (for example of light metering area and distance measuring area) in the viewing field of the view finder, and the distance measurement by the focus state detecting device 6 in one of the plural distance measuring areas within the phototaking image frame.

Figure 25:
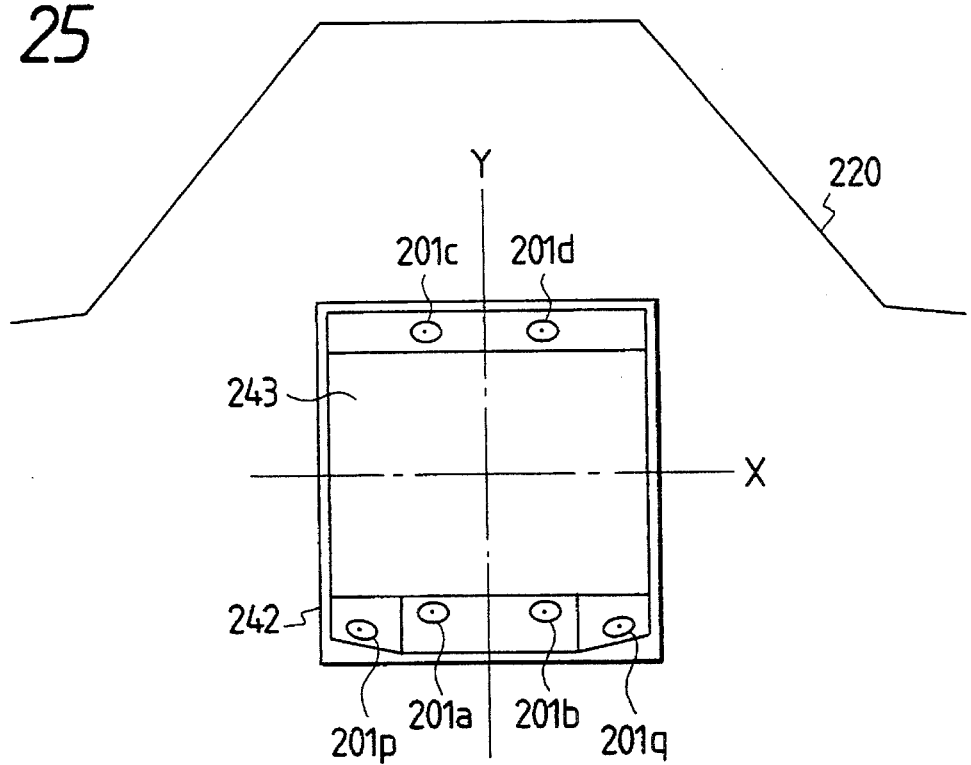
FIG. 25 is a partial schematic view of a second embodiment of the illumination means of the present invention.
Figure 26:
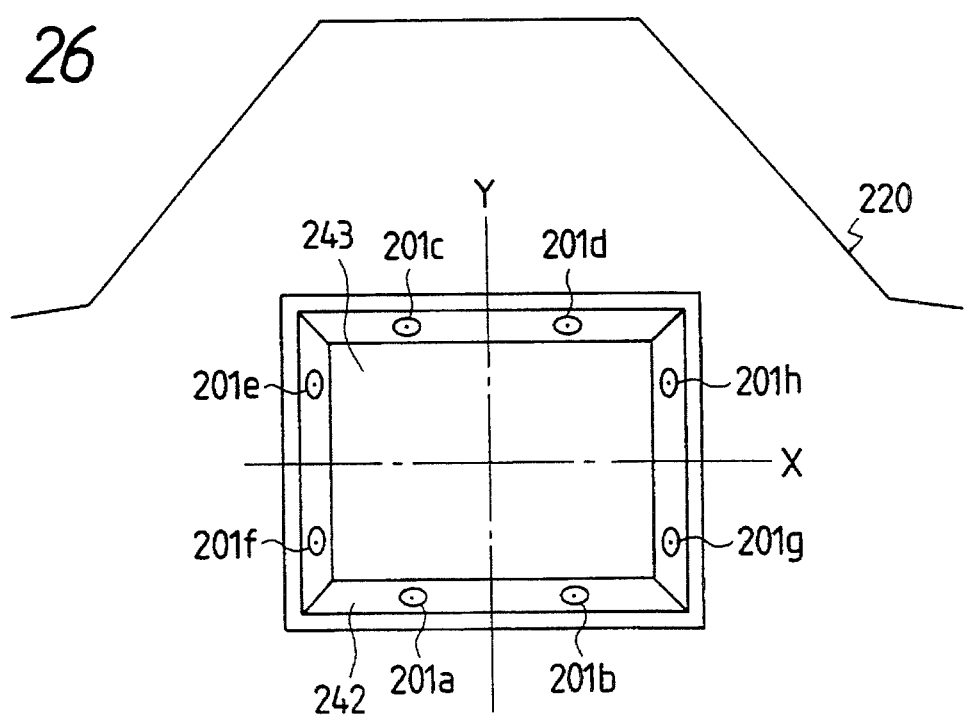
FIG. 26 is a partial schematic view of a third embodiment of the illumination means of the present invention.
Figure 27:
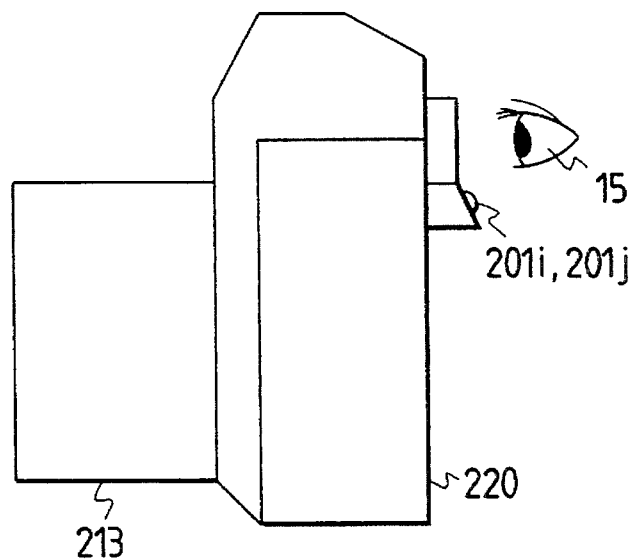
FIG. 27 is a schematic view of the camera when it is held in a normal position.
Figure 28:
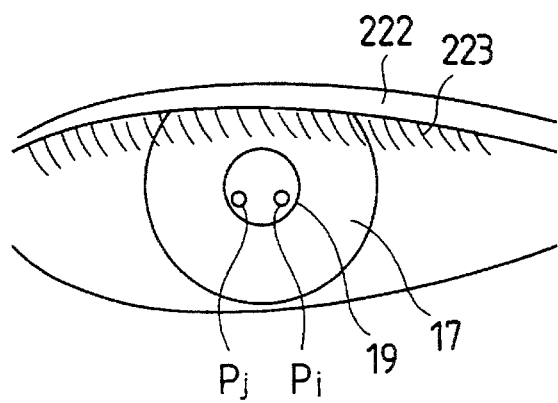
FIG. 28 is a schematic view of the image of the eyeball in a state shown in FIG. 27.
Figure 29:
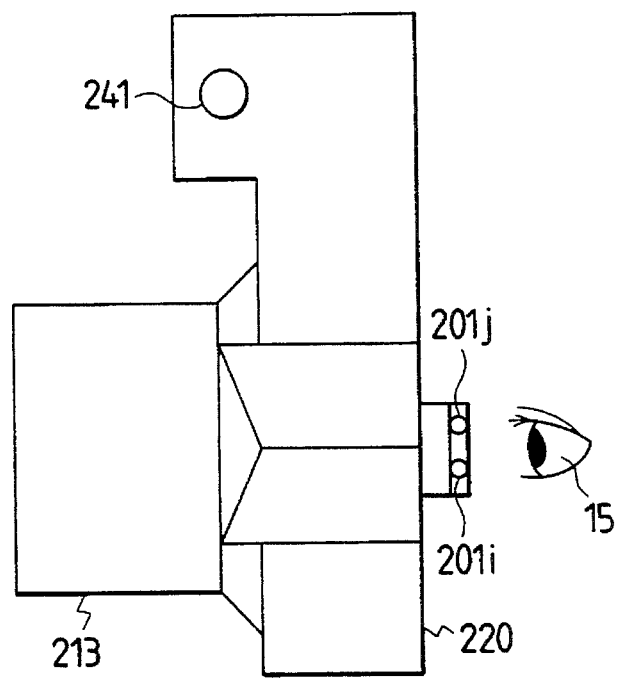
FIG. 29 is a schematic view of the camera when it is held in a vertical position.
Figure 30:
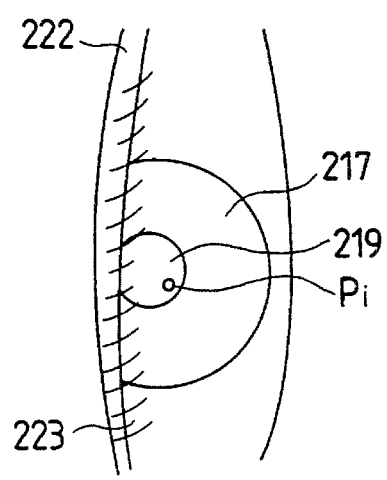
FIG. 30 is a schematic view of the image of the eyeball in a state shown in FIG. 29.
Figure 31:
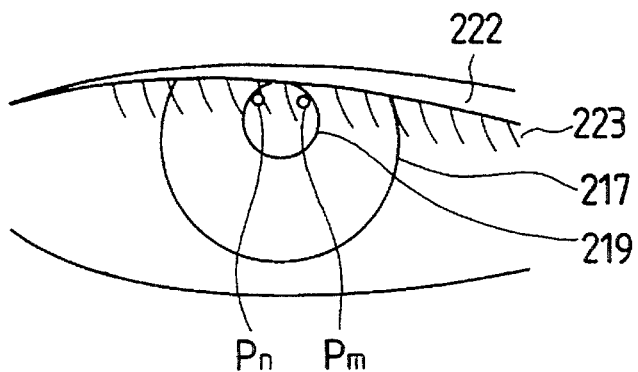
FIGS. 31 to 33 are schematic views of the image of the eyeball.
Figure 32:
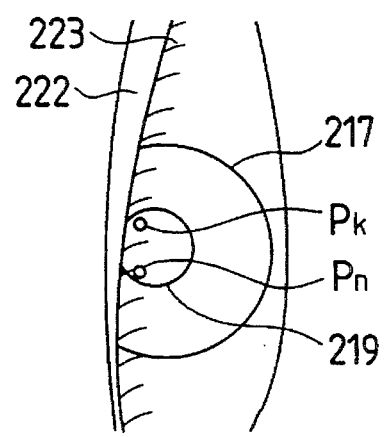
Figure 33:
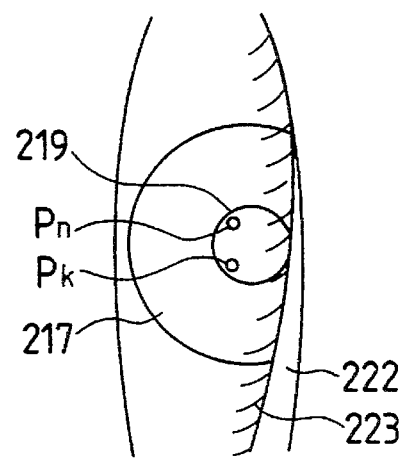

FIGS. 25 and 26 are partical schematic views of second and third embodiments of the illuminating means of the present invention.

In the second embodiment shown in FIG. 25, the illuminating means 1 has 6 light-emitting elements 201a–201d, 201p and 201q, in which 4 elements 201a–201d are positioned in the same manner as in the first embodiment, while the remaining two light-emitting elements 201p, 201q are positioned symmetrically, with respect to the Y–Z plane, with a mutual distance larger than that of the elements 201a, 201b, in order to eliminate the influence of the reflection from the spectacles. Also said elements 201p, 201q are positioned farther from the Z-X plane, than the elements 201a, 201b. These six light-emitting elements 201a–201d, 201p, 201q constitute the illuminating means.

Said paired elements 201p, 201q are selected only when the camera is held in the normal position by the photographer wearing spectacles. Otherwise the light-emitting elements are selected in the same manner as in the first embodiment shown in FIG. 20. When the camera is held in the vertical position by the photographer wearing the spectacles, the reflection from the surface of the spectacles is not a major problem, because the distance of the selected elements is larger.

In the third embodiment shown in FIG. 26, the illumination means 1 has eight light-emitting elements 201a–201h.

In this embodiment, the eight elements 201a–201h are positioned symmetrically with respect to the Z-X plane and the Y–Z plane. Among these elements, a pair is selected according to the following situations.

When the camera is in the normal position, the elements 201a, 201b are selected if the photographer does not wear spectacles, but the elements 201f, 201g are selected if the photographer wears spectacles. When the camera is held in the vertical position, with the shutter release button 241 at the top, the elements 201e, 201f are selected if the photographer does not wear spectacles, but the elements 201c, 201a are selected if the photographer wears spectacles. On the other hand, when the camera is vertically held with the shutter release button 241 close to the ground, the elements 201g, 201h are selected if the photographer does not wear spectacles, but the elements 201b, 201d are selected if the photographer wears spectacles.

Also in this embodiment, a layout without the light-emitting elements 201c, 201d is also feasible. In this case, the light-emitting elements 201f, 201g are selected when the camera is held in the normal position and if the photographer wears spectacles, but, in other situations, when the photographer wears spectacles, the light-emitting elements selected are same as those when the photographer does not wear spectacles.

In the first, second and third embodiments, as explained in the foregoing, at least a pair of light-emitting elements for illuminating the eyeball of the photographer is provided in symmetrical positions with respect to the horizontal plane containing the optical axis of the view finder and the vertical plane containing the optical axis of said view finder, in the normal position of the camera, in order to form at least two corneal reflected images of the light-emitting elements on the eyeball of the photographer, whereby the visual axis of the photographer can be precisely detected regardless whether the camera is held in the normal position or in the vertical position with the shutter release button at the top or near the ground.

Figure 34:
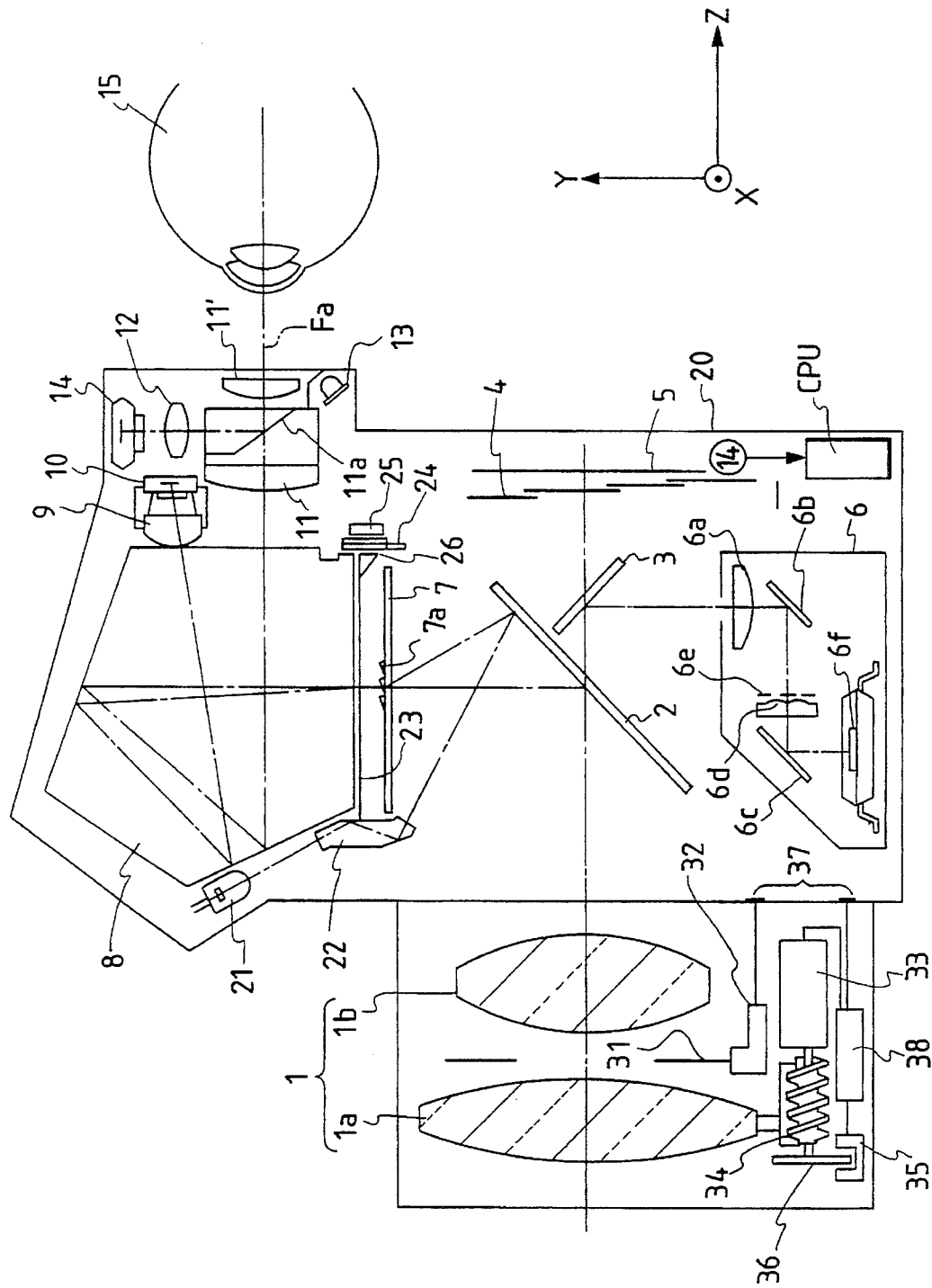
FIG. 34 is a partial schematic view of a fourth embodiment of the present invention applied to a single lens reflex camera.
Figure 35:
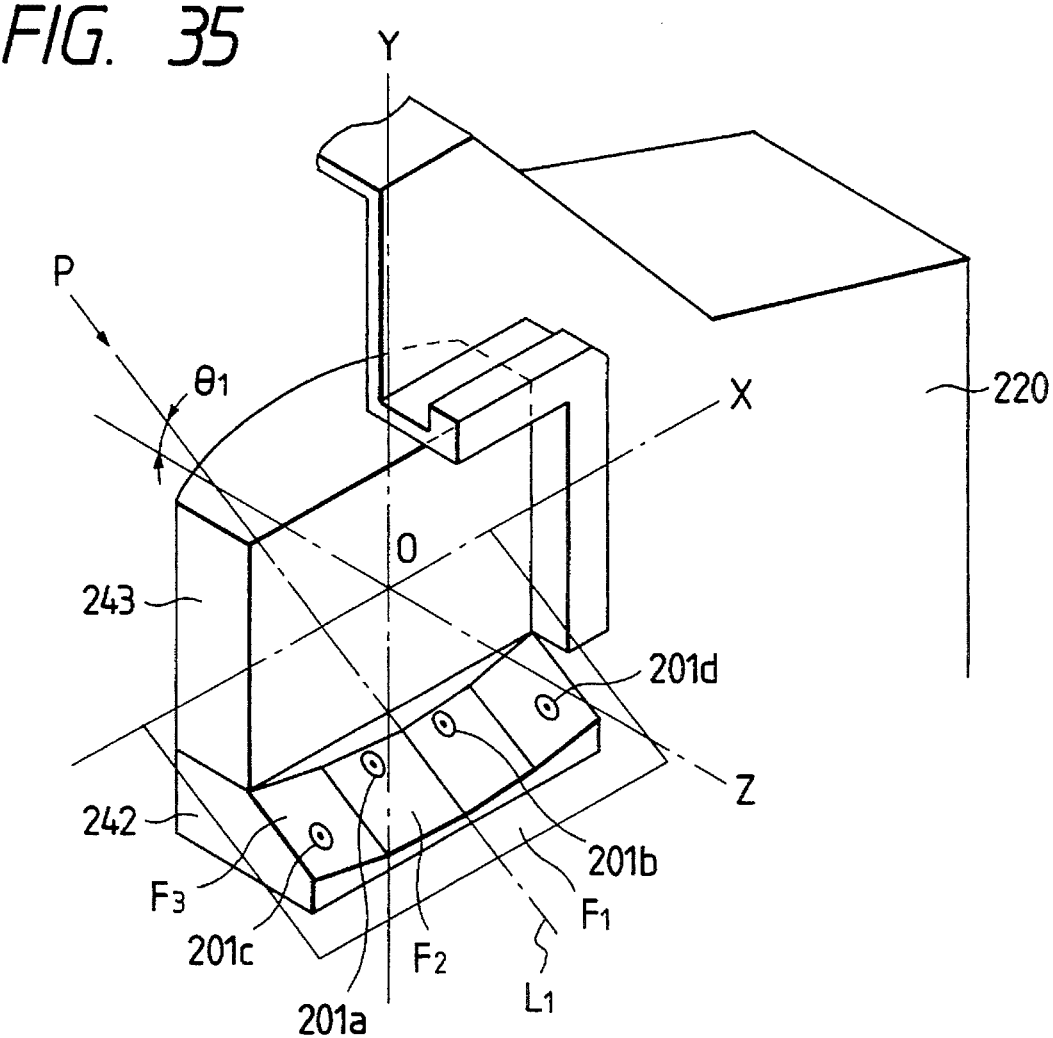
FIGS. 35 to 37 are partial schematic view of the camera shown in FIG. 34.
Figure 36:
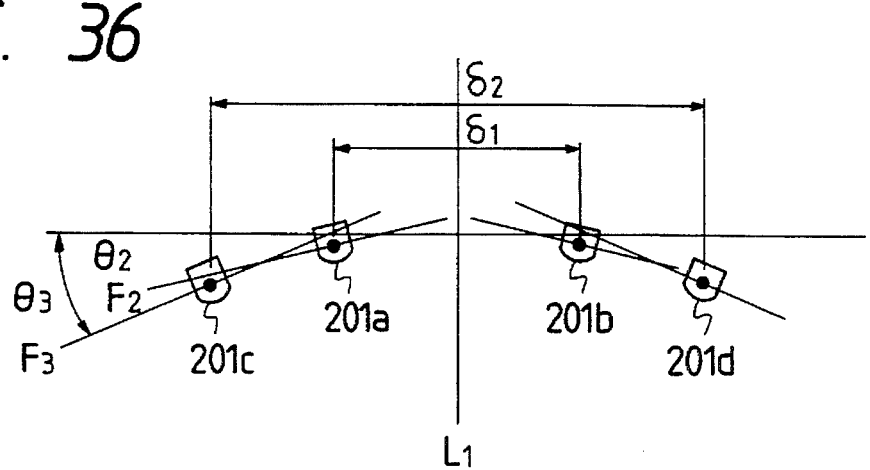

FIG. 34 is a partial schematic view of a fourth embodiment of the present invention applied to a single lens reflex camera, FIG. 35 is a partial magnified view of FIG. 34, and FIG. 36 is a partial schematic view of FIG. 35.

Figure 46:
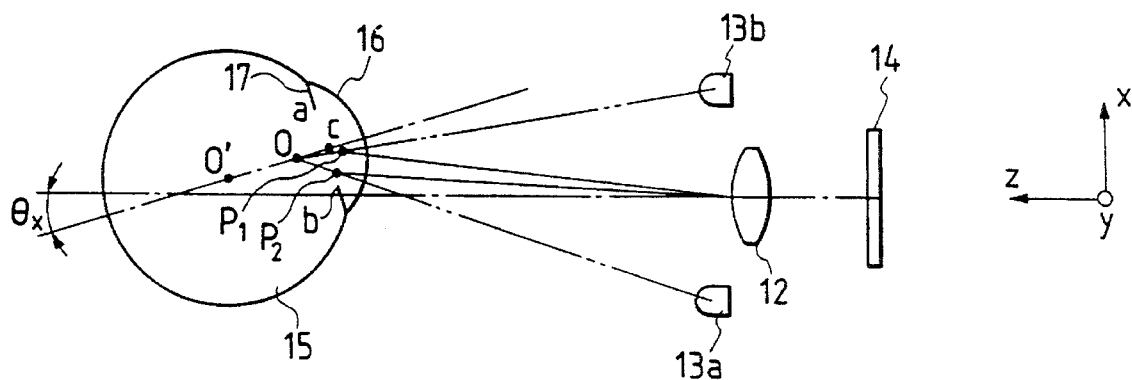
FIG. 46 is a partial schematic view of a conventional visual axis detecting device.
Figure 47A:
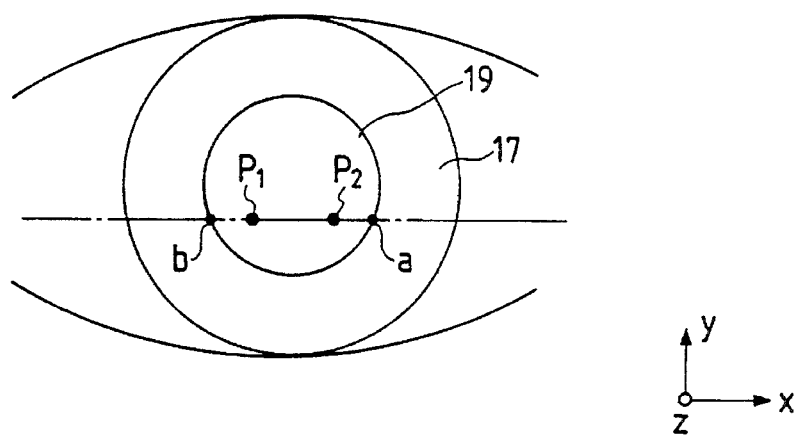
FIGS. 47A and 47B are respectively a view of the eyeball image and a view of the output signal from the image sensor in the device shown in FIG. 46.
Figure 47B:
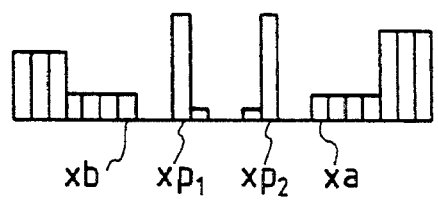
Figure 48:
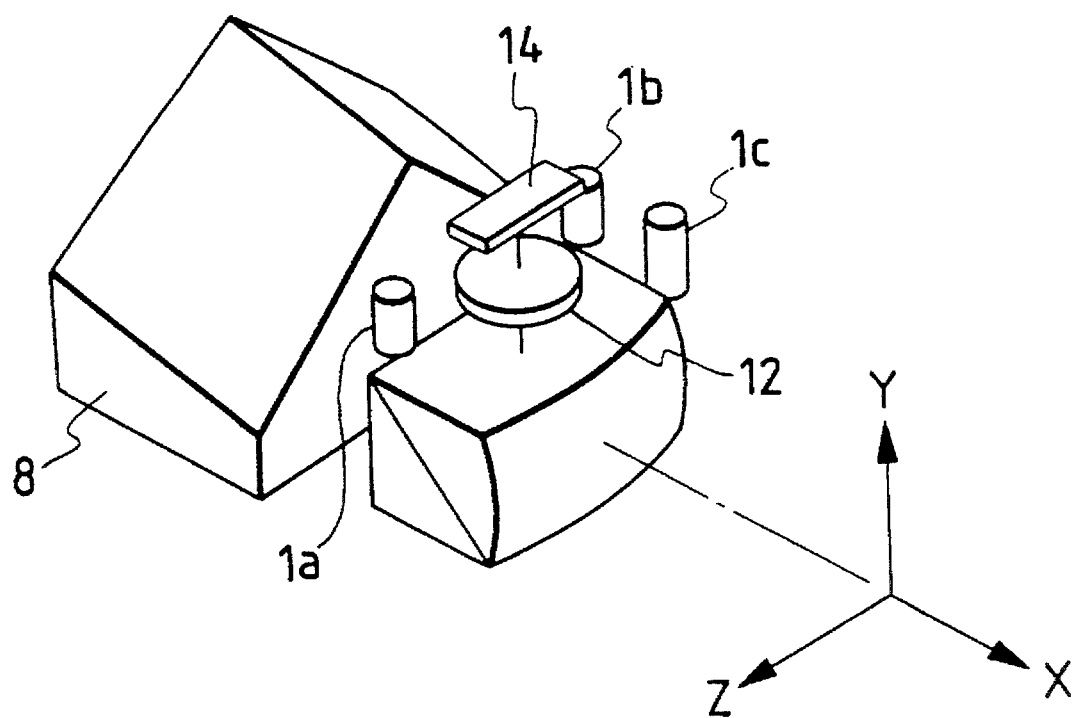
FIG. 48 is a perspective view of the conventional visual axis detecting device in the vicinity of the illumination means.

The configuration of FIG. 34 is different from that of the first embodiment in that the arrangement of the plural light-emitting elements (13a–13d) constituting the illuminating means 1 is different, and that the position detecting means for detecting the camera position is dispensed with, but other structures are substantially same. Also the detecting method of the visual axis of the photographer is basically same as that explained in FIG. 46.

In the following there will be explained the features of the present embodiment, with emphasis on the difference from the first embodiments.

The illuminating means 13 is composed of plural light-emitting elements, such as infrared light-emitting diodes (IRED), illuminating the eyeball of the observer to be subjected to the detection of the visual axis.

As in the first embodiment, when the camera is in the normal position, the original point is taken at the crossing point of the optical axis Fa of the view finder and the exit surface of the eyepiece lens 11', and the Z-axis is defined as the optical axis Fa of the view finder, the Y-axis is defined as a vertical axis, and the X-axis is defined as an axis perpendicular to the Y- and Z-axes. Also a plane F1 is defined as inclined by an angle $\theta 1$ to the Z-X plane and parallel to the X-axis, and the crossing line of the plane F1 and the Y-Z plane is defined as L1.

Figure 37:
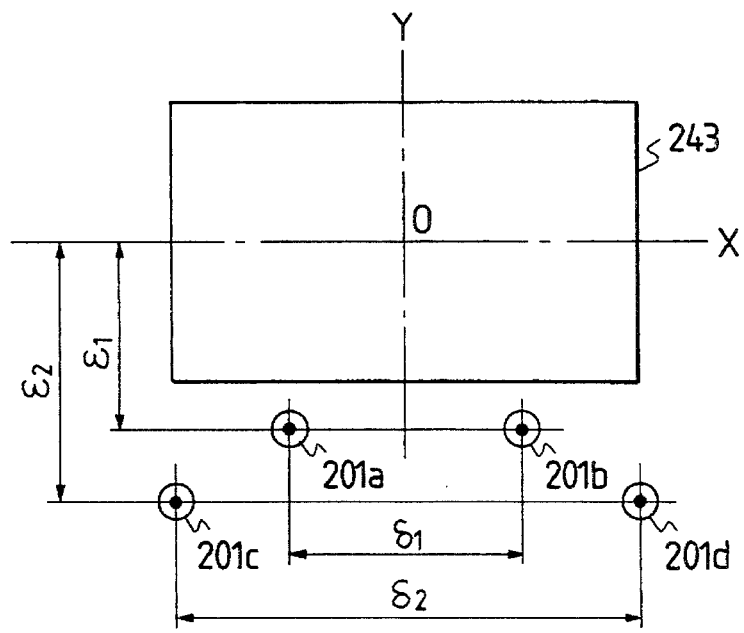

As shown in FIGS. 35 to 37, an IRED 201a is positioned on a plane F2 which is inclined by an angle $\theta 2$ to the plane F1 and parallel to the line L1, and an IRED 201c is positioned on a plane F3 which is inclined by an angle $\theta 3$ to the plane F1 and parallel to the line L1. Also IRED's 201b, 201d are positioned respectively symmetrically with the IRED's 201a, 201c, with respect to the Y–Z plane.

Also the IRED's 201a, 201b are separated by a distance $\delta 1$ while the IRED's 201c, 201d are separated by a distance $\delta 2$. The distance of the IRED's 201a, 201b from the Z-X plane is $\epsilon 1$, while that of the IRED's 201c, 201d from the Z-X plane is $\epsilon 2$. In this state, the positional relationships of the IRED's 201a–201d satisfy following three conditions:

$$\delta 1 < \delta 2, \epsilon 1 < \epsilon 2, \theta 1 < \theta 2.$$

These IRED's 201a–201d are used pairs, in order to detect the distance between the eyepiece of the apparatus and the eyeball 15. Said distance can be detected from the distance of the two corneal reflected images, obtained from the output of the image sensor 14, based on a fact that the distance of two images of IRED's reflected by the cornea of the eyeball 15 is a function of said distance. Then the IRED's 201a, 201b or 201c, 201d are selected and turned on respectively if thus determined distance is smaller or larger than a threshold value, for example 15 mm.

Also the IRED's 201c, 201d or 201a, 201b are selected respectively if the observer wears the spectacles or not. Such selection may be directly entered by the observer, or may be made by the apparatus, based on the automatic discrimination whether the spectacles are worn or not.

Also as the distance between the apparatus and the eyeball of the observer when the observer wears spectacles can be approximately determined, it is also possible to discriminate, from said distance, whether the observer wears spectacles.

Figure 38:
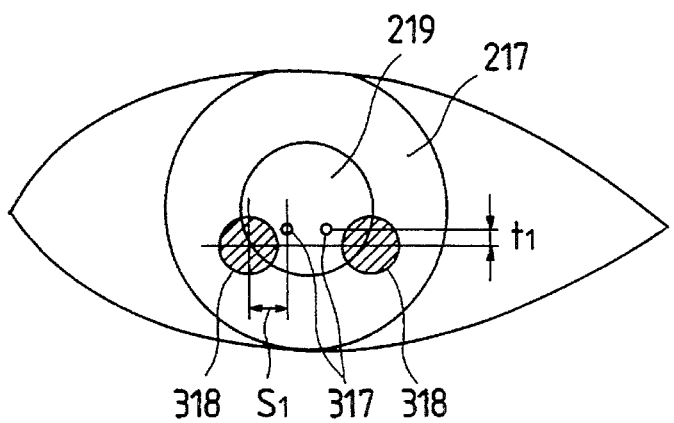
FIGS. 38 and 39 are schematic views of the image of the eyeball in the camera shown in FIG. 34.

FIG. 38 is a schematic view of the eye image of the observer when the observer with the spectacles looks at the view finder while the IRED's 201a, 201b for the observer without the spectacles are turned on. There are shown corneal reflected images 317, reflected lights 318 from the spectacle surface, an iris 217, and a pupil 219.

As will be apparent from FIG. 38, the corneal reflected images 317 and the boundary of the pupil 219 and the iris 217, required for the detection of the visual axis, can be easily hindered by the strong reflected lights from the surface of the spectacles.

Figure 39:
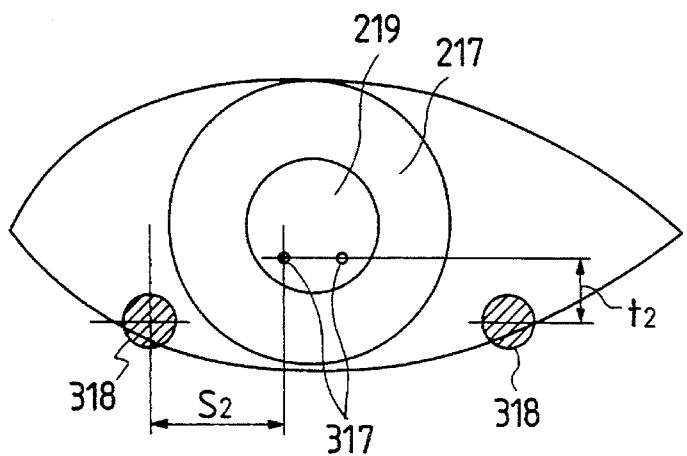

FIG. 39 is a schematic view of the eye image under the same condition as in FIG. 38, while the IRED's 201c, 201d for the observer with the spectacles are turned on.

Figure 40:
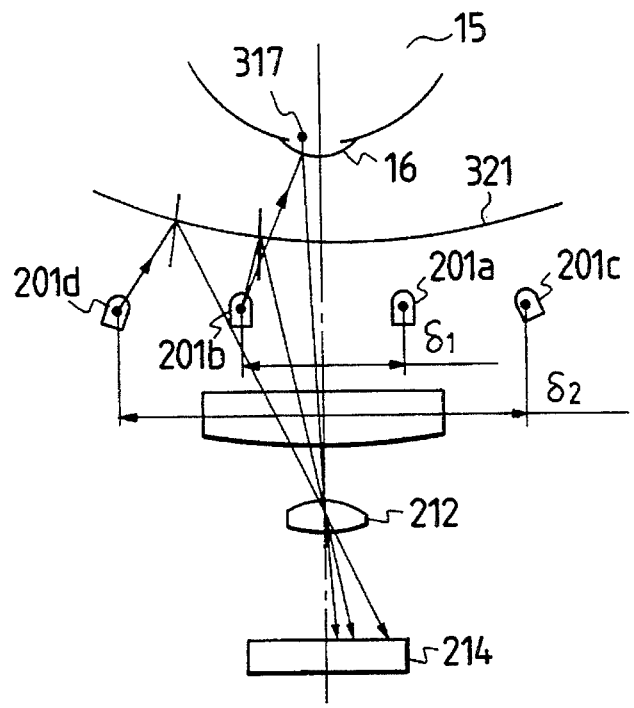
FIGS. 40 to 42 are partial schematic views of the camera shown in FIG. 34.
Figure 41:
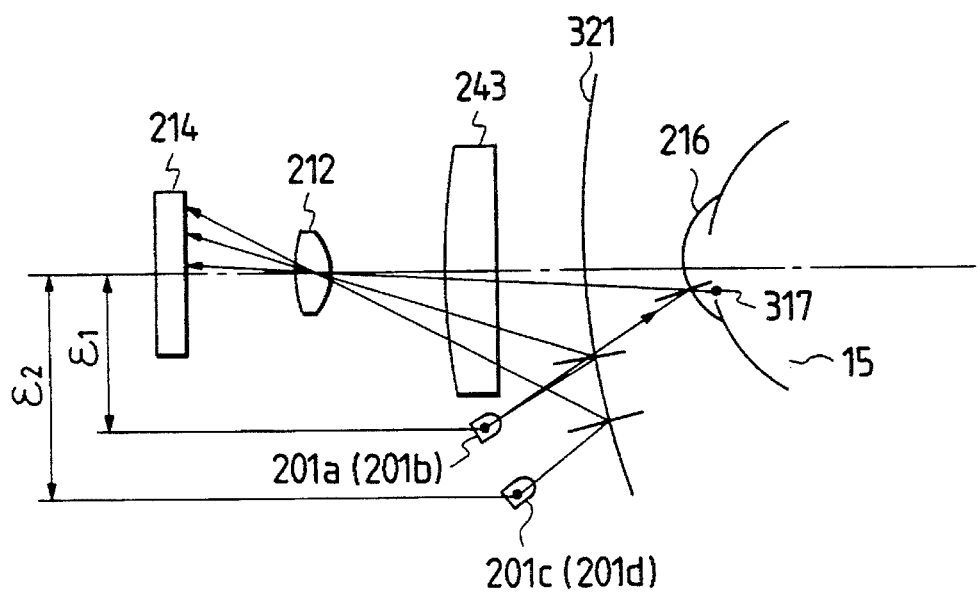

As will be apparent from FIG. 39, the distance between the lights 318 of the IRED's 201c, 201d reflected by the surface of the spectacles and the corneal reflected images 317 is enlarged in the horizontal and vertical directions, whereby satisfactory information on the eye images can be obtained. The increased distance s of the two reflected lights in the horizontal direction is, as shown in FIG. 40, due to the spreading of the distance of the IRED's from $\delta 1$ to $\delta 2$ (67 $1<\delta 2$). Since the lens of the spectacles is positioned close to the IRED's, the spectacle-reflected lights 318 vary the positions significantly in response to the position change of the IRED's, while the corneal reflected images 317 do not vary the positions too much, because the eyeball 15 is relatively distant from the IRED's and also because the curvature of the cornea 16 is significantly larger than that of the spectacles 321. For this reason, the distance between the spectacle-reflected light 318 and the corneal reflected image 317 increases in relative manner, so that these images can be more easily separated.

Also when the observer wears the spectacles, the distance between the apparatus 220 and the eyeball 15 increases to reduce the distance of the two corneal reflected images 317, so that the precision of determination of the central position of curvature of the cornea becomes deteriorated. This phenomenon is however resolved by a fact that the distance of the corneal reflected images 318 is increased by the increased distance of the light-emitting elements 201a–201d.

Also the distance t of the spectacle-reflected light 318 of the IRED's and the corneal reflected images 317 in the vertical direction is increased because, as in the horizontal direction, the IRED's 201c, 201d for the observer with spectacles are more distant than those 201a, 201b for the observer without spectacles, from the Z-X plane ($\epsilon1 < \epsilon2$).

Also if the eyeball 15 is illuminated with two IRED's of a relative large mutual distance, the image at the center of the eyeball may become dark, due to the directionality of the light emission of the IRED's, so that the detection of the eye image may be hindered.

Figure 42:
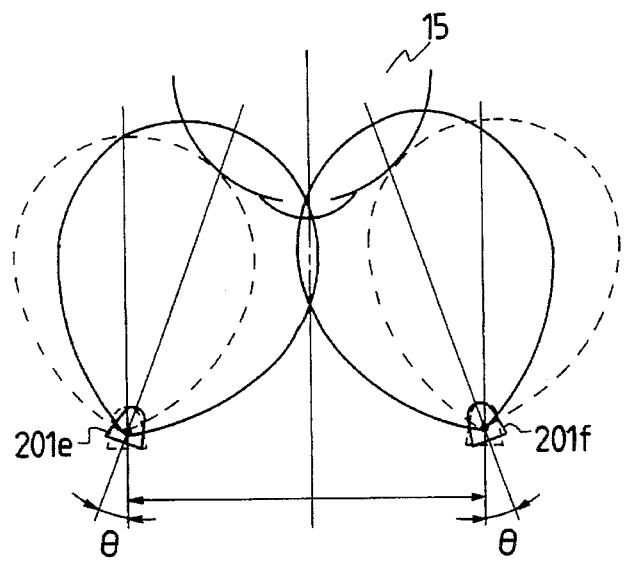

In such situation, by inclining the optical axes of the two IRED's 201e, 201f by a predetermined angle from the center as shown in FIG. 42, the eyeball 15 can be uniformly illuminated. Said angle is increased with the increase in the distance of the IRED's, whereby satisfactory eye image can be detected.

Figure 43:
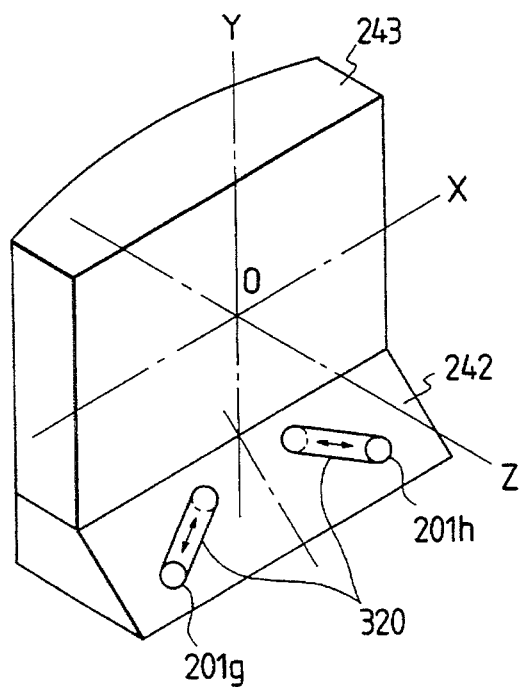
FIG. 43 is a schematic view of a fifth embodiment of the illumination means of the present invention
Figure 44:
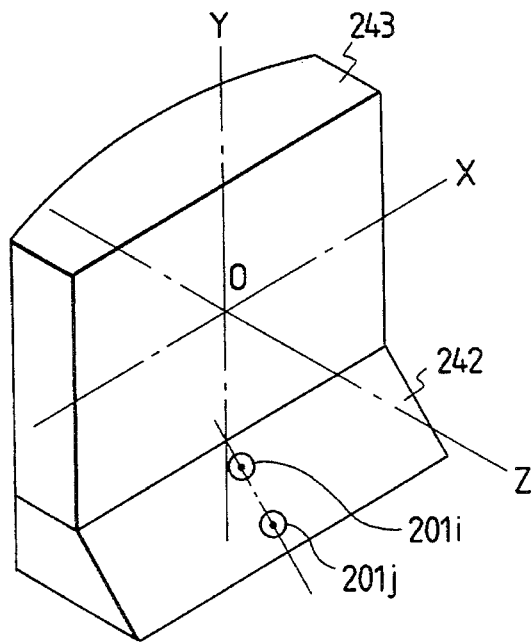
FIG. 44 is a schematic view of a sixth embodiment of the illumination means of the present invention.

FIGS. 43 and 44 are partial schematic view of fifth and sixth embodiments of the illumination means of the present invention.

In the foregoing fourth embodiment, two IRED's are selected and used from four IRED's. In the fifth embodiment shown in FIG. 43, there are employed two IRED's 201g, 201h which are mechanically displaced in position along guide grooves 320, between a position a for the spectacles and a position b without the spectacles, whereby obtained is an effect similar to that in the fourth embodiment.

The sixth embodiment shown in FIG. 44 employs an IRED's for illuminating the eyeball of the observer, in order to detect the visual axis. In this method the distance between the eyeball and the apparatus cannot be identified, but the visual axis detection is possible though with a relatively rough precision by setting average values for the observer with and without spectacles. In this embodiment, an IRED 201i for the observer with the spectacles and an IRED 201j for the observer without the spectacles are positioned with respective distances $\epsilon3$ and $\epsilon4$ ($\epsilon3$ $\epsilon4$) from the Z-X plane, so that the spectacle-reflected images of the IRED's are separated from the eyeball only in the vertical direction.

In the fourth, fifth and sixth embodiments, in the detection of the visual axis of the observer from the eye image information of the observer looking into an object, said eyeball is illuminated with the light-emitting elements of different positions according to the distance between the eyeball and the apparatus or according to whether the observer wears the spectacles or not, whereby the positions of the corneal reflected images of the observer, and the position of the visual axis of said observer, can be determined with satisfactory precision.

Also the positions of illumination are changed to vary the positions of reflected lights of the light-emitting elements on the surface of the spectacles worn by the observer, thereby clearing separating the reflected lights from the eye image, whereby satisfactory eye image information can be obtained even when the observer wears spectacles and the visual axis can be detected with high precision.

The foregoing embodiments have been limited to the application to a single lens reflex camera employing the silver halide-based film, but the present invention is likewise applicable to a video camera. In such case, the view finder is to look at the image frame of a small cathode ray tube or a liquid crystal display device. The visual axis detecting device of the present invention is also applicable to a microscope for manufacturing purpose or to various observing apparatus. Said visual axis detecting device is furthermore applicable, in addition to the selection of the focus state detecting area, to the selection of the light metering pattern or the selection of various operation modes by the visual axis in optical apparatus.

Figure 45B:
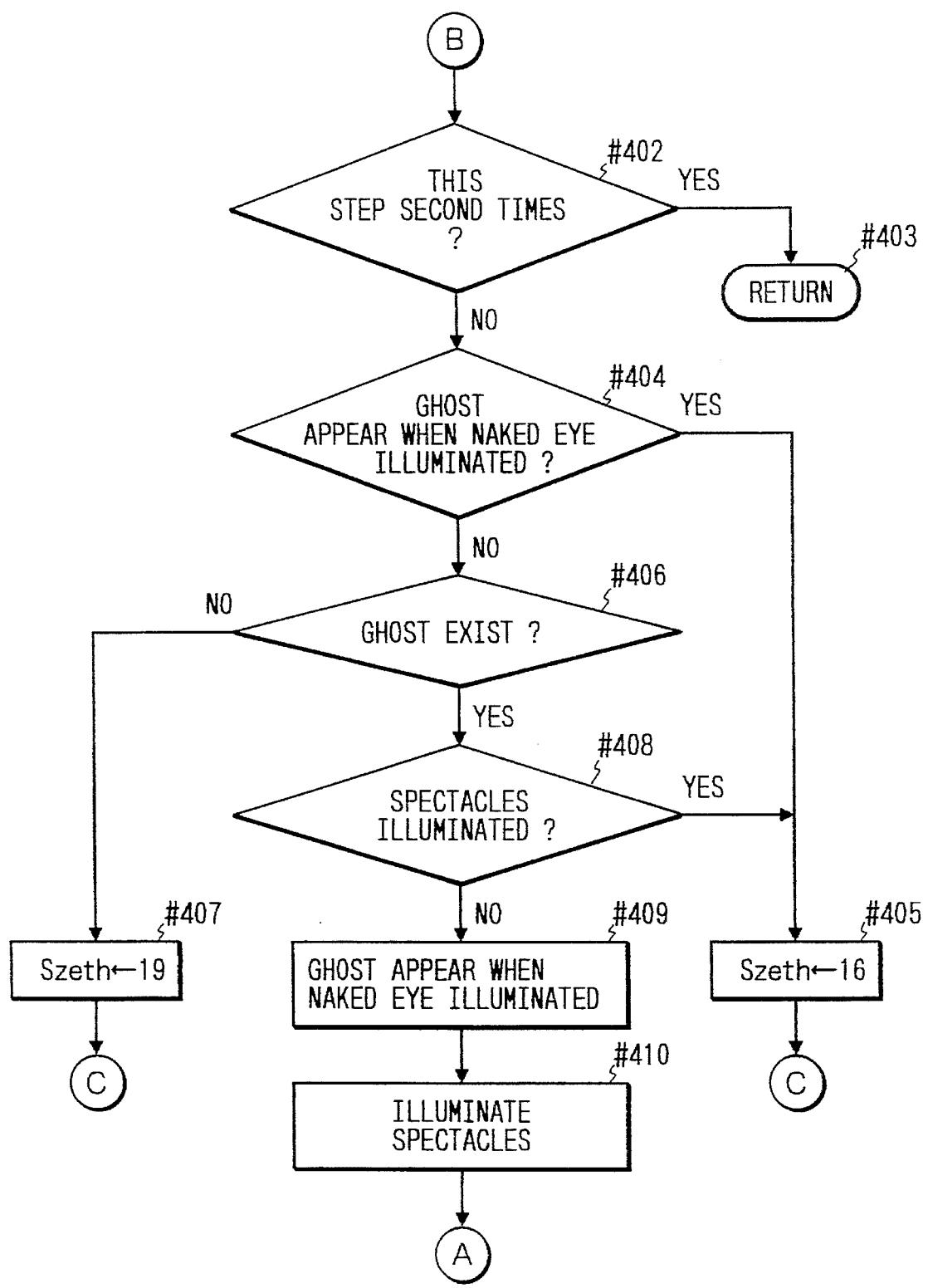
FIG. 45, comprised of FIGS. 45A to 45C, is a flow chart showing the method for setting illumination in a seventh embodiment of the present invention.
Figure 45C:
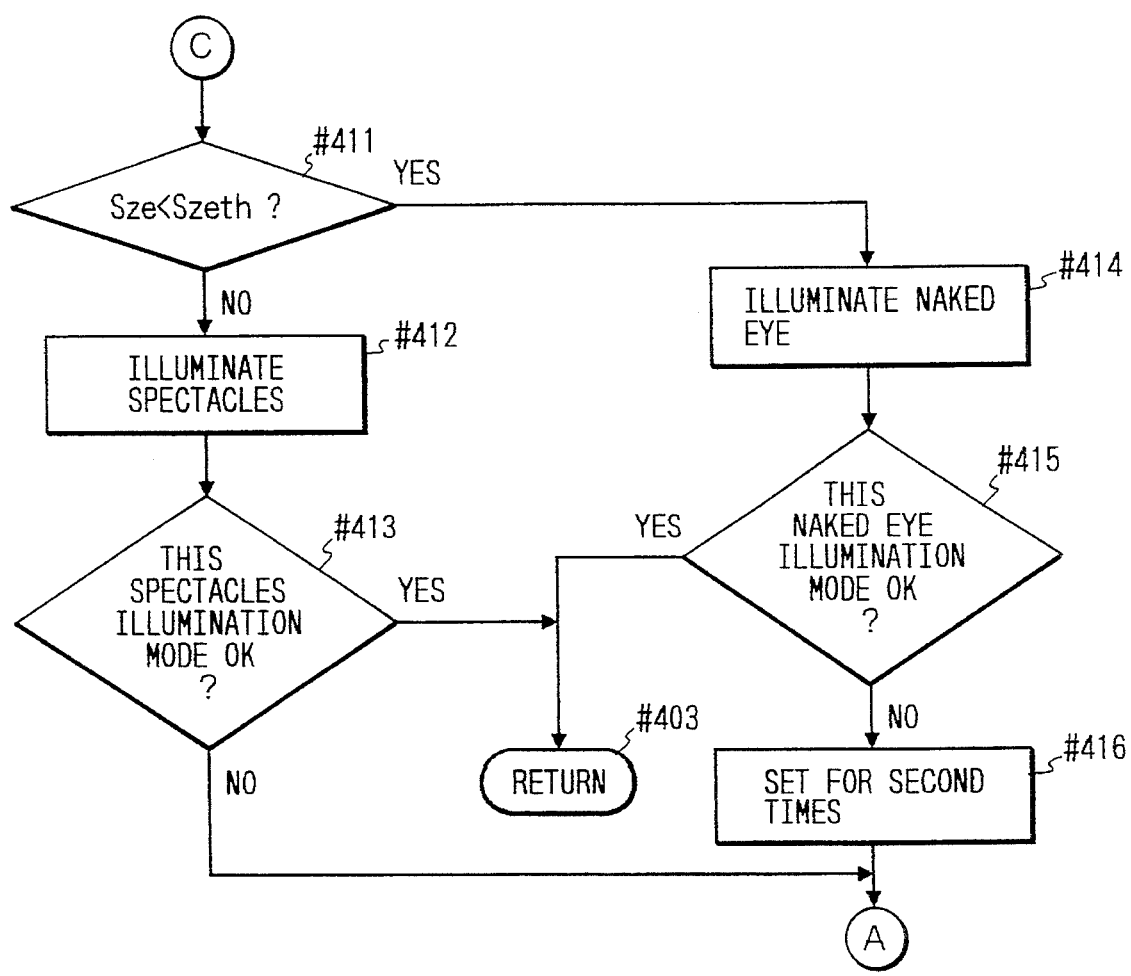

In the following there will be explained, with reference to a flow chart shown in FIG. 45, a method of setting the illumination for the eyeball of the observer, in a seventh embodiment of the present invention. As in the flow chart for the visual axis calibration shown in FIG. 11A, there is discriminated whether the observer wears the spectacles (#338), prior to the visual axis detection for obtaining the calibration data for the visual axis.

At first the visual axis detecting circuit 101 shown in FIG. 6 sends a signal to the IRED driving circuit 107 to turn on the IRED's 13a, 13b for the eyeball without spectacles, thereby illuminating the eyeball of the observer (#400). Subsequently the visual axis detecting circuit 101 executes the detection of the visual axis of the observer (#104), according to the flow shown in FIG. 10A. When the visual axis detection is successfully made (#401), there is discriminated whether this judging routine is the first or second cycle (#402). The judging routine (first cycle) whether the observer wears the spectacles basically consists of a visual axis detection with the illumination for the eyeball without spectacles and a visual axis detection with the illumination for the eyeball with spectacles. After said two visual axis detections, if the judging routine is the second cycle, the sequence returns to the visual axis calibration routine (#314 in FIG. 11) with the currently selected illumination method (#403).

On the other hand, if the judging routine is the first cycle instead of second one (#402), reference is made to the flag indicating the generation of ghost when the eyeball is illuminated with the IRED's for the eyeball without spectacles (#404). If said flag is set (#404), the threshold value Szeth for the distance of the eyeball (distance between the top of the cornea and the exit plane of the eyepiece lens), for selecting the illumination for the eyeball without spectacles and the illumination for the eyeball with spectacles is selected at 16 mm (#405). On the other hand, if said flag indicates the absence of ghost (#404), there is checked whether ghost was generated in the latest visual axis detecting operation (#406). If not (#406), the observer is probably without the spectacles, so that the threshold value Szeth for the eyeball distance is selected at 19 mm (#407). If the ghost is generated in the latest visual axis detecting operation, there is checked whether the IRED's used for illumination are for the eyeball with spectacles (#408). If the ghost is generated in the latest visual axis detecting operation with the illumination by the IRED's for the eyeball without spectacles (#408), the visual axis detecting circuit 101 sets a flag indicating the ghost generation in case of illumination of the eyeball with the IRED's for the eyeball without spectacles (#409), then varies the IRED's to those for the eyeball with spectacles (#410), and executes the visual axis detection (#104).

In case the ghost is generated in the latest visual axis detection operation with the illumination by the IRED's for the eyeball with (#408), the observer is probably wearing, so that the threshold value Szeth for the eyeball distance is set at the smaller value, 16 mm (#405). After said threshold setting, there is executed comparison with the eyeball distance Sze at the latest visual axis detection (#411). If the eyeball distance Sze is smaller than the threshold value Szeth (#411), the observer is estimated to be without the spectacles, and there are selected the IRED's for the eyeball without spectacles (#414). If the eyeball is illuminated with the IRED's for the eyeball without spectacles in the latest visual axis detecting operation, the illuminating condition coincides with that selected in the immediately preceding step #414, so that the illuminating method is confirmed to be correct. Thus the setting of the illuminating method is completed, and the sequence returns to the visual axis calibrating routine (#403). On the other hand, if the illumination in the latest visual axis detecting operation is with the IRED's for the eyeball with spectacles and does not coincide with the illuminating condition (for the eyeball without spectacles) selected in the step #414, (#415), there is set a flat indicating the second judging routine (#416), and the visual axis detection is executed again (#104).

Also if the eyeball distance Sze is equal to or larger than the threshold value Szeth (#411), said large eyeball distance is presumably due to a fact that the observer wears spectacles, and the IRED's for the eyeball with spectacles are selected (#412). If the eyeball is illuminated with the IRED's for the eyeball with spectacles in the latest visual axis detecting operation, the illuminating condition coincides with that selected in the step #412, so that the illuminating method is confirmed to be corrected. Thus the setting of the illuminating method is completed, and the sequence returns to the visual axis calibrating routine (#403). On the other hand, if the eyeball is illuminated with the IRED's for the eyeball without spectacles in the latest visual axis detecting operation, the illuminating condition does not coincide with that (for the eyeball with spectacles) set in the step #412 (#413), the visual axis detection is executed again (#104).

When the visual axis detection is effected (#104) and if said detection fails (#401), there is discriminated whether said failed visual axis detection was conducted with illumination by the IRED's for the eyeball without spectacles (#417). If so (#417), the illumination is changed to the IRED's for the eyeball with spectacles (#418), and the visual axis detection is executed again (#104). On the other hand, if the failed visual axis detection was conducted with the IRED's for the eyeball with spectacles (#417) and if said visual axis detection was the second cycle (#419), the illumination method is regarded not identifiable, and a corresponding flag is set (#412). Then the sequence returns to the visual axis calibrating routine (#403). In such case, since the visual axis calibration cannot be continued, the sequence jumps to a step #337 in FIG. 11, for generating an alarm sound and providing a display indicating that the calibration is not attained.

On the other hand, if the visual axis detection fails with the illumination for the eyeball with spectacles (#417) but if the judging routine for the illuminating method is in the first cycle, there are selected the IRED's for the eyeball without spectacles. Then there is set a flag indicating the second cycle of the judging routine (#420), and the visual axis detection is executed again (#104).

In the foregoing, the present invention has been explained by applications to a single lens reflex camera, but the present invention is likewise applicable to a lens shutter camera, a video camera or other observation apparatus.

What is claimed is:

1. An optical apparatus comprising:
    illumination means for illuminating an eyeball, including a movable light source;
    light-receiving means for receiving light reflected from the eyeball and converting the light into an electrical signal;
    signal forming means for forming a signal indicating a visual axis of the eyeball, based on the electrical signal; and
    means for displacing said light source.

2. A visual axis detecting device for illuminating an eyeball of a photographer looking into a view finder system, with illumination means, receiving light reflected from the eyeball with light-receiving means, and calculating a visual axis of the photographer by calculation means by using an output signal from said light-receiving means, comprising:
    illumination means including plural light-emitting elements for illuminating the eyeball from off-axial positions with respect to an optical axis of said view finder system;
    distance detecting means for detecting a distance between said view finder system and the eyeball of the photographer; and
    control means for turning on predetermined light-emitting elements among the plural light-emitting elements according to a signal from said distance detecting means.

3. A visual axis detecting device according to claim 2, wherein the plural light-emitting elements are composed of plural pairs of light-emitting elements positioned symmetrically with respect to a vertical plane including the optical axis of said view finder system when said device lies in a normal position, and said paired light-emitting elements have respectively a different distance.

4. A visual axis detecting device according to claim 2, wherein the plural light-emitting elements are composed of plural pairs of light-emitting elements positioned symmetrically with respect to a vertical plane including the optical axis of said view finder system when said device lies in a normal position, and said plural pairs of the light-emitting elements are respectively positioned at different distances from a horizontal plane including the optical axis of said view finder system, when said device lies in a normal position.

5. A visual axis detecting device according to claim 2, wherein the plural light-emitting elements are composed of plural pairs of light-emitting elements positioned symmetrically with respect to a vertical plane including the optical axis of said view finder system when said device lies in a normal position, and the angle formed by projecting a central axis of light beams from the light-emitting elements of each pair onto a horizontal plane including the optical axis of said view finder system when the device lies in a normal position is respectively different in each of the plural pairs of the light-emitting elements.

6. A visual axis detecting device for illuminating an eyeball of a photographer looking into a view finder system, with illumination means, receiving light reflected from the eyeball with light-receiving means, and calculating a visual axis of the photographer by calculation means with an output signal from said light-receiving means, comprising:
    illumination means including plural light-emitting elements for illuminating the eyeball from off-axial positions with respect to an optical axis of said view finder system;
    spectacles detecting means for detecting whether the photographer wears spectacles; and
    control means for turning on predetermined light-emitting elements among the plural light-emitting elements according to a signal from said spectacle detecting means;
    wherein the plural light-emitting elements are composed of plural pairs of light-emitting elements positioned symmetrically with respect to a vertical plane including the optical axis of said view finder system when said device lies in a normal position, and the angle formed by protecting a central axis of light beams from the light-emitting elements of each pair onto a horizontal plane including the optical axis of said view finder system when the device lies in a normal position is respectively different in each of the plural pairs of the light-emitting elements.

7. A visual axis detecting device comprising:

illumination means for illuminating an eyeball of a photographer;

light-receiving means for receiving light reflected from a frontal portion of the eyeball of the photographer; and calculation means for calculating a visual axis of the photographer from an eye image obtained by said light-receiving means;

wherein said calculation means includes judgment means for judging whether the photographer wears spectacles based on the presence or absence of a ghost in the eye image and the distance from the eyeball of the photographer to said device.

8. A visual axis detecting device according to claim 7, wherein said calculation means is adapted to detect whether a ghost appears in the eye image obtained by said light-receiving means and to change, according to the presence or absence of the ghost, a threshold value relative to the distance from the eyeball of the photographer to the device, in order to judge whether the photographer wears spectacles or not.

9. An apparatus for detecting a visual axis of an eye of a person, said apparatus comprising:

illuminating means for illuminating the eye of the person with light from a plurality of different illuminating positions;

detecting means for detecting light from the eye; and controlling means for discriminating whether or not the person is wearing spectacles on the basis of output of said detecting means and for controlling said illuminating means in accordance with the discrimination result, wherein said controlling means discriminates whether or not the person is wearing spectacles by detecting whether or not a signal representative of reflection light from the spectacles is included in the output of said detecting means.

10. An apparatus according to claim 9, wherein said controlling means further discriminates whether or not the person is wearing spectacles on the basis of a distance between a pair of images of light reflected by a cornea of the eye in the output of said detecting means.

11. An apparatus according to claim 9, wherein said controlling means changes a light illuminating position of said illuminating means in accordance with the discrimination result.

12. An apparatus according to claim 11, wherein said illuminating means comprises:

a first pair of illuminating positions symmetrically with respect to an optical axis of said detecting means; and a second pair of illuminating positions symmetrically with respect to the optical axis of said detecting means, wherein a distance between the second pair of illuminating positions is greater than a distance between the first pair of illuminating positions, and wherein said controlling means illuminates an eye of the person with light from the first pair of illuminating positions when the person is not wearing spectacles and illuminates the eye of the person with light from the second pair of illuminating positions when the person is wearing spectacles.

13. An apparatus according to claim 12, wherein a light-emitting element is provided at each of the illuminating positions.

14. An apparatus according to claim 12, wherein each of the illuminating positions are selected so that the eye is illuminated with light from a lower side of the eye.

15. An apparatus according to claim 12, wherein said illuminating means directly illuminates the eye of the person with light.

16. An optical apparatus comprising:

illuminating means for illuminating an eye of the person with light from a plurality of different illuminating positions;

detecting means for detecting light from the eye; and controlling means for discriminating whether or not the person is wearing spectacles on the basis of output of said detecting means and for controlling said illuminating means in accordance with the discrimination result, wherein said controlling means discriminates whether or not the person is wearing spectacles by detecting whether or not a signal reflection light from the spectacles is included in the output of said detecting means, said controlling means further detecting a visual axis of the eye of the person on the basis of output of said detecting means based on illumination corresponding to the discrimination result.

17. An apparatus according to claim 16, wherein said controlling means further discriminates whether or not the person is wearing spectacles on the basis of a distance between a pair of images of light reflected by a cornea in the output of said detecting means.

18. An apparatus according to claim 16, wherein said controlling means changes a light illuminating position of said illuminating means in accordance with the discrimination result.

19. An apparatus according to claim 18, wherein said illuminating means comprises:

a first pair of illuminating positions symmetrically with respect to an optical axis of said detecting means; and a second pair of illuminating positions symmetrically with respect to the optical axis of said detecting means, wherein a distance between the second pair of illuminating positions is greater than a distance between the first pair of illuminating positions, and wherein said controlling means illuminates an eye of the person with light from the first pair of illuminating positions when the person is not wearing spectacles and illuminates the eye of the person with light from the second pair of illuminating positions when the person is wearing spectacles.

20. An apparatus according to claim 16, wherein a light-emitting element is provided at each of the illuminating positions.

21. An apparatus according to claim 16, wherein each of the illuminating positions are selected so that the eye is illuminated with light from a lower side of the eye.

22. An apparatus according to claim 16, wherein said illuminating means directly illuminates the eye of the person with light.

23. An apparatus according to claim 16, wherein said controlling means discriminates whether or not the person is wearing spectacles by detecting whether or not a signal representative of reflective light from the spectacles is included in the output of said detecting means.

24. An apparatus according to claim 16, wherein said optical apparatus is a camera.

25. An apparatus according to claim 24, further comprising a finder including an eyepiece lens, wherein the plurality of illuminating positions of said illuminating means are disposed at the periphery of said eyepiece lens.

26. An apparatus according to claim 25, wherein said illuminating means illuminates the eye with light from six illuminating positions.

27. An apparatus according to claim 25, wherein said illuminating means illuminates the eye with light from eight illuminating positions.

28. An apparatus according to claim 25, wherein said illuminating means comprises:

a first pair of illuminating positions symmetrically with respect to a vertical plane including an optical axis of said finder; and a second pair of illuminating positions symmetrically with respect to the vertical plane, wherein a distance between the second pair of illuminating positions is longer than a distance between the first pair of illuminating positions, and wherein said controlling means illuminates an eye of the person with light from the first pair of illuminating positions when the person is not wearing spectacles and illuminates the eye of the person with light from the second pair of illuminating positions when the person is wearing spectacles.

29. An apparatus according to claim 28, wherein a light-emitting element is provided at each of the illuminating positions.

30. An apparatus according to claim 25, further comprising posture detecting means for detecting whether said camera is disposed in a vertical position or a horizontal position, wherein said controlling means changes the illuminating positions of said illuminating means in accordance with detection by said posture detecting means of a state where said camera is disposed in the vertical position or a state where said camera is disposed in the horizontal position.

31. An apparatus according to claim 30, wherein a light-emitting element is provided at each of the illuminating positions.

32. An apparatus according to claim 30, wherein said controlling means controls an illuminating position of said illuminating means so that the eye is illuminated with light from a lower side of the eye both in the state where said camera is disposed in the vertical position and in the state where said camera is disposed in the horizontal position.

33. An apparatus according to claim 25, wherein said illuminating means further comprises:

a third pair of illuminating positions symmetrically with respect to a horizontal plane including an optical axis of said finder; and a fourth pair of illuminating positions symmetrically with respect to said horizontal plane, wherein a distance between the fourth pair of illuminating positions is greater than a distance between the third pair of illuminating positions, and wherein when said camera is disposed in a vertical position, said controlling means illuminates the eye of the person with light from the third pair of illuminating positions when said person is not wearing spectacles and illuminates the eye of the person with light from the fourth pair of illuminating positions when the person is wearing spectacles.

34. An apparatus according to claim 33, wherein said illuminating means comprises:

a first pair of illuminating positions symmetrically with respect to a vertical plane including an optical axis of said finder; and a second pair of illuminating positions symmetrically with respect to the vertical plane, wherein a distance between the second pair of illuminating positions is greater than a distance between the first pair of illuminating positions, and wherein said controlling means illuminates the eye of the person with light from the first pair of illuminating positions when the person is not wearing spectacles and illuminates the eye of the person with light from the second pair of illuminating positions when the person is wearing spectacles.

35. An apparatus according to claim 25, wherein a light-emitting element is provided at each of the illuminating positions.

36. A camera comprising:

a finder comprising an eyepiece portion;

a plurality of light-emitting means provided at different illuminating positions in said eyepiece portion;

detecting means for detecting light from an eye of a person by way of an eyepiece lens; and controlling means for discriminating whether or not the person is wearing spectacles on the basis of output of said detecting means and for driving a selected light-emitting means of said plurality of light-emitting means in accordance with the discrimination result, wherein said controlling means discriminates whether or not the person is wearing spectacles by detecting whether or not a signal representative of reflection light from the spectacles is included in the output of said detecting means, said controlling means detecting a visual axis of the eye of the person on the basis of the output of said detecting means in a case where the eye is illuminated with light from said selected light-emitting means.

37. A camera according to claim 36, comprising:

a first pair of light-emitting means symmetrically with respect to a vertical plane including an optical axis of said finder; and a second pair of light-emitting means symmetrically with respect to the vertical plane, wherein a distance between said second pair of light-emitting means is greater than a distance between said first pair of light-emitting means, and wherein said controlling means illuminates the eye of the person with light from said first pair of light-emitting means when the person is not wearing spectacles and illuminates the eye of the person with light from said second pair of light-emitting means when the person is wearing spectacles.

38. A camera according to claim 37, further comprising:

a third pair of light-emitting means symmetrically with respect to a horizontal plane including an optical axis of said finder, and a fourth pair of light-emitting means symmetrically with respect to the horizontal plane, wherein a distance between said fourth pair of light-emitting means is greater than a distance between said third pair of light-emitting means, and wherein, when said camera is disposed in a vertical position, said controlling means illuminates the eye of the person with light from said third pair of light-emitting means when the person is not wearing spectacles and illuminates the eye of the person with light from said fourth pair of light-emitting means when the person is wearing spectacles.

39. A camera according to claim 36, said camera further comprising posture detecting means for detecting whether said camera is disposed in a state of a horizontal position or in a state of a vertical position, and wherein said controlling means drives a selected light-emitting means of said plurality of light-emitting means in accordance with a detection result by said posture detecting means.

40. A camera according to claim 36 wherein controlling means drives a selected light-emitting means of said plurality of light-emitting means in accordance with the detection result and the discrimination result.

41. A camera according to claim 36, wherein each of said illuminating positions is selected so that the eye is illuminated with light from a lower end of the eye of the person.

42. A camera according to claim 40, wherein the eye of the person is illuminated by a pair of light-emitting means provided symmetrically with respect to a plane including an optical axis of said finder.

43. A camera according to claim 42, wherein the visual axis is detected on the basis of a pair of positions of images of light reflected by a cornea of the eye and a position of an image of a pupil of the eye, projected on a light receiving surface of said detecting means.

* * * * *

UNITED STATES PATENT AND TRADEMARK OFFICE
CERTIFICATE OF CORRECTION

PATENT NO. : 5,485,241
DATED : January 16, 1996
INVENTOR(S) : YOSHIAKI IRIE, ET AL.

It is certified that error appears in the above-indentified patent and that said Letters Patent is hereby corrected as shown below:

IN THE SPECIFICATION:

COLUMN 1:

Line 64, "otpical" should read --optical--.

COLUMN 2:

Line 16, "(Ax*θx+BX)" should read --(Ax*θx+Bx)--.

COLUMN 5:

Line 45, "view" should read --views--; and

Line 53, "invention" should read --invention;--.

COLUMN 6:

Line 26, "a image" should read --an image--.

COLUMN 14:

Line 16, ".images" should read --images--; and

Line 49, "xp0" should read --Xp0--.

COLUMN 15

Line 10, "there" should read --it--.

UNITED STATES PATENT AND TRADEMARK OFFICE
CERTIFICATE OF CORRECTION

PATENT NO. : 5,485,241
DATED : January 16, 1996
INVENTOR(S) : YOSHIAKI IRIE, ET AL.

It is certified that error appears in the above-indentified patent and that said Letters Patent is hereby corrected as shown below:

COLUMN 18:

Line 9, "there" should read --it--.

COLUMN 19:

Line 37, "θ y 2" should read θ t h y 2--;

Line 43, "direcrent." should read --direction.--, and

Line 54, "θx=Kx*RPP+Lx" should read --θx=Kx*Rpp+Lx--.

COLUMN 20:

Line 21, "KX2" should read --Kx2--.

COLUMN 24:

Line 1, "(Pulkinye" should read --(Purkinje--;

Line 8, "Visual" should read --visual--; and

Line 29, "partical" should read --partial--.

UNITED STATES PATENT AND TRADEMARK OFFICE
CERTIFICATE OF CORRECTION

PATENT NO. : 5,485,241
DATED : January 16, 1996
INVENTOR(S) : YOSHIAKI IRIE, ET AL.

It is certified that error appears in the above-indentified patent and that said Letters Patent is hereby corrected as shown below:

COLUMN 27:

Line 26, "an" should be deleted;

Line 35, "($\epsilon 3$ $\epsilon 4$)" should read --($\epsilon 3 < \epsilon 4$);

Line 51, "clearing" should read --clearly--; and

Line 59, "is to look at" should read --comprises--.

COLUMN 28:

Line 16, "there" should read --it--;

Line 18, "whether" should read --for whether--; and

Line 55, "with" should read --with spectacles--; and "wearing." should read --wearing spectacles--.

COLUMN 31:

Line 11, "means;" should read --means,--;

Line 51, "symmetrically" should read --symmetrical--; and

Line 53, "symmetrically" should read --symmetrical--.

UNITED STATES PATENT AND TRADEMARK OFFICE
CERTIFICATE OF CORRECTION

PATENT NO. : 5,485,241
DATED : January 16, 1996
INVENTOR(S) : YOSHIAKI IRIE, ET AL.

It is certified that error appears in the above-indentified patent and that said Letters Patent is hereby corrected as shown below:

COLUMN 32:

Line 36, "symmetrically" should read --symmetrical--;

Line 38, "symmetrically" should read --symmetrical--; and

Line 54, "are" should read --is--.

COLUMN 33:

Line 11, "symmetrically" should read --symmetrical--;

Line 14, "symmetrically" should read --symmetrical--;

Line 47, "symmetrically" should read --symmetrical--;

Line 50, "symmetrically" should read --symmetrical--;

Line 65, "symmetrically" should read --symmetrical--;

UNITED STATES PATENT AND TRADEMARK OFFICE
CERTIFICATE OF CORRECTION

PATENT NO. : 5,485,241
DATED : January 16, 1996
INVENTOR(S) : YOSHIAKI IRIE, ET AL.

It is certified that error appears in the above-indentified patent and that said Letters Patent is hereby corrected as shown below:

COLUMN 34:

Line 1, "symmetrically" should read --symmetrical--;

Line 36, "symmetrically" should read --symmetrical--;

Line 39, "symmetrically" should read --symmetrical--;

Line 52, "symmetrically" should read --symmetrical--;

Line 54, "finder, and" should read --finder; and--; and

Line 55, "symmetrically" should read --symmetrical--.

COLUMN 35:

Line 1, "said camera" should be deleted; and

Line 9, "claim 36" should read --claim 39,--.

UNITED STATES PATENT AND TRADEMARK OFFICE
CERTIFICATE OF CORRECTION

PATENT NO. : 5,485,241
DATED : January 16, 1996
INVENTOR(S) : YOSHIAKI IRIE, ET AL.

It is certified that error appears in the above-indentified patent and that said Letters Patent is hereby corrected as shown below:

COLUMN 36:

Line 2, "end" should read --side--; and

Line 3, "claim 40," should read --claim 41,--.

Signed and Sealed this

Sixteenth Day of July, 1996

Attest:

BRUCE LEHMAN

Attesting Officer

Commissioner of Patents and Trademarks